(12) United States Patent
Man et al.

(10) Patent No.: US 9,365,524 B2
(45) Date of Patent: Jun. 14, 2016

(54) SOLID FORMS OF 2-(TERT-BUTYLAMINO)-4-((1R,3R,4R)-3-HYDROXY-4-METHYLCYCLOHEXYL AMINO)-PYRIMIDINE-5-CARBOXAMIDE, COMPOSITIONS THEREOF AND METHODS OF THEIR USE

(71) Applicant: Signal Pharmaceuticals, LLC, San Diego, CA (US)

(72) Inventors: Hon-Wah Man, Princeton, NJ (US); Jean Xu, Warren, NJ (US); Marie Georges Beauchamps, Randolph, NJ (US); Mohit Atul Kothare, Bridgewater, NJ (US); Nanfei Zou, Cranford, NJ (US); Ying Li, Millburn, NJ (US); Lianfeng Huang, Basking Ridge, NJ (US); Daozhong Zou, Raritan, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 14/608,314

(22) Filed: Jan. 29, 2015

(65) Prior Publication Data
US 2015/0210650 A1    Jul. 30, 2015

Related U.S. Application Data

(60) Provisional application No. 62/025,161, filed on Jul. 16, 2014, provisional application No. 61/933,636, filed on Jan. 30, 2014.

(51) Int. Cl.
*A61K 31/505* (2006.01)
*C07D 239/48* (2006.01)
*C07D 239/42* (2006.01)

(52) U.S. Cl.
CPC ............ *C07D 239/48* (2013.01); *C07D 239/42* (2013.01)

(58) Field of Classification Search
CPC ........................... A61K 31/505; C07D 239/48
See application file for complete search history.

(56) References Cited

U.S. PATENT DOCUMENTS

| | | | |
|---|---|---|---|
| 3,845,055 A | 10/1974 | Hoegerle et al. | |
| 6,432,963 B1 | 8/2002 | Hisamichi et al. | |
| 7,517,886 B2 | 4/2009 | Singh et al. | |
| 7,524,849 B2 | 4/2009 | Zhang et al. | |
| 7,589,200 B2 | 9/2009 | Singh et al. | |
| 7,718,653 B2 | 5/2010 | Barlaam et al. | |
| 7,893,074 B2 | 2/2011 | Garcia-Echeverria et al. | |
| 8,519,129 B2 | 8/2013 | Marsilje et al. | |
| 8,853,230 B2 * | 10/2014 | Bauer ................. | C07D 213/82 514/275 |
| 9,139,534 B2 * | 9/2015 | Bennett ............... | C07D 239/48 |
| 2005/0272753 A1 * | 12/2005 | Nagashima .......... | C07D 239/48 514/275 |
| 2006/0025433 A1 | 2/2006 | Barbosa et al. | |
| 2008/0139531 A1 | 6/2008 | Yanni et al. | |
| 2009/0012060 A1 | 1/2009 | Arai et al. | |
| 2009/0036440 A1 | 2/2009 | Barlaam et al. | |
| 2010/0249092 A1 | 9/2010 | Sing et al. | |
| 2011/0130415 A1 | 6/2011 | Singh et al. | |
| 2011/0159019 A1 | 6/2011 | Tanaka et al. | |
| 2012/0040968 A1 | 2/2012 | Shimada et al. | |
| 2012/0053346 A1 | 3/2012 | Maehr | |
| 2013/0029987 A1 | 1/2013 | Bennett et al. | |

FOREIGN PATENT DOCUMENTS

| | | |
|---|---|---|
| EP | 1 184 376 | 3/2002 |
| EP | 1 518 855 | 3/2005 |
| JP | 2006/124387 | 5/2006 |
| WO | WO 99/31073 | 6/1999 |
| WO | WO 0012485 | 3/2000 |
| WO | WO 00/76980 | 12/2000 |
| WO | WO 03/063794 | 8/2003 |
| WO | WO 03/078404 | 9/2003 |
| WO | WO 03/082855 | 9/2003 |
| WO | WO 2004/014382 | 2/2004 |
| WO | WO 2004/054617 | 7/2004 |
| WO | WO 2004/002964 | 8/2004 |
| WO | WO 2004/067516 | 8/2004 |
| WO | WO 2006/027377 | 3/2006 |
| WO | WO 2006/027378 | 3/2006 |
| WO | WO 2006/035069 | 4/2006 |
| WO | WO 2006/091737 | 8/2006 |
| WO | WO 2008/009458 | 1/2008 |
| WO | WO 2008/129380 | 10/2008 |
| WO | WO 2009/012421 | 1/2009 |
| WO | WO 2009/131687 | 10/2009 |
| WO | WO 2009/136995 | 11/2009 |
| WO | WO 2009/143389 | 11/2009 |
| WO | WO 2009/145856 | 12/2009 |
| WO | WO 2009/158571 | 12/2009 |
| WO | WO 2010/024430 | 3/2010 |
| WO | WO 2010/032875 | 3/2010 |
| WO | WO 2010/038081 | 4/2010 |
| WO | WO 2010/051223 | 5/2010 |
| WO | WO 2010/080864 | 7/2010 |
| WO | WO 2010/090875 | 8/2010 |

(Continued)

OTHER PUBLICATIONS

N. Le Jeune et al., 42 European Journal of Cancer, 1004-1013 (2006).*
J. Liddle et al., 21 Bioorganic & Medicinal Chemistry Letters, 6188-6194 (2011).*
Solid State Characterization of Pharmaceuticals 473-491, 490 (R.A. Storey et al., eds., 2011).*
Preformulation in Solid Dosage Form Development at 239-240 (M. C. Adeyeye et al., eds., 2008).*
Cohen, 2001, "The role of protein phosphorylation in human health and disease. The Sir Hans Krebs Medal Lecture," Eur J Biochem., 268:5001-5010.
Cohen, 2002, "Protein kinases—the major drug targets of the twenty-first century," Nat Rev Drug Discov., 1:309-315.
Das et al., 1996, "Activation of raf-1, MEK, and MAP kinase in prolactin responsive mammary cells," Breast Cancer Res. Treat., 40(2):141-149.
Davis, 1994, "MAPKs: new JNK expands the group," Trends Biochem Sci., 19:470-473.

(Continued)

*Primary Examiner* — Alexander R Pagano
(74) *Attorney, Agent, or Firm* — Jones Day

(57) ABSTRACT

Provided herein are formulations, processes, solid forms and methods of use relating to 2-(tert-butylamino)-4-((1R,3R,4R)-3-hydroxy-4-methylcyclohexylamino)-pyrimidine-5-carboxamide.

36 Claims, 45 Drawing Sheets

(56) References Cited

FOREIGN PATENT DOCUMENTS

| | | |
|---|---|---|
| WO | WO 2010/097248 | 9/2010 |
| WO | WO 2010/129802 | 11/2010 |
| WO | WO 2010/144468 | 12/2010 |
| WO | WO 2011/016472 | 2/2011 |
| WO | WO 2011/065800 | 6/2011 |
| WO | WO 2011/090760 | 7/2011 |
| WO | WO 2012/012619 | 1/2012 |
| WO | WO 2012/044936 | 4/2012 |
| WO | WO 2012/045010 | 4/2012 |
| WO | WO 2012/045020 | 4/2012 |
| WO | WO 2012/145569 | 10/2012 |

OTHER PUBLICATIONS

Eferl et al., 2008, "Development of pulmonary fibrosis through a pathway involving the transcription factor Fra-2/AP-1," PNAS, 105(30):10525-10530.
Fanger et al., 1997, "MEKKs, GCKs, MLKs, PAKs, TAKs, and tpls: upstream regulators of the c-Jun amino-terminal kinases?" Curr Opin Genet Dev., 7:67-74.
Gaestel et al., 2007, "Protein kinases as small molecule inhibitor targets in inflammation," Curr Med Chem., 14:2214-2234.
Grimminger et al., 2010, "Targeting non-malignant disorders with tyrosine kinase inhibitors," Nat Rev Drug Sisc., 9(12):956-970.
Hirabayashi et al., 2008, "A novel Syk family kinase inhibitor: design, synthesis, and structure-activity relationship of 1,2,4-triazolo[4,3-c]pyrrimidine and 1,2,4-triazolo[1,5-c]pyrimidine derivatives," Bioorg Med Chem., 16:7347-7357.
Hirosumi et al., 2002, "A central role for JNK in obesity and insulin resistance," Nature, 420:333-336.
Hisamichi et al., 2005, "Corrigendum to Synthetic studies on novel Syk inhibitors. Part 1: Synthesis and structure-activity relationships of pyrimidine-5-carboxamide derivatives," Bioorg. Med. Chem., 13:6277-6279.
Hisamichi et al., 2005, "Synthetic studies on novel Syk inhibitors. Part 1: Synthesis and structure-activity relationships of pyrimidine-5-carboxamide derivatives," Bioorg Med Chem., 13:4936-4951.
Hu et al., 2000, "Prolonged activation of the mitogen-activated protein kinase pathway is required for macrophage-like differentiation of a human myeloid leukemic cell line," Cell Growth Differ., 11(4):191-200.
ICHIJO 1999, "From receptors to stress-activated MAP kinases," Oncogene, 18:6087-6093.
Jones et al., 2012, Phase 1 Results From a Study of Romidepsin in Combination With Gemcitabine in Patients With Advanced Solid Tumors, Cancer Investigation, 30:481-486.
Kaneto et al., 2007, "Oxidative stress and the JNK pathway are involved in the development of type 1 and type 2 diabetes," Curr Mol Med., 7:674-686.
Katayama et al., 2008, "Identification of a key element for hydrogen-bonding patterns between protein kinases and their inhibitors," Proteins, 73:795-801.
Kluwe et al., 2010, "Modulation of hepatic fibrosis by c-Jun-N-terminal kinase inhibition," Gastroenterology 138:347-359.
Kodama et al., 2009, "c-Jun N-terminal kinase-1 from hematopoietic cells mediates progression from hepatic steatosis to steatohepatitis and fibrosis in mice," Gastroenterology, 137:1467-1477.e5.
Kyriakis JM., 2000, "MAP kinases and the regulation of nuclear receptors," Sci. STKE (48),pe1:1-4.
Liddle et al., 2011, "Discovery of GSK143, a highly potent, selective and orally efficacious spleen tyrosine kinase inhibitor," Bioorg Chem Chem Lett., 21:6188-6194.
Malhi et al., 2006, "Free fatty acids induce JNK-dependent hepatocyte lipoapoptosis," J Biol Chem., 281:12093-12101.
Malhi et al., 2008, "Molecular mechanisms of lipotoxicity in nonalcoholic fatty liver disease," Semin Liver Dis., 28(4):360-369.
Nagashima et al., 2007, "Synthesis and evaluation of 2-{[2-(4-hydroxyphenyl)-ethyl]amino}pyrimidine-5-carboxamide derivatives as novel STAT6 inhibitors," Bioorg Med Chem., 15:1044-1055.
Nagashima et al., 2008, "Identification of 4-benzylamino-2-[(4-morpholin-4-ylphenyl)amino]pyrimidine-5-carboxamide deriviaties as potent and orally bioavailability STAT6 inhibitors," Biorg Med Chem., 16:6509-6521.
Nagashima et al., 2009, "Novel 7H-pyrrolo[2,3-d]pyrimidine derivatives as potent and orally active STAT6 inhibitors," Bioorg Med Chem., 17:6926-6936.
Ohga et al., 2008, "YM-341619 suppresses the differentiation of spleen T cells into Th2 cells in vitro, eosinophilia, and airway hyperresponsiveness in rat allergic models," Eur J Pharmacol., 590:409-416.
Papp et al., 2007, "Steady state kinetics of spleen tyrosine kinase investigated by a real time fluorescence assay," Biochemistry, 46:15103-15114.
Reilly et al., 2011, "PRT-060318, a novel Syk inhibitor, prevents heparin-induced thrombocytopenia and thrombosis in a transgenic mouse model," Blood, 117(7):2241-2246.
Sanam et al., 2009, "Discovery of potential ZAP-70 kinase inhibitors: pharmacophore design, database screening and docking studies," Eur J Med Chem., 44:4793-4800.
Sanchez-Tillo et al., 2007, "JNK1 Is required for the induction of Mkp 1 expression in macrophages during proliferation and lipopolysaccharide-dependent activation," J Biol Chem., 282(17):12566-73.
Schramek 2002, "MAP kinases: from intracellular signals to physiology and disease," News Physiol. Sci., 17:62-67.
Segar et al., 1995, "The MAPK signaling cascade," FASEB J., 9:726-735.
Singh et al., 2009, "Differential effects of JNK1 and JNK2 inhibition on murine steatohepatitis and insulin resistance," Hepatology, 49(1):87-96.
Singh et al., 2012, "Discovery and development of spleen tyrosine kinase (SYK) inhibitors," J Med Chem., 55:3614-1643.
Sridhar et al., 2000, "Protein kinases as therapeutic targets," Pharm Res., 17(11):1345-1353.
Vallerie et al., 2010, "The role of JNK proteins in metabolism," Sci Transl Med., 2(60):1-7.
Villasenor et al., 2009, "Structural insights for design of potent spleen tyrosine kinase inhibitors from crystallographic analysis of three inhibitor complexes," Chem Biol Drug Des., 73:466-470.
Virkamaki et al., 1999, "Protein-protein interaction in insulin signaling and the molecular mechanisms of insulin resistance," J Clin Invest., 103(7):931-943.
Whitmarsh et al., 1999, "Signal transduction by MAP kinases: regulation by phosphorylation-dependent switches," Sci. STKE (1),pe1:1-3.
Xie et al., 2009, "Pharmacophore modeling study based on known spleen tyrosine kinase inhibitors together with virtual screening for identifying novel inhibitors," Bioorg Med Chem Lett., 19:1944-1949.
Uehara et al., 2004, "c-Jun N-Terminal Kinase Mediates Hepatic Injury after Rat Liver Transplantation," Transplantation, 78(3):324-332.
Schwabe et al., 2004, "Differential requirement for c-Jun NH2-terminal kinase in TNF-α- and Fas-mediated apoptosis in hepatocytes," FASEB J. 18(6):720-722.
Bundgaard, "Design of prodrugs: Bioreversible derivatives for various functional groups and chemical entities," Design of Prodrugs, Chapter 1, p. 1, 1985.
Silverman, 1992, "Prodrugs and Drug Delivery Systems," The Organic Chemistry of Drug Design and Drug action, Chapter 8, pp. 352-400.
Hulikal, "L15 Deuterium Labeled Compounds in Drug Discovery Process," Abstract, 2010.
Pimlott, PubMed Abstract (Nucl Med Commun. 26(3):183-8), 2005.
Goff, PubMed Abstract (J Gene Med 3(6):517-28), No—Dec. 2001.
Bosseray et al., PubMed Abstract (Pathol Biol (Paris) 50(8):483-92), Oct. 2002.
Razonable et al., PubMed Abstract (Herpes 10(3):60-5), Dec. 2003.
Douglas, Jr., "Introduction to Viral Diseases," Cecil Textbook of Medicine, 20th Edition, vol. 2, pp. 1739-1747, 1996.
Bogoyevitch et al., 2010, "c-Jun N-terminal kinase (JNK) signaling: Recent advances and challenges," Biochimica et Biophysica Acta 1804:4630475.

\* cited by examiner

SOLID FORMS OF 2-(TERT-BUTYLAMINO)-4-((1R,3R,4R)-3-HYDROXY-4-METHYLCYCLOHEXYLAMINO)-PYRIMIDINE-5-CARBOXAMIDE, COMPOSITIONS THEREOF AND METHODS OF THEIR USE

CROSS-REFERENCE TO RELATED APPLICATIONS

This application claims the benefit of U.S. Provisional Application No. 61/933,636, filed Jan. 30, 2014 and claims the benefit of U.S. Provisional Application No. 62/025,161, filed Jul. 16, 2014, the entire contents of each of which are incorporated herein by reference.

FIELD

Provided herein are methods of making and solid forms of 2-(tert-butylamino)-4-((1R,3R,4R)-3-hydroxy-4-methylcyclohexylamino)-pyrimidine-5-carboxamide, compositions thereof, methods of their use for the treatment of a disease, disorder, or condition, and the solid forms for use in such methods.

BACKGROUND

The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette). The importance of discovering polymorphs was underscored by the case of Ritonavir™, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The compound chemically named 2-(tert-butylamino)-4-((1R,3R,4R)-3-hydroxy-4-methylcyclohexylamino)-pyrimidine-5-carboxamide (alternatively named 2-[(1,1-dimethylethyl)amino]-4-[[(1R,3R,4R)-3-hydroxy-4-methylcyclohexyl]amino]-5-pyrimidinecarboxamide) and tautomers thereof (collectively referred to herein as "Compound 1") are disclosed in U.S. Patent Application Publication No. 2013/0029987, published on Jan. 31, 2013, and International Pub. No. WO2012/145569, the entireties of each of which are incorporated by reference herein.

The variety of possible solid forms creates potential diversity in physical and chemical properties for a given pharmaceutical compound. The discovery and selection of solid forms are of great importance in the development of an effective, stable and marketable pharmaceutical product.

The connection between abnormal protein phosphorylation and the cause or consequence of diseases has been known for over 20 years. Accordingly, protein kinases have become a very important group of drug targets. (See Cohen, *Nature*, 1:309-315 (2002), Gaestel et al. *Curr. Med. Chem.* 14: 2214-223 (2007); Grimminger et al. *Nat. Rev. Drug Disc.* 9(12): 956-970 (2010)). Various protein kinase inhibitors have been used clinically in the treatment of a wide variety of diseases, such as cancer and chronic inflammatory diseases, including rheumatoid arthritis and psoriasis. (See Cohen, *Eur. J. Biochem.*, 268:5001-5010 (2001); Protein Kinase Inhibitors for the Treatment of Disease: The Promise and the Problems, *Handbook of Experimental Pharmacology*, Springer Berlin Heidelberg, 167 (2005)).

JNK is a ubiquitously expressed serine/threonine kinase belonging, together with ERK (extracellular-regulated kinase) and p38, to the family of mitogen-activated protein kinases (MAPKs). (Kyriakis J M, *Sci. STKE* (48):pe1 (2000); Whitmarsh A J, et al. *Sci. STKE* (1):pe1 (1999); Schramek H, *News Physiol. Sci.* 17:62-7 (2002); Ichijo H, *Oncogene* 18(45):6087-93 (1999)). MAPKs are important mediators of signal transduction from the cell surface to the nucleus, using phosphorylation cascades to generate a coordinated response by a cell to an external stimulus by phosphorylation of selected intracellular proteins, including transcription factors. Additionally, JNK also phosphorylates non-nuclear proteins, for example, IRS-1, and Bcl-2 family members. (Davis R J, *Trends Biochem. Sci.* 9(11):470-473 (1994); Seger R et al., *FASEB J.;* 9(9):726-35 (1995); Fanger G R et al., *Curr. Opin. Genet. Dev.;* 7(1):67-74 (1997)).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators, for example, JNK modulators, and in particular solid forms of those kinase modulators.

Citation or identification of any reference in Section 2 of this application is not to be construed as an admission that the reference is prior art to the present application.

SUMMARY

Provided herein are solid forms of Compound 1:

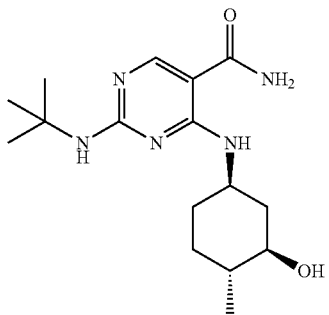

having the name 2-(tert-butylamino)-4-((1R,3R,4R)-3-hydroxy-4-methylcyclohexylamino)-pyrimidine-5-carboxamide, including tautomers thereof. Also provided are methods of preparing, isolating, and characterizing the solid forms.

In another aspect, provided herein are methods for preparing certain compounds, including Compound 1 as described herein, as well as intermediates useful in such methods.

In certain aspects, the solid forms of Compound 1 are useful for inhibiting a kinase in a cell expressing said kinase, for example JNK1 or JNK2. In other aspects, solid forms of Compound 1 are useful for treating or preventing a condition treatable or preventable by inhibition of a JNK pathway, as described herein. In another aspect, the solid forms of Compound 1 are useful for treating or preventing one or more disorders selected from interstitial pulmonary fibrosis, systemic sclerosis, scleroderma, chronic allograft nephropathy, antibody mediated rejection, or lupus. In yet another aspect, the solid forms of Compound 1 are useful for treating or preventing liver fibrotic disorders, or diabetes and/or metabolic syndrome leading to liver fibrotic disorders, as described herein.

The present embodiments can be understood more fully by reference to the detailed description and examples, which are intended to exemplify non-limiting embodiments.

DETAILED DESCRIPTION

Definitions

Figure 1:
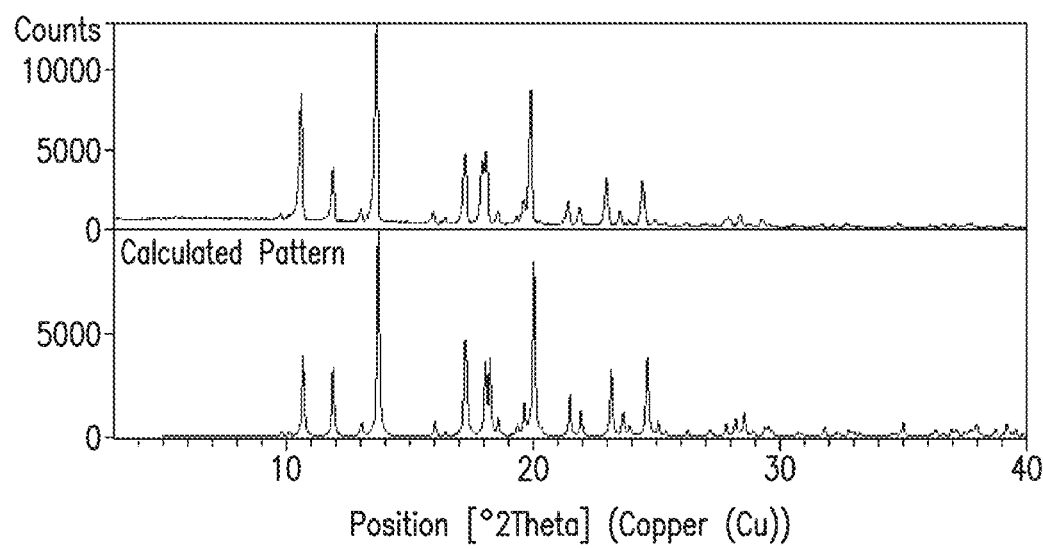
FIG. 1 depicts an overlay of an X-ray powder diffractogram (XRPD) pattern (top) and a simulated XRPD pattern (bottom) of Form A.

As used herein, and in the specification and the accompanying claims, the indefinite articles "a" and "an" and the definite article "the" include plural as well as single referents, unless the context clearly indicates otherwise.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous solids include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an XRPD peak position may vary by up to ±0.2° 2θ (or ±0.2 degree 2θ) while still describing the particular XRPD peak.

As used herein, and unless otherwise specified, a crystalline that is "pure," i.e., substantially free of other crystalline or amorphous solids, contains less than about 10% by weight of one or more other crystalline or amorphous solids, less than about 5% by weight of one or more other crystalline or amorphous solids, less than about 3% by weight of one or more other crystalline or amorphous solids, or less than about 1% by weight of one or more other crystalline or amorphous solids.

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," as used herein, refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or 2 to 4 carbon atoms. Representative alkyl groups include -methyl, -ethyl, -n-propyl, -n-butyl, -n-pentyl, and -n-hexyl; while saturated branched alkyls include -isopropyl, -sec-butyl, -isobutyl, -tert-butyl, -isopentyl, -neopentyl, -tert-pentyl, -2-methylphenyl, -3-methylphenyl, -4-methylphenyl, -2,3-dimethylbutyl and the like. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are as defined above. Substituted cycloalkylalkyl groups may be substituted at the alkyl, the cycloalkyl, or both the alkyl and the cycloalkyl portions of the group. Representative cycloalkylalkyl groups include but are not limited to methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopentyl, propylcyclohexyl and the like.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocyclylalkyl groups include but are not limited to 4-ethylmorpholinyl, 4-propylmorpholinyl, furan-2-yl methyl, furan-3-yl methyl, pyridin-3-yl methyl, tetrahydrofuran-2-yl ethyl, and indol-2-yl propyl. When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amine; alkylamine; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); $B(OH)_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

A "halogen" is chloro, iodo, bromo, or fluoro.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amine" group is a radical of the formula: $-NH_2$.

A "hydroxyl amine" group is a radical of the formula: $-N(R^\#)OH$ or —NHOH, wherein $R^\#$ is a substituted or unsubstituted alkyl, cycloalkyl, cycloalkylalkyl, aryl, aralkyl, heterocyclyl or heterocyclylalkyl group as defined herein.

An "alkoxyamine" group is a radical of the formula: $-N(R^\#)$O-alkyl or —NHO-alkyl, wherein $R^\#$ is as defined above.

An "aralkoxyamine" group is a radical of the formula: $-N(R^\#)$O-aryl or —NHO-aryl, wherein $R^\#$ is as defined above.

An "alkylamine" group is a radical of the formula: —NH-alkyl or $-N(alkyl)_2$, wherein each alkyl is independently as defined above.

An "aminocarbonyl" group is a radical of the formula: $-C(=O)N(R^\#)_2$, $-C(=O)NH(R^\#)$ or $-C(=O)NH_2$, wherein each $R^\#$ is as defined above.

An "acylamino" group is a radical of the formula: $-NHC(=O)(R^\#)$ or $-N(alkyl)C(=O)(R^\#)$, wherein each alkyl and $R^\#$ are independently as defined above.

An "O(alkyl)aminocarbonyl" group is a radical of the formula: $-O(alkyl)C(=O)N(R^\#)_2$, $-O(alkyl)C(=O)NH(R^\#)$ or $-O(alkyl)C(=O)NH_2$, wherein each $R^\#$ is independently as defined above.

An "N-oxide" group is a radical of the formula: $-N^+-O^-$.

A "carboxy" group is a radical of the formula: $-C(=O)$OH.

A "ketone" group is a radical of the formula: $-C(=O)(R^\#)$, wherein $R^\#$ is as defined above.

An "aldehyde" group is a radical of the formula: —CH(=O).

An "ester" group is a radical of the formula: $-C(=O)O(R^\#)$ or $-OC(=O)(R^\#)$, wherein $R^\#$ is as defined above.

A "urea" group is a radical of the formula: $-N(alkyl)C(=O)N(R^\#)_2$, $N(alkyl)C(=O)NH(R^\#)$, $-N(alkyl)C(=O)NH_2$, $-NHC(=O)N(R^\#)_2$, $-NHC(=O)NH(R^\#)$, or $-NHC(=O)NH_2^\#$, wherein each alkyl and $R^\#$ are independently as defined above.

An "imine" group is a radical of the formula: $-N=C(R^\#)_2$ or $-C(R^\#)=N(R^\#)$, wherein each $R^\#$ is independently as defined above.

An "imide" group is a radical of the formula: $-C(=O)N(R\#)C(=O)(R^\#)$ or $-N((C=O)(R^\#))_2$, wherein each $R^\#$ is independently as defined above.

A "urethane" group is a radical of the formula: $-OC(=O)N(R^\#)_2$, $-OC(=O)NH(R^\#)$, $-N(R^\#)C(=O)O(R^\#)$, or $-NHC(=O)O(R^\#)$, wherein each $R^\#$ is independently as defined above.

An "amidine" group is a radical of the formula: $-C(=N(R^\#))N(R^\#)_2$, $-C(=N(R^\#))NH(R^\#)$, $-C(=N(R^\#))NH_2$, $-C(=NH)N(R^\#)_2$, $-C(=NH)NH(R^\#)$, $-C(=NH)NH_2$, $-N=C(R^\#)N(R^\#)_2$, $-N=C(R^\#)NH(R^\#)$, $-N=C(R^\#)NH_2$, $-N(R^\#)C(R^\#)=N(R^\#)$, $-NHC(R^\#)=N(R^\#)$, $-N(R^\#)C(R^\#)=NH$, or $-NHC(R^\#)=NH$, wherein each $R^\#$ is independently as defined above.

A "guanidine" group is a radical of the formula: $-N(R^\#)C(=N(R^\#))N(R^\#)_2$, $-NHC(=N(R^\#))N(R^\#)_2$, $-N(R^\#)C(=NH)N(R^\#)_2$, $-N(R^\#)C(=N(R^\#))NH(R^\#)$, $-N(R^\#)C(=N(R^\#))NH_2$, $-NHC(=NH)N(R^\#)_2$, $-NHC(=N(R^\#))NH(R^\#)$, $-NHC(=N(R^\#))NH_2$, $-NHC(=NH)NH(R^\#)$, $-NHC(=NH)NH_2$, $-N=C(N(R^\#)_2)_2$, $-N=C(NH(R^\#))_2$, or $-N=C(NH_2)_2$, wherein each $R^\#$ is independently as defined above.

A "enamine" group is a radical of the formula: $-N(R^\#)C(R^\#)=C(R^\#)_2$, $-NHC(R^\#)=C(R^\#)_2$, $-C(N(R^\#)_2)=C(R^\#)_2$, $-C(NH(R^\#))=C(R^\#)_2$, $-C(NH_2)=C(R^\#)_2$, $-C(R^\#)=C(R^\#)(N(R^\#)_2)$, $-C(R^\#)=C(R^\#)(NH(R^\#))$ or $-C(R^\#)=C(R^\#)(NH_2)$, wherein each $R^\#$ is independently as defined above.

An "oxime" group is a radical of the formula: $-C(=NO(R^\#))(R^\#)$, $-C(=NOH)(R^\#)$, $-CH(=NO(R^\#))$, or $-CH(=NOH)$, wherein each $R^\#$ is independently as defined above.

A "hydrazide" group is a radical of the formula: $-C(=O)N(R^\#)N(R^\#)_2$, $-C(=O)NHN(R^\#)_2$, $-C(=O)N(R^\#)NH(R^\#)$, $-C(=O)N(R^\#)NH_2$, $-C(=O)NHNH(R^\#)_2$, or $-C(=O)NHNH_2$, wherein each $R^\#$ is independently as defined above.

A "hydrazine" group is a radical of the formula: $-N(R^\#)N(R^\#)_2$, $-NHN(R^\#)_2$, $-N(R^\#)NH(R^\#)$, $-N(R^\#)NH_2$, $-NHNH(R^\#)_2$, or $-NHNH_2$, wherein each $R^\#$ is independently as defined above.

A "hydrazone" group is a radical of the formula: $-C(=N-N(R^\#)_2)(R^\#)_2$, $-C(=N-NH(R^\#))(R^\#)_2$, $-C(=N-NH_2)(R^\#)_2$, $-N(R^\#)(N=C(R^\#)_2)$, or $-NH(N=C(R^\#)_2)$, wherein each $R^\#$ is independently as defined above.

An "azide" group is a radical of the formula: $-N_3$.

An "isocyanate" group is a radical of the formula: —N=C=O.

An "isothiocyanate" group is a radical of the formula: —N=C=S.

A "cyanate" group is a radical of the formula: —OCN.

A "thiocyanate" group is a radical of the formula: —SCN.

A "thioether" group is a radical of the formula; $-S(R^\#)$, wherein $R^\#$ is as defined above.

A "thiocarbonyl" group is a radical of the formula: —C(=S)(R#), wherein R# is as defined above.

A "sulfinyl" group is a radical of the formula: —S(=O)(R#), wherein R# is as defined above.

A "sulfone" group is a radical of the formula: —S(=O)₂(R#), wherein R# is as defined above.

A "sulfonylamino" group is a radical of the formula: —NHSO₂(R#) or —N(alkyl)SO₂(R#), wherein each alkyl and R# are defined above.

A "sulfonamide" group is a radical of the formula: —S(=O)₂N(R#)₂, or —S(=O)₂NH(R#), or —S(=O)₂NH₂, wherein each R# is independently as defined above.

A "phosphonate" group is a radical of the formula: —P(=O)(O(R#))₂, —P(=O)(OH)₂, —OP(=O)(O(R#))(R#), or —OP(=O)(OH)(R#), wherein each R# is independently as defined above.

A "phosphine" group is a radical of the formula: —P(R#)₂, wherein each R# is independently as defined above.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

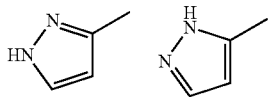

As readily understood by one skilled in the art, a wide variety of functional groups and other structures may exhibit tautomerism and all tautomers of Compound 1 are within the scope of the present invention.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

The term "solid form" refers to a physical form which is not predominantly in a liquid or a gaseous state. As used herein and unless otherwise specified, the term "solid form," when used herein to refer to Compound 1, refers to a physical form comprising Compound 1 which is not predominantly in a liquid or a gaseous state. A solid form may be a crystalline form or a mixture thereof. In certain embodiments, a solid form may be a liquid crystal. In certain embodiments, the term "solid forms comprising Compound 1" includes crystal forms comprising Compound 1. In certain embodiments, the solid form of Compound 1 is Form A, Form B, Form C, Form D, Form E, Form F, Form G, Form H, Form I, the amorphous solid, or a mixture thereof.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

The term "crystal form" or "crystalline form" refers to a solid form that is crystalline. In certain embodiments, a crystal form of a substance may be substantially free of amorphous solids and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous solids and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

Unless otherwise specified, the term "amorphous" or "amorphous solid" means that the substance, component, or product in question is not substantially crystalline as determined by X-ray diffraction. In particular, the term "amorphous solid" describes a disordered solid form, i.e., a solid form lacking long range crystalline order. In certain embodiments, an amorphous solid of a substance may be substantially free of other amorphous solids and/or crystal forms. In certain embodiments, an amorphous solid of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous solids and/or crystal forms on a weight basis. In certain embodiments, an amorphous solid of a substance may be physically and/or chemically pure. In certain embodiments, an amorphous solid of a substance be about 99%, about 98%, about 97%, about 96%, about 95%, about 94%, about 93%, about 92%, about 91%, or about 90% physically and/or chemically pure.

"JNK" means a protein or an isoform thereof expressed by a JNK1, JNK2, or JNK3 gene (Gupta, S., Barrett, T., Whitmarsh, A. J., Cavanagh, J., Sluss, H. K., Derijard, B. and Davis, R. J. The EMBO J. 15:2760-2770 (1996)).

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a condition treatable or preventable by inhibition of a JNK pathway, as described herein. In another embodiment, the disorder is selected from interstitial pulmonary fibrosis, systemic sclerosis, scleroderma, chronic allograft nephropathy, antibody mediated rejection, or lupus. In yet another embodiment, the disorder is a liver fibrotic disorder, or diabetes and/or metabolic syndrome leading to liver fibrotic disorders, as described herein. In some embodiments, the disorder is a liver fibrotic disorder, such as non-alcoholic steatohepatitis, steatosis (i.e. fatty liver), cirrhosis, primary sclerosing cholangitis, primary biliary cirrhosis, hepatitis, hepatocellular carcinoma, or liver fibrosis coincident with chronic or repeated alcohol ingestion (alcoholic hepatitis), with infection (e.g., viral infection such as HCV), with liver transplant, or with drug induced liver injury (e.g., acetaminophen toxicity). In some embodiments, "treating" means an alleviation, in whole or in part, of a disorder, disease or condition, or symptoms associated with diabetes or metabolic syndrome leading to liver fibrotic disorders, such as non-alcoholic steatohepatitis, steatosis (i.e. fatty liver), hepatitis or cirrhosis, or a slowing, or halting of further progression or worsening of those symptoms. In one embodiment, the symptom is jaundice.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a condition treatable or preventable by inhibition of a JNK pathway, as described herein. In another embodiment, the disorder is selected from interstitial pulmonary fibrosis, systemic sclerosis, scleroderma, chronic allograft nephropathy, antibody mediated rejection, or lupus. In one embodiment, the disorder is a liver fibrotic disorder, or diabetes or metabolic syndrome leading to liver fibrotic disorders, as described herein, or symptoms thereof.

The term "effective amount" in connection with a solid form of Compound 1 means an amount capable of treating or preventing a disorder, disease or condition, or symptoms thereof, disclosed herein.

"Patient" or "subject" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like, in one embodiment a mammal, in another embodiment a human. In one embodiment, a subject is a human having or at risk for having interstitial pulmonary fibrosis, systemic sclerosis, scleroderma, chronic allograft nephropathy, antibody mediated rejection, or lupus. In another, a subject is a human having or at risk for having liver fibrotic disorders or diabetes or metabolic syndrome leading to liver fibrotic disorders, or a condition, treatable or preventable by inhibition of a JNK pathway, or a symptom thereof.

Compound 1

The solid forms, formulations and methods of use provided herein relate to solid forms (e.g., polymorphs) of Compound 1:

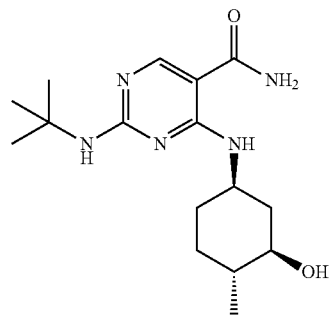

having the alternative names 2-(tert-butylamino)-4-((1R,3R,4R)-3-hydroxy-4-methylcyclohexylamino)-pyrimidine-5-carboxamide or 2-[(1,1-dimethylethyl)amino]-4-[[(1R,3R,4R)-3-hydroxy-4-methylcyclohexyl]amino]-5-pyrimidinecarboxamide, including tautomers thereof.

In another aspect, provided herein are methods for preparing certain compounds, including Compound 1 as described herein, as well as intermediates useful in such methods.

Compound 1 can be prepared using reagents and methods known in the art, including the methods provided in U.S. Patent Application Publication No. 2013/0029987, published on Jan. 31, 2013, and International Patent Application Publication No. WO2012/145569, the entire contents of each of which are incorporated herein by reference.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Methods for Making Compound 1

By way of example and not limitation, Diaminopyrimidine Compounds of formula (iv) can be prepared as outlined in Scheme 1 shown below, as well as in the examples set forth herein.

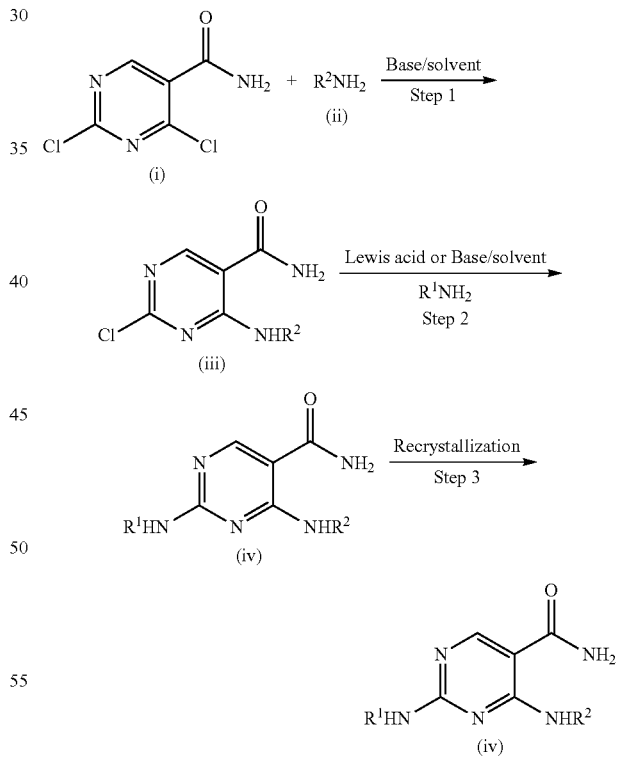

In certain embodiments of formula (iv), $R^2$ is substituted or unsubstituted $C_{1-8}$ alkyl, or substituted or unsubstituted saturated cycloalkyl. In certain embodiments of formula (iv), $R^1$ is substituted or unsubstituted $C_{1-8}$ alkyl, or substituted or unsubstituted cycloalkyl.

In some embodiments, $R^2$ is (1R,3R,4R)-3-hydroxyl-4-methyl-cyclohexyl, tert-butyl or 1-bicyclo[1.1.1]pentyl.

In some embodiments, $R^2$ is

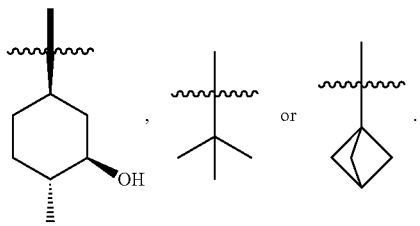

In some embodiments, $R^1$ is tert-butyl, trans-4-hydroxyl-cyclohexyl or (1R,3S)-3-hydroxyl-cyclohexyl.

In some embodiments, $R^1$ is

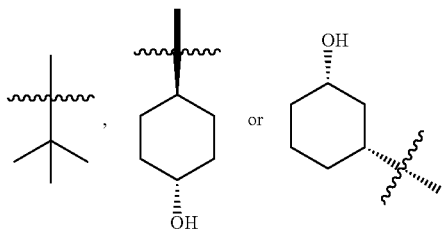

In one embodiment, the compound of formula (iv) is Compound 1.

Treatment of 2,4-dichloropyrimidine-5-carboxamide (i) with $R^2NH_2$ (ii) in a solvent (e.g., tetrahydrofuran (THF), N-methyl-2-pyrrolidone (NMP) or water) in the presence of a base (e.g., diisopropylethylamine, potassium carbonate, potassium phosphate dibasic, potassium phosphate tribasic or sodium bicarbonate) at about 0° C. to about 25° C. provides introduction of the $R^2$ sidechain to yield compounds of formula (iii). The desired regioisomer compound is further derivatized by subsequent treatment with $R^1NH_2$ in an organic solvent (e.g., acetonitrile, EtOAc, THF, NMP, dimethyl sulfoxide (DMSO) or sulfolane) in the presence of a base (e.g., t-butylamine or sodium carbonate) or a Lewis acid (e.g., $ZnCl_2$) at elevated temperature (e.g., about 60° C. to about 85° C.), optionally under nitrogen pressure, which provides introduction of the $R^1$ sidechain to yield compounds of formula (iv). Recrystallization of the compounds of formula (iv) in a solvent system (e.g., 2-propanol/water or ethanol/water) provides the compounds of formula (iv) with improved purity.

In one aspect, provided herein are methods for preparing a compound of formula (iv):

(iv)

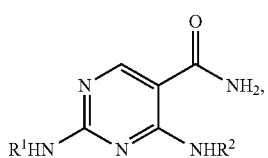

the methods comprising contacting a compound of formula (iii)

(iii)

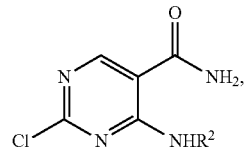

with $R^1NH_2$ in the presence of a base or a Lewis acid in a solvent;

wherein $R^1$ is substituted or unsubstituted $C_{1-8}$ alkyl, or substituted or unsubstituted saturated cycloalkyl; and $R^2$ is substituted or unsubstituted $C_{1-8}$ alkyl, or substituted or unsubstituted saturated cycloalkyl.

In some embodiments, the solvent is DMSO, sulfolane, acetonitrile, DMF, DMAc, NMP, EtOH, n-PrOH, IPA, n-BuOH, t-BuOH, EtOAc, IPAc, toluene, 2-MeTHF, THF, DCM, or mixed solvents, such as: THF/water, THF/NMP, sulfolane/water, DMSO/water, IPA/water, EtOH/water. In some embodiments, the solvent is acetonitrile, EtOAc, THF, NMP, DMSO or sulfolane.

In some embodiments, the base is N,N-diisopropylethylamine, DBU, triethylamine, tert-butylamine, sodium carbonate, potassium carbonate, sodium hydrogen carbonate, sodium acetate, or potassium phosphate. In some embodiments, the base is t-butylamine or sodium carbonate.

In some embodiments, the Lewis acid is $ZnCl_2$, $ZnBr_2$, $AlCl_3$, $Zn(OTf)_2$. In some embodiments, the Lewis acid is $ZnCl_2$.

In some embodiments, the contacting is performed at elevated temperature, e.g., about 60° C. to about 85° C.

In some embodiments, the contacting is performed under nitrogen pressure.

In some embodiments, the methods further comprise preparing a compound of formula (iii)

(iii)

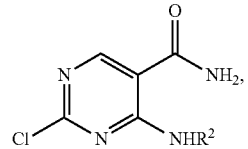

the methods comprising contacting of 2,4-dichloropyrimidine-5-carboxamide (i) with $R^2NH_2$ (ii) in the presence of a base in a solvent.

In some embodiments, the solvent is THF, NMP, water or mixed solvents, such as THF/water or NMP/water. In one embodiment, the solvent is THF, NMP or THF/water. In some embodiments, the base is N,N-diisopropylethylamine, potassium carbonate, potassium phosphate dibasic, potassium phosphate tribasic or sodium bicarbonate. In some embodiments, the base is N,N-diisopropylethylamine, potassium carbonate, or sodium bicarbonate. In some embodiments, the contacting is performed at about 0° C. to about 25° C.

In one aspect, provided herein are methods for purifying a compound of formula (iv):

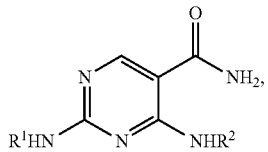

wherein $R^1$ is substituted or unsubstituted $C_{1-8}$ alkyl, or substituted or unsubstituted cycloalkyl; and $R^2$ is substituted or unsubstituted $C_{1-8}$ alkyl, or substituted or unsubstituted cycloalkyl, the method comprising 1) dissolving the compound of formula (iv) in a first solvent at a first temperature; 2) adding a second solvent into the resulting solution; 3) cooling the solution to a second temperature; and 4) collecting a solid.

In some embodiments, the method additionally comprises seeding with Form A. In certain embodiments, the method additionally comprises seeding with Form A after step 2) and before step 3). In certain embodiments, the method additionally comprises seeding with Form A during step 3). In certain embodiments, the method additionally comprises seeding with Form A after step 3) and before step 4). In some such embodiments, Form A is micronized. In certain embodiments, the method additionally comprises seeding with micronized Form A after step 2) and before step 3).

In some embodiments, the first solvent is: i) a mixture of 2-propanol and water (e.g., wherein the ratio by volume of 2-propanol and water in the mixture is about 3:1); ii) DMSO; or iii) ethanol.

In some embodiments, the second solvent is water.

In some embodiments, the first temperature is from about 60° C. to about 70° C.

In some embodiments, the second temperature is from about 0° C. to about 25° C.

Provided herein are compounds having the following formula (iii):

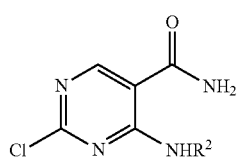

and tautomers thereof, wherein $R^2$ is substituted or unsubstituted $C_{1-8}$ alkyl, or substituted saturated cycloalkyl.

In certain embodiments of formula (iii), $R^2$ is (1R,3R,4R)-3-hydroxyl-4-methyl-cyclohexyl, tert-butyl or 1-bicyclo[1.1.1]pentyl.

In certain embodiments of formula (iii), $R^2$ is

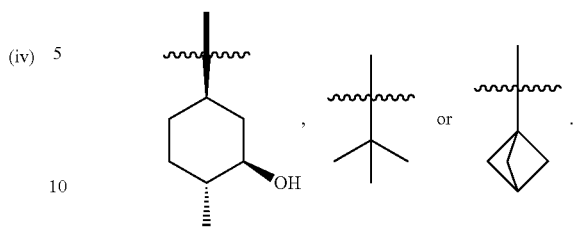

In one embodiment, provided herein is a method for preparing Compound 1 as described in Scheme 2 shown below, as well as in the examples set forth herein.

Scheme 2

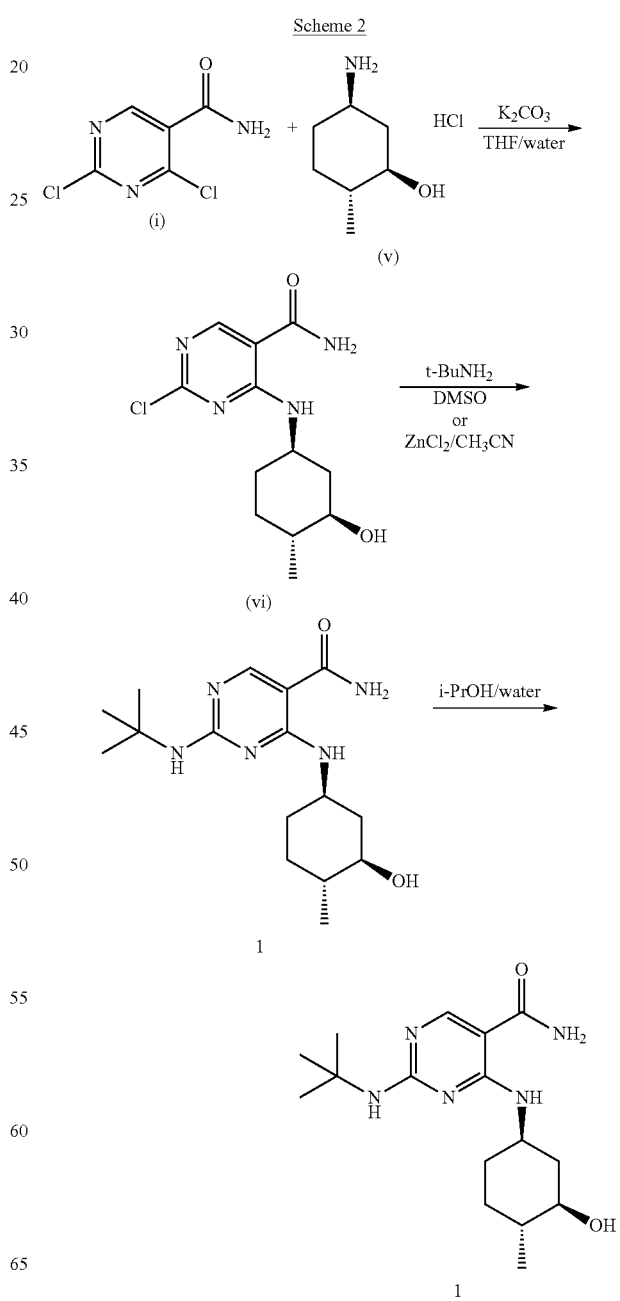

In one embodiment, treatment of 2,4-dichloropyrimidine-5-carboxamide (i) with (1R,2R,5R)-5-amino-2-methylcyclohexanol hydrochloride (v) in THF in the presence of potassium carbonate at about 0° C. to about 25° C. provides introduction of the (1R,2R,5R)-5-amino-2-methylcyclohexanol sidechain to yield compound (vi). Subsequent treatment with t-BuNH$_2$ in DMSO at about 68° C. or with t-BuNH$_2$ in the presence of ZnCl$_2$ in ACN provides introduction of the t-BuNH$_2$ sidechain to yield Compound 1. Recrystallization of Compound 1 in a mixture of IPA and water at about 70° C. provides Compound 1 with improved purity.

In one aspect, provided herein are methods for preparing a compound of formula (A):

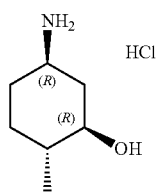

(A)

the methods comprising contacting a compound of formula (9a):

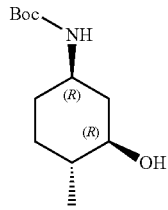

(9a)

with hydrochloric acid in a solvent.

In some embodiments, the solvent is methanol, 2-propanol, ether or dioxane.

In some embodiments, the methods further comprise preparing a compound of formula (9a):

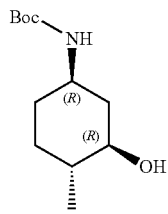

(9a)

the methods comprising separating a diastereomeric mixture of compounds of formulae (9a and 9b):

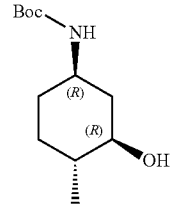

(9a)

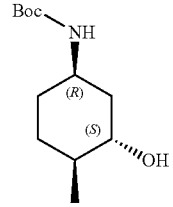

(9b)

by employing a chiral separation method.

In one embodiment, the chiral separation method is chiral supercritical fluid chromatography (SFC), recrystallization, chiral HPLC, chiral LC, or chiral resolution. In one embodiment, the chiral separation method is chiral supercritical fluid chromatography (SFC). In one embodiment, the diastereomeric mixture is a 1:1 mixture.

In some embodiments, the methods further comprise preparing a diastereomeric mixture of compounds of formulae (9a and 9b):

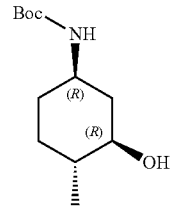

(9a)

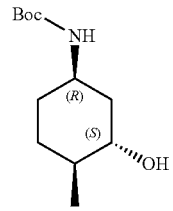

(9b)

the methods comprising contacting a compound of formula (8):

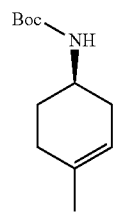

(8)

with a hydroborating agent, followed by treatment with an oxidant, in a solvent, in the presence of a base.

In one embodiment, the hydroborating agent is BH$_3$/THF, B$_2$H$_6$, 9-BBN, BCl$_3$/Me$_3$SiH, or (+)-diisopinocampheylborane. In one embodiment, the hydroborating agent is $BH_3$/THF. In one embodiment, the oxidant is $H_2O_2$ or oxone. In another, the oxidant is $H_2O_2$. In another embodiment, the solvent is THF or EtOH. In another embodiment, the solvent is THF. In yet another embodiment, the base is NaOH.

In some embodiments, the methods further comprise preparing a compound of formula (8):

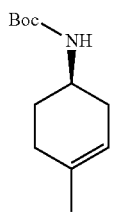

(8)

the methods comprising contacting a compound of formula (7):

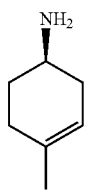

(7)

with $Boc_2O$ in an organic solvent, optionally in the presence of a base. In one embodiment, the organic solvent is DCM or ether. In one embodiment, the base is triethylamine.

In some embodiments, the methods further comprise preparing a compound of formula (7):

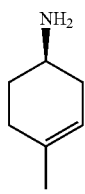

(7)

the methods comprising contacting a compound of formula (6):

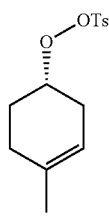

(6)

with an azidation agent in an organic solvent, followed by reducing the resulting azide derivative in an organic solvent.

In one embodiment, the azidation agent is $NaN_3$. In another, the reducing agent is $LiAlH_4$. In some embodiments, the solvent is selected from DMF, toluene, ACN, DCM, THF, or ether.

In some embodiments, the methods further comprise preparing a compound of formula (6):

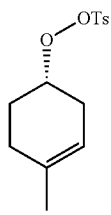

(6)

the methods comprising contacting a compound of formula (5):

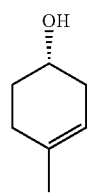

(5)

with tosyl chloride in an organic solvent, in the presence of a base.

In some embodiments, the organic solvent is selected from DMF, toluene, ACN, DCM, THF, or ether. In others, the base is triethylamine or pyridine.

In some embodiments, the methods further comprise preparing a compound of formula (5):

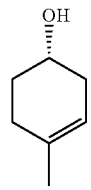

(5)

the methods comprising contacting a compound of formula (4):

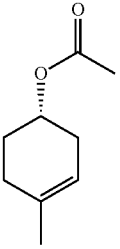

(4)

with a reducing agent in a solvent.

In some embodiments, the reducing agent is $LiAlH_4$. In others, the solvent is THF or ether.

In some embodiments, the methods further comprise preparing a compound of formula (4):

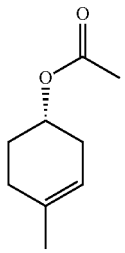
(4)

the methods comprising contacting a compound of formula (3):

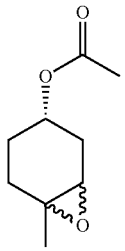
(3)

with Zn and NaI, in the presence of acetic acid.

In some embodiments, the methods further comprise preparing a compound of formula (3):

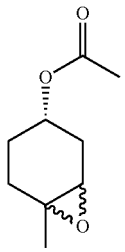
(3)

the methods comprising contacting a compound of formula (2):

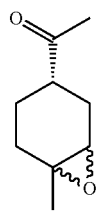
(2)

with a peracid, in a solvent.

In some embodiments, the peracid is m-CPBA. In others, the solvent is DCM.

In some embodiments, the methods further comprise preparing a compound of formula (2):

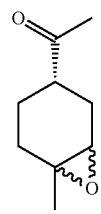
(2)

the methods comprising ozonolyzing a compound of formula (Y):

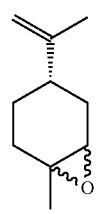
(Y)

in the presence of ozone.

In some embodiments, the methods further comprise preparing a compound of formula (Y):

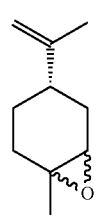
(Y)

the methods comprising contacting (−)-limonene having a formula:

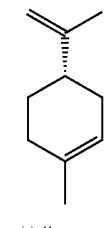

(−)-limonene with a peracid, in a solvent.

In some embodiments, the peracid is m-CPBA. In others, the solvent is DCM.

In one aspect, provided herein are methods for preparing a compound of formula (10):

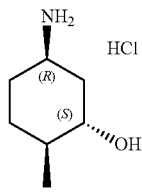
(10)

the methods comprising contacting a compound of formula (9b):

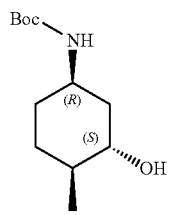
(9b)

with hydrochloric acid in a solvent.

In some embodiments, the solvent is 2-propanol, methanol, ether or dioxane.

In some embodiments, the methods further comprise preparing a compound of formula (9b):

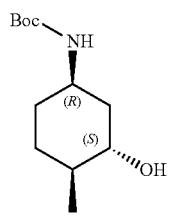
(9b)

the methods comprising separating a diastereomeric mixture of compounds of formulae (9a and 9b):

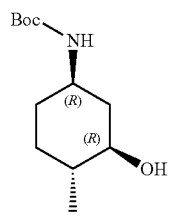
(9a)

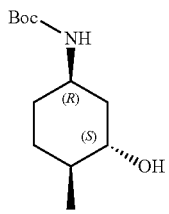
(9b)

by employing a chiral separation method.

In one embodiment, the chiral separation method is chiral supercritical fluid chromatography (SFC), recrystallization, chiral HPLC, chiral LC, or chiral resolution. In one embodiment, the chiral separation method is chiral supercritical fluid chromatography (SFC). In one embodiment, the diastereomeric mixture is a 1:1 mixture.

In some embodiments, the methods further comprise preparing a diastereomeric mixture of compounds of formulae (9a and 9b):

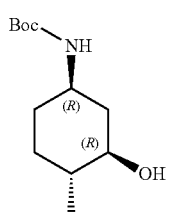
(9a)

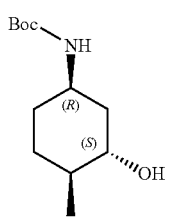
(9b)

the methods comprising contacting a compound of formula (8):

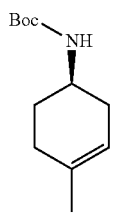
(8)

with a hydroborating agent followed by treatment with an oxidant, in the presence of a base, in a solvent.

In one embodiment, the hydroborating agent is $BH_3$/THF, $B_2H_6$, 9-BBN, $BCl_3$/$Me_3SiH$, or (+)-diisopinocampheylborane. In one embodiment, the hydroborating agent is $BH_3$/THF. In one embodiment, the oxidant is $H_2O_2$ or oxone. In another, the oxidant is $H_2O_2$. In yet another embodiment, the base is NaOH. In another embodiment, the solvent is THF or EtOH. In another embodiment, the solvent is THF.

In some embodiments, the methods further comprise preparing a compound of formula (8):

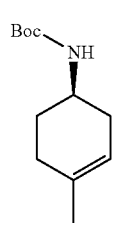
(8)

the methods comprising contacting a compound of formula (7):

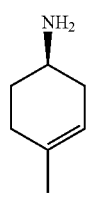
(7)

with Boc₂O in an organic solvent, optionally in the presence of a base. In one embodiment, the organic solvent is DCM or ether. In one embodiment, the base is triethylamine.

In some embodiments, the methods further comprise preparing a compound of formula (7):

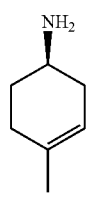
(7)

the methods comprising contacting a compound of formula (6):

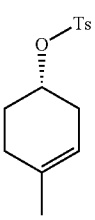
(6)

with an azidation agent in an organic solvent, followed by reducing the resulting azide derivative in an organic solvent.

In one embodiment, the azidation agent is NaN₃. In another, the reducing agent is LiAlH₄. In some embodiments, the solvent is selected from DMF, toluene, ACN, DCM, THF, or ether.

In some embodiments, the methods further comprise preparing a compound of formula (6):

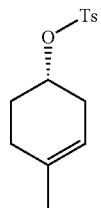
(6)

the methods comprising contacting a compound of formula (5):

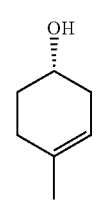
(5)

with tosyl chloride in an organic solvent, in the presence of a base.

In some embodiments, the organic solvent is selected from DMF, toluene, ACN, DCM, THF, or ether. In others, the base is triethylamine or pyridine.

In some embodiments, the methods further comprise preparing a compound of formula (5):

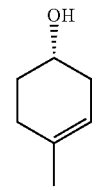
(5)

the methods comprising contacting a compound of formula (4):

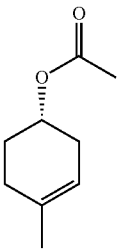
(4)

with a reducing agent in a solvent.

In some embodiments, the reducing agent is LiAlH₄. In others, the solvent is THF or ether.

In some embodiments, the methods further comprise preparing a compound of formula (4):

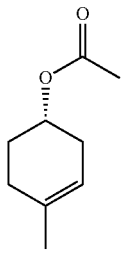
(4)

the methods comprising contacting a compound of formula (3):

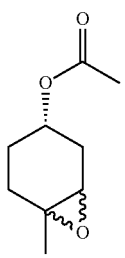
(3)

with Zn and NaI, in the presence of acetic acid.

In some embodiments, the methods further comprise preparing a compound of formula (3):

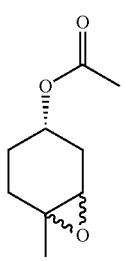
(3)

the methods comprising contacting a compound of formula (2):

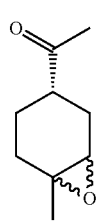
(2)

with a peracid in a solvent.

In some embodiments, the peracid is m-CPBA. In others, the solvent is DCM.

In some embodiments, the methods further comprise preparing a compound of formula (2):

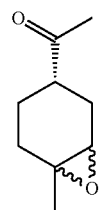
(2)

the methods comprising ozonolyzing a compound of formula (Y):

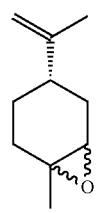
(Y)

in the presence of ozone.

In some embodiments, the methods further comprise preparing a compound of formula (Y):

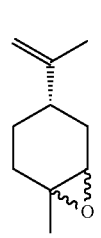
(Y)

the methods comprising contacting (−)-limonene having a formula:

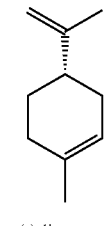

(−)-limonene with a peracid in a solvent.

In some embodiments, the peracid is m-CPBA. In others, the solvent is DCM.

In one aspect, provided herein are methods for preparing a compound of formula (A):

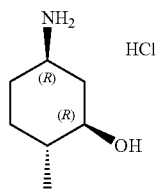

(A)

the methods comprising contacting a compound of formula (9a):

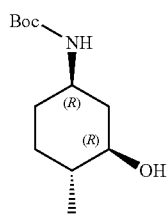

(9a)

with hydrochloric acid in a solvent.

In some embodiments, the solvent is 2-propanol, methanol, ether or dioxane.

In some embodiments, the methods further comprise preparing a compound of formula (9a):

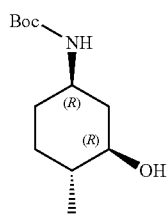

(9a)

the methods comprising separating a diastereomeric mixture of compounds of formulae (9a and 9b):

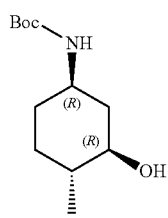

(9a)

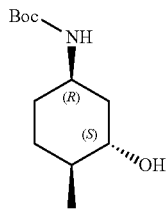

(9b)

by employing a chiral separation method.

In one embodiment, the chiral separation method is chiral supercritical fluid chromatography (SFC), chiral HPLC, chiral LC, recrystallization, or chiral resolution. In one embodiment, the chiral separation method is recrystallization in a solvent, and the solvent is MTBE.

In some embodiments, the methods further comprise preparing a diastereomeric mixture of compounds of formulae (9a and 9b):

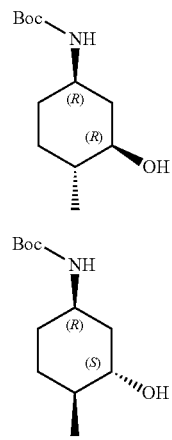

(9a)

(9b)

the methods comprising contacting a compound of formula (8):

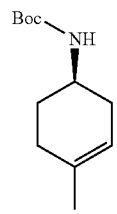

(8)

with a hydroborating agent, followed by treatment with an oxidant, in a solvent, in the presence of an aqueous base.

In one embodiment, the hydroborating agent is $BH_3/THF$, $B_2H_6$, 9-BBN, $BCl_3/Me_3SiH$, or (+)-diisopinocampheylborane. In one embodiment, the hydroborating agent is (+)-diisopinocampheylborane. In another embodiment, the solvent is THF or EtOH. In another, the solvent is THF. In some embodiments, the oxidant is $H_2O_2$ or oxone. In some embodiments, the oxidant is $H_2O_2$. In others, the base is NaOH.

In some embodiments, the methods further comprise preparing a compound of formula (8):

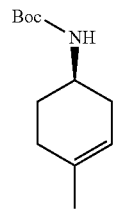

(8)

the methods comprising contacting a compound of formula (18):

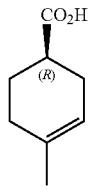
(18)

with diphenylphosphoryl azide in an organic solvent, in the presence of a base, followed by addition of t-butanol and CuCl.

In some embodiments, the organic solvent is toluene. In others, the base is triethylamine.

In some embodiments, the methods further comprise preparing a compound of formula (18):

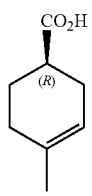
(18)

the methods comprising contacting a compound of formula (17):

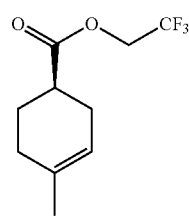
(17)

with an aqueous base, in a solvent.

In one embodiment, the base is LiOH or NaOH. In another, the solvent is MeOH.

In some embodiments, the methods further comprise preparing a compound of formula (17):

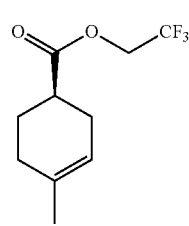
(17)

the methods comprising contacting a compound of formula (11):

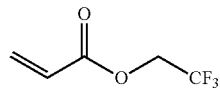
(11)

with a compound of formula (12):

(12)

in a solvent, in the presence of catalysts of formulae (15 and 16):

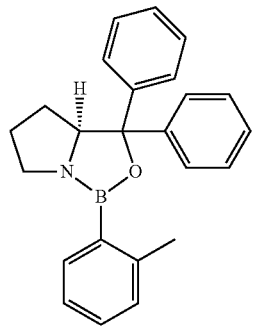
(15)

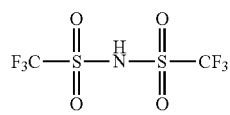
(16)

In one embodiment the amount of catalyst (16) used in the reaction is less than the amount of catalyst (15). In another, the load of catalyst (15) is between 5-20 mol %. In some embodiments, the solvent is toluene. In others, the contacting is performed at a temperature of about −20° C. to about 0° C. In yet another embodiment, the contacting is performed at a temperature of about −15° C.

In some embodiments, the methods further comprise preparing a compound of formula (15):

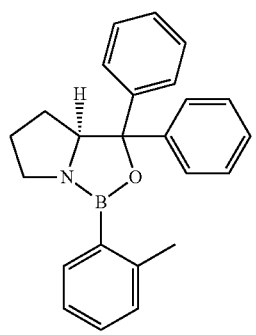
(15)

the methods comprising contacting a compound of formula (13):

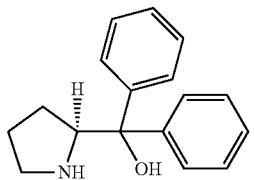

(13)

with a compound of formula (14):

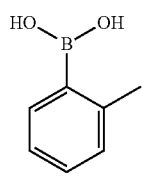

(14)

in a solvent.

In one embodiment, the solvent is toluene. In another, the contacting is performed at refluxing temperature.

In one aspect, provided herein are methods for preparing a compound of formula (A):

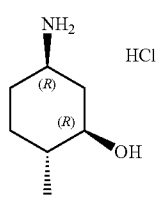

(A)

the methods comprising contacting a compound of formula (9a):

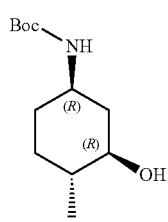

(9a)

with hydrochloric acid in a solvent.

In some embodiments, the solvent is 2-propanol, methanol, ether or dioxane.

In some embodiments, the methods further comprises preparing a compound of formula (9a):

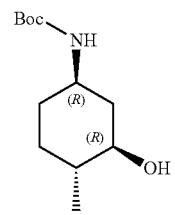

(9a)

the methods comprising separating a diastereomeric mixture of compounds of formulae (9a and 9b):

(9a)

(9b)

by employing a chiral separation method.

In one embodiment, the chiral separation method is chiral supercritical fluid chromatography (SFC), recrystallization, chiral HPLC, chiral LC, or chiral resolution. In one embodiment, the chiral separation method is recrystallization in a solvent. In one embodiment the recrystallization solvent is MTBE.

In some embodiments, the methods further comprise preparing a diastereomeric mixture of compounds of formulae (9a and 9b):

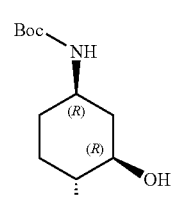

(9a)

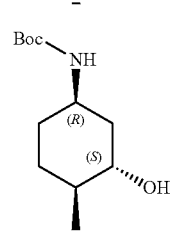

(9b)

the methods comprising contacting a compound of formula (8):

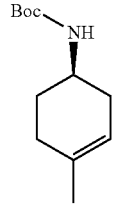
(8)

with a hydroborating agent, followed by treatment with an oxidant, in a solvent, in the presence of a base.

In one embodiment, the hydroborating agent is $BH_3/THF$, $B_2H_6$, 9-BBN, $BCl_3/Me_3SiH$, or (+)-diisopinocampheylborane. In one embodiment, the hydroborating agent is $B_2H_6$, 9-BBN, $BCl_3/Me_3SiH$, or (+)-diisopinocampheylborane. In another, the oxidant is $H_2O_2$ or oxone. In another embodiment, the solvent is THF or EtOH. In another embodiment, the solvent is THF. In yet another embodiment, the base is NaOH.

In some embodiments, the methods further comprise preparing a compound of formula (8):

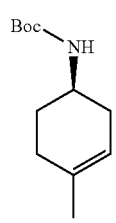
(8)

the methods comprising performing Curtius rearrangement of a compound of formula (18):

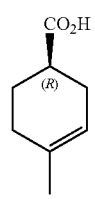
(18)

utilizing CDI, $NH_2OH$, and $^tBuOH$.

In some embodiments, the methods further comprise preparing a compound of formula (18):

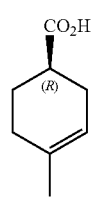
(18)

the methods comprising resolution of a compound of formula (20):

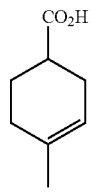
(20)

by employing a chiral amine.

In one embodiment, the chiral amine is (S)-phenylethanamine or (R)-phenylethanamine.

In some embodiments, the methods further comprise preparing a compound of formula (20):

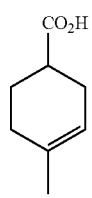
(20)

the methods comprising contacting a compound of formula (19):

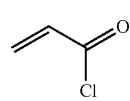
(19)

with a compound of formula (12):

(12)

followed by treatment with a base, followed by an acidic workup. In one embodiment, the base is NaOH. In another, the acidic workup is performed with $H_2SO_4$. In some embodiments, the contacting is performed at a temperature of about 25° C.

In one aspect, provided herein are methods for preparing a compound of formula (A):

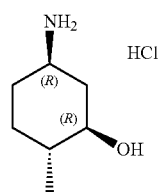
(A)

the methods comprising contacting a compound of formula (9a):

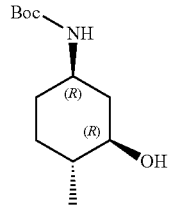
(9a)

with hydrochloric acid in a solvent.

In some embodiments, the solvent is 2-propanol, methanol, ether or dioxane.

In some embodiments, the methods further comprises preparing a compound of formula (9a):

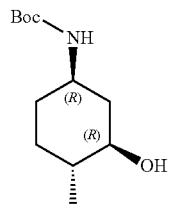
(9a)

the methods comprising separating a diastereomeric mixture of compounds of formulae (9a and 9b):

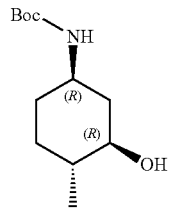
(9a)

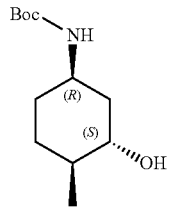
(9b)

by employing a chiral separation method.

In one embodiment, the chiral separation method is chiral supercritical fluid chromatography (SFC), recrystallization, chiral HPLC, chiral LC or chiral resolution. In one embodiment, the chiral separation method is recrystallization in a solvent. In one embodiment, the recrystallization solvent is MTBE.

In some embodiments, the methods further comprise preparing a diastereomeric mixture of compounds of formulae (9a and 9b):

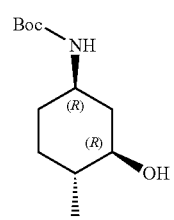
(9a)

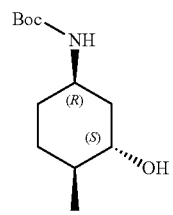
(9b)

the methods comprising contacting a compound of formula (8):

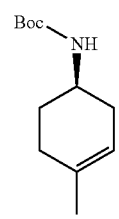
(8)

with a hydroborating agent, followed by treatment with an oxidant, in a solvent, in the presence of a base.

In one embodiment, the hydroborating agent is $BH_3$/THF, $B_2H_6$, 9-BBN, $BCl_3$/$Me_3$SiH, or (+)-diisopinocampheylborane. In one embodiment, the hydroborating agent is $B_2H_6$, 9-BBN, $BCl_3$/$Me_3$SiH, or (+)-diisopinocampheylborane. In another, the oxidant is $H_2O_2$ or oxone. In another embodiment, the solvent is THF or EtOH. In another embodiment, the solvent is THF. In yet another embodiment, the base is NaOH.

In some embodiments, the methods further comprise preparing a compound of formula (8):

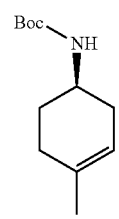
(8)

the methods comprising contacting a compound of formula (18):

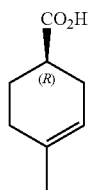
(18)

with diphenylphosphoryl azide in an organic solvent, in the presence of a base, followed by addition of t-butanol and CuCl.

In some embodiments, the organic solvent is toluene. In others, the base is triethylamine.

In some embodiments, the methods further comprise preparing a compound of formula (18):

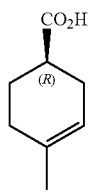
(18)

the methods comprising hydrolyzing a compound of formula (22):

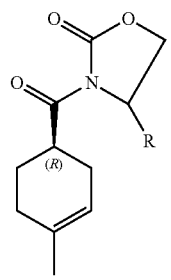
(22)

by treatment with a base and an oxidant.

In one embodiment, R is $^i$Pr or $CH_2$Ph. In one embodiment the base is LiOH. In another embodiment, the oxidant is $H_2O_2$.

In some embodiments, the methods further comprise preparing a compound of formula (22):

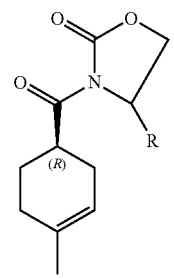
(22)

the methods comprising contacting a compound of formula (21):

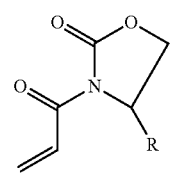
(21)

with a compound of formula (12):

(12)

under conditions suitable for a Diels Alder reaction.

In one aspect, provided herein are methods for preparing a compound of formula (A):

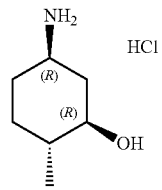
(A)

the methods comprising separating enantiomers of formulae (26a and 26b):

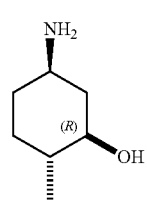
(26a)

-continued

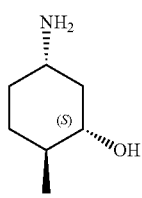
(26b)

by employing a chiral separation method.

In one embodiment, the chiral separation method is chiral supercritical fluid chromatography (SFC), recrystallization, chiral HPLC, chiral LC, or chiral resolution. In one embodiment, the chiral separation method is chiral supercritical fluid chromatography (SFC) or chiral resolution.

In some embodiments, the methods further comprise preparing a mixture of enantiomers of formulae (26a and 26b):

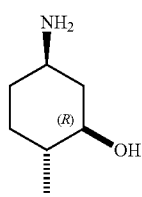
(26a)

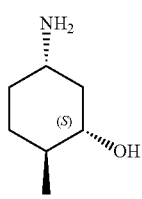
(26b)

the methods comprising contacting a mixture of enantiomers of formula (25a and 25b):

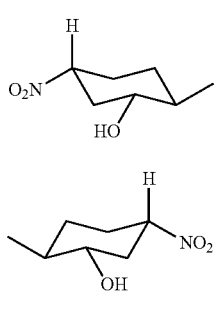
(25a)

(25b)

with a reducing agent.

In one embodiment, the reducing agent is hydrogen in the presence of Pd/C. In another, the reducing agent is Zn in EtOH in the presence of acetic acid.

In some embodiments, the methods further comprise preparing a mixture of enantiomers of formulae (25a and 25b):

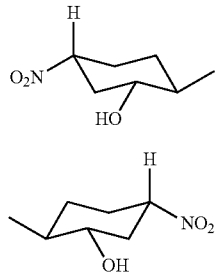
(25a)

(25b)

the methods comprising racemizing a mixture of four diastereomers of formulae (25a, 25b, 25c, and 25d):

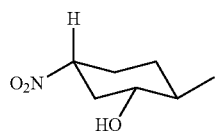
(25a)

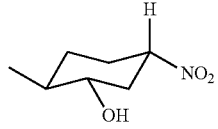
(25b)

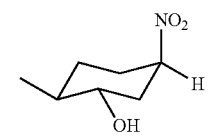
(25c)

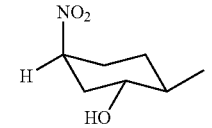
(25d)

by treatment with a base.

In some embodiments, the base is selected from NaOH, NaOEt, or tBuOK.

In some embodiments, the methods further comprise preparing a mixture of four diastereomers of formulae (25a, 25b, 25c, and 25d):

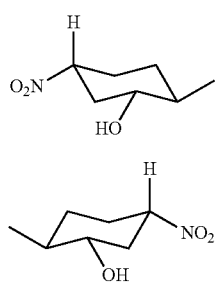
(25a)

(25b)

(25c)

-continued

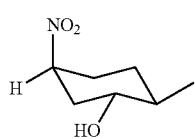
(25d)

the methods comprising contacting a compound of formula (24):

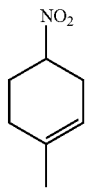
(24)

with a hydroborating agent, followed by treatment with an oxidant, in a solvent, in the presence of a base.

In one embodiment, the hydroborating agent is $BH_3$/THF, $B_2H_6$, 9-BBN, $BCl_3$/$Me_3SiH$, or (+)-diisopinocampheylborane. In one embodiment, the hydroborating agent is $BH_3$. In another, the oxidant is $H_2O_2$ or oxone. In another, the oxidant is $H_2O_2$. In another embodiment, the solvent is THF or EtOH. In another embodiment, the solvent is THF. In yet another embodiment, the base is NaOH.

In some embodiments, the methods further comprise preparing a compound of formula (24):

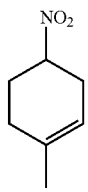
(24)

the methods comprising contacting a compound of formula (23):

(23)

with a compound of formula (12):

(12)

by under conditions suitable for a Diels-Alder reaction.

In one aspect, provided herein are methods for preparing a compound of formula (A):

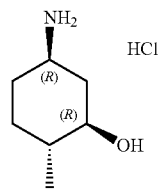
(A)

the methods comprising contacting a compound of formula (9a):

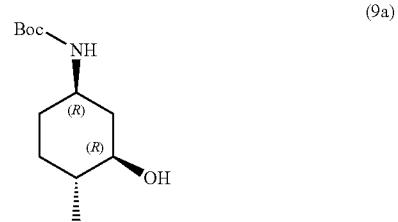
(9a)

with hydrochloric acid in a solvent.

In some embodiments, the solvent is 2-propanol, methanol, ether, or dioxane.

In some embodiments, the methods further comprise preparing a compound of formula (9a):

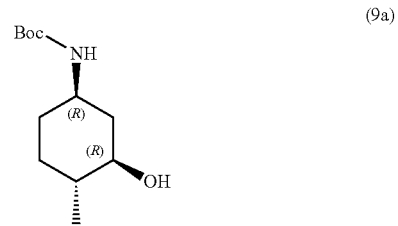
(9a)

the methods comprising separating a diastereomeric mixture of compounds of formulae (9a, 9b, 9c, and 9d):

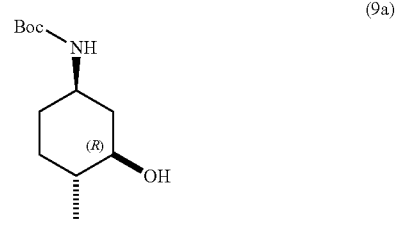
(9a)

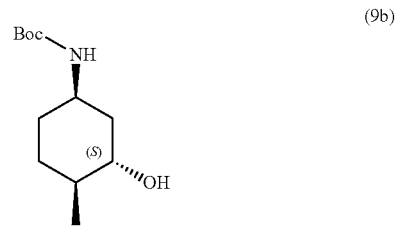
(9b)

-continued (9c)
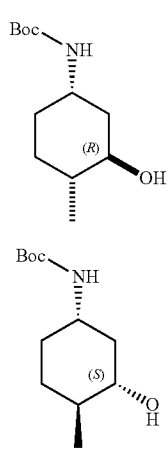

(9d)

by employing a chiral separation method.

In one embodiment, the chiral separation method is chiral supercritical fluid chromatography (SFC), recrystallization, chiral HPLC, chiral LC, or chiral resolution. In one embodiment, the chiral separation method is chiral supercritical fluid chromatography (SFC).

In some embodiments, the methods further comprise preparing a diastereomeric mixture of compounds of formulae (9a, 9b, 9c, and 9d):

(9a)

(9b)

(9c)

(9d)

the methods comprising contacting a compound of formula (32):

(32)
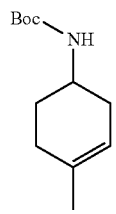

with a hydroborating agent, followed by treatment with an oxidant, in a solvent, in the presence of a base.

In one embodiment, the hydroborating agent is $BH_3$/THF, $B_2H_6$, 9-BBN, $BCl_3/Me_3SiH$, or (+)-diisopinocampheylborane. In one embodiment, the hydroborating agent is $BH_3$. In another embodiment, the solvent is THF or EtOH. In another, the solvent is THF. In another, the oxidant is $H_2O_2$ or oxone. In some embodiments, the oxidant is $H_2O_2$. In another, the base is NaOH. In yet another embodiment, the solvent is EtOH.

In some embodiments, the methods further comprise preparing a compound of formula (32):

(32)
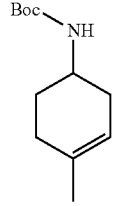

the methods comprising contacting a compound of formula (31):

(31)
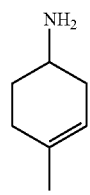

with $Boc_2O$ in a solvent, optionally in the presence of a base.

In one embodiment, the solvent is DCM. In another, the base is triethylamine.

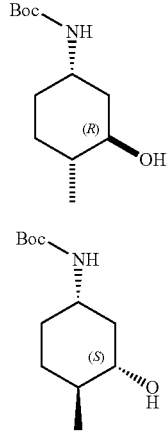

In some embodiments, the methods further comprise preparing a compound of formula (31):

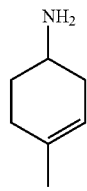
(31)

the methods comprising contacting a compound of formula (30):

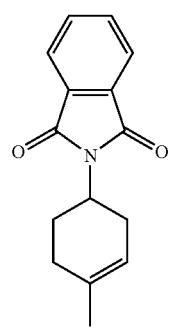
(30)

with hydrazine.

In some embodiments, the methods further comprise preparing a compound of formula (30):

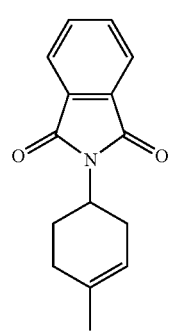
(30)

the methods comprising contacting a compound of formula (29):

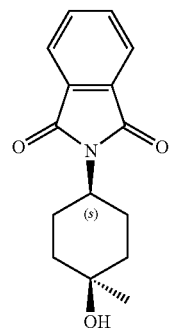
(29)

with a dehydrating agent.

In one embodiment, the dehydrating agent is $KHSO_4$ or $H_2SO_4$.

In some embodiments, the methods further comprise preparing a compound of formula (29):

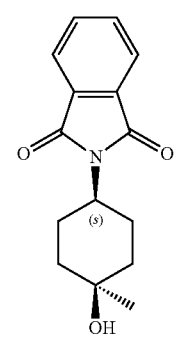
(29)

the methods comprising contacting a compound of formula (27):

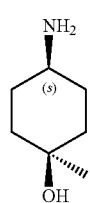
(27)

with a compound of formula (28):

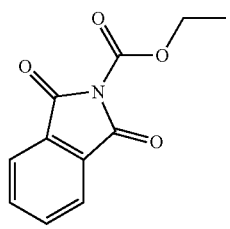
(28)

in the presence of a base.

In one embodiment, the base is K$_2$CO$_3$.

In one aspect, provided herein are methods for preparing a compound of formula (A):

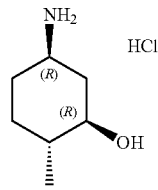
(A)

the methods comprising contacting a compound of formula (36):

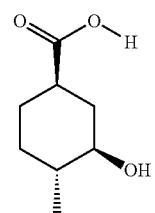
(36)

with diphenylphosphoryl azide in the presence of water.

In some embodiments, the methods further comprise preparing a compound of formula (36):

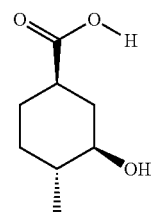
(36)

the methods comprising contacting a compound of formula (35):

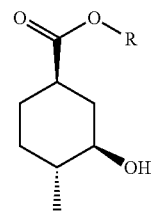
(35)

with a base,
wherein R=Me or iPr.

In some embodiments the base is NaOH.

In some embodiments, the methods further comprise preparing a compound of formula (35):

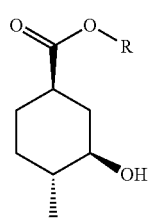
(35)

the methods comprising contacting a compound of formula (34):

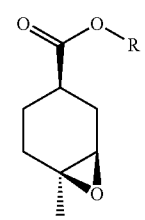
(34)

with Ti(OiPr)$_4$, Mg, and TMS-Cl,
wherein R=Me or iPr.

In some embodiments, the methods further comprise preparing a compound of formula (34):

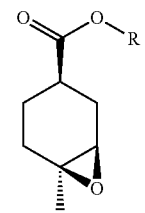
(34)

the methods comprising contacting a compound of formula (33):

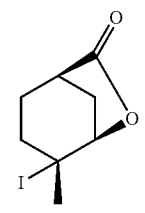
(33)

with an alkoxide.

In one embodiment the alkoxide is NaOMe or NaOiPr.

In some embodiments, the methods further comprise preparing a compound of formulae (33):

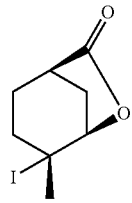

(33)

the methods comprising contacting a compound of formula (18):

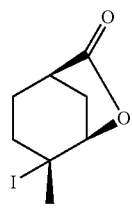

(33)

with KI₃ in the presence of NaHCO₃.

In one aspect, provided herein are methods for preparing a compound of formula (A):

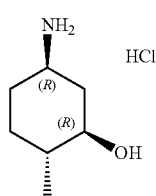

(A)

the methods comprising contacting a compound of formula (9a):

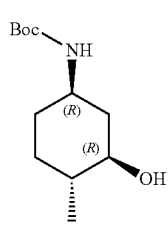

(9a)

with hydrochloric acid in a solvent.

In some embodiments, the solvent is 2-propanol, methanol, ether, or dioxane.

In some embodiments, the methods further comprise preparing a compound of formula (9a):

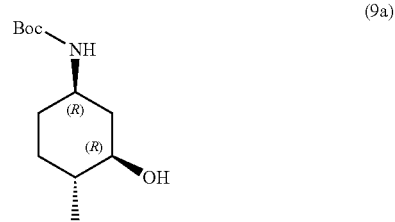

(9a)

the methods comprising separating a diastereomeric mixture of compounds of formula (40):

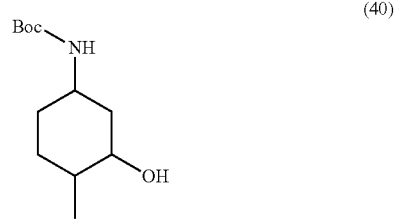 [SMILES: CC1CCC(NC(=O)OC(C)(C)C)CC1O]

(40)

by employing a chiral separation method.

In one embodiment, the chiral separation method is chiral supercritical fluid chromatography (SFC), recrystallization, chiral HPLC, chiral LC, or chiral resolution. In one embodiment, the chiral separation method is chiral supercritical fluid chromatography (SFC).

In some embodiments, the methods further comprise preparing a compound of formula (40):

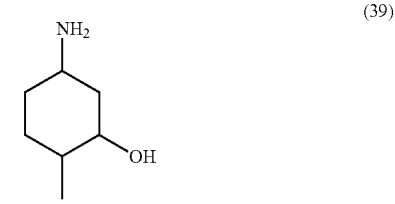

(40)

the methods comprising contacting a compound of formula (39):

(39)

with Boc₂O in a solvent, optionally in the presence of a base.

In one embodiment, the solvent is DCM. In another, the base is triethylamine.

In some embodiments, the methods further comprise preparing a compound of formula (39):

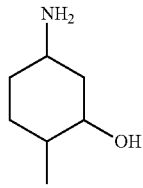
(39)

the methods comprising contacting a compound of formula (38):

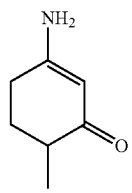
(38)

with a reducing agent.

In one embodiment, the reducing agent is NaBH$_4$.

In some embodiments, the methods further comprise preparing a compound of formula (38):

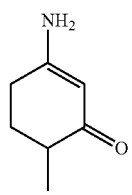
(38)

the methods comprising contacting a compound of formula (37):

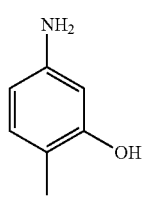
(37)

with hydrogen, in the presence of a catalyst.

In some embodiments, the catalyst is Pd/C or Pd(OH)$_2$/C.

In one aspect, provided herein are methods for preparing a compound of formula (A):

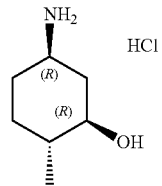
(A)

the methods comprising purifying a compound of formula (39):

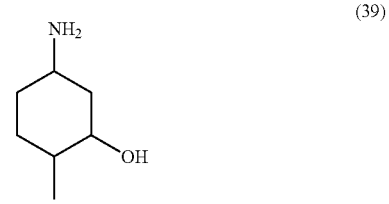
(39)

by employing a chiral separation method.

In one embodiment, the chiral separation method is chiral supercritical fluid chromatography (SFC), recrystallization, chiral HPLC, chiral LC, or chiral resolution. In one embodiment, the chiral separation method is chiral supercritical fluid chromatography (SFC).

In some embodiments, the methods further comprise preparing a compound of formula (39):

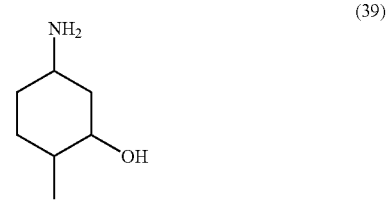
(39)

the methods comprising contacting a compound of formula (38):

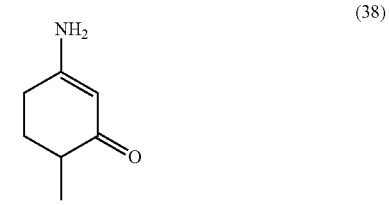
(38)

with a reducing agent.

In one embodiment, the reducing agent is NaBH$_4$.

In some embodiments, the methods further comprise preparing a compound of formula (38):

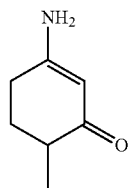
(38)

the methods comprising contacting a compound of formula (37):

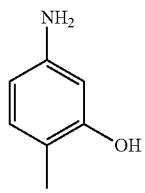
(37)

with hydrogen, in the presence of a catalyst.

In some embodiments, the catalyst is Pd/C or Pd(OH)$_2$/C.

In one aspect, provided herein are methods for preparing a compound of formula (A):

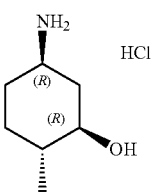
(A)

the methods comprising contacting a compound of formula (45a):

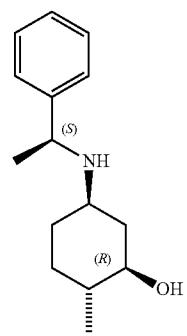
(45a)

with hydrogen, in the presence of a catalyst.

In some embodiments, the catalyst is Pd/C.

In some embodiments, the methods further comprise preparing a compound of formula (45a):

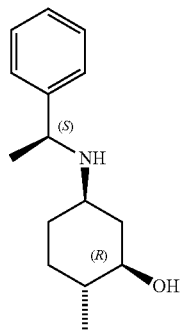
(45a)

the methods comprising separating diastereomers of a compound of formula (45):

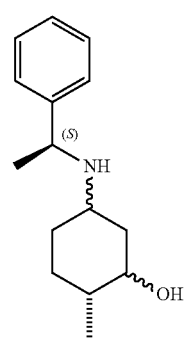
(45)

by employing a chiral separation method.

In one embodiment, the chiral separation method is chiral supercritical fluid chromatography (SFC), recrystallization, chiral HPLC, chiral LC, or chiral resolution. In one embodiment, the chiral separation method is chiral supercritical fluid chromatography (SFC).

In some embodiments, the methods further comprise preparing a compound of formula (45):

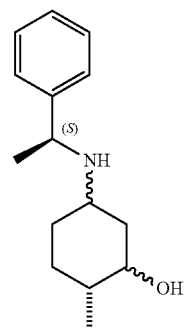
(45)

the methods comprising contacting a compound of formula (44a):

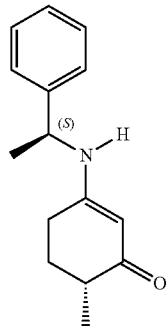
(44a)

with a reducing agent.

In one embodiment, the reducing agent is NaBH$_4$.

In some embodiments, the methods further comprise preparing a compound of formula (44a):

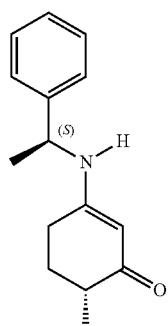
(44a)

the methods comprising separating a diastereomeric mixture of a compound of formula (44):

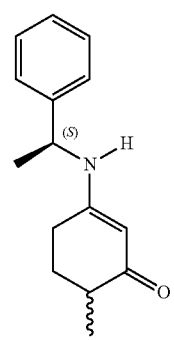
(44)

by employing resolution with a compound of formula:

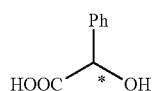

In some embodiments, the methods further comprise preparing a compound of formula (44):

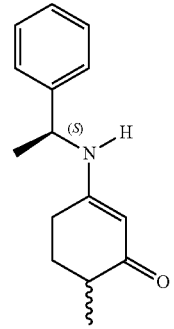
(44)

the methods comprising contacting a compound of formula (43):

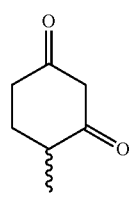
(43)

with a chiral amine.

In one embodiment, the chiral amine is (S)-phenylethanamine or (R)-phenylethanamine.

In some embodiments, the methods further comprise preparing a compound of formula (43):

(43)

the methods comprising contacting a compound of formula (42):

(42)

with a compound of formula (41):

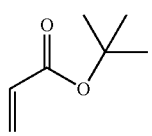
(41)

in the presence of a base.

In one embodiment, the base is KOtBu.

In one aspect, provided herein are methods for preparing a compound of formula (A):

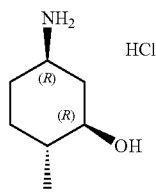
(A)

the methods comprising detosylating a compound of formula (52):

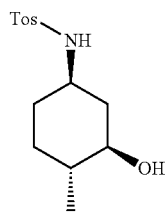
(52)

by treatment with a base and thiophenol.

In one embodiment, the base is K$_2$CO$_3$ or DBU.

In some embodiments, the methods further comprise preparing a compound of formula (52):

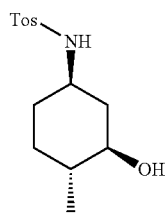
(52)

the methods comprising reducing asymmetrically a compound of formula (51):

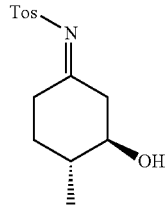
(51)

by treatment with Pd(CF$_3$CO$_2$)$_2$ and S-SegPhos under an atmosphere of hydrogen, in a solvent.

In one embodiment, the solvent is TFE.

In some embodiments, the methods further comprise preparing a compound of formula (51):

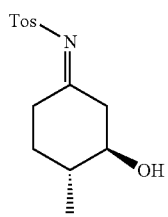
(51)

the methods comprising contacting a compound of formula (50):

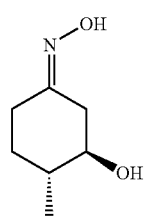
(50)

with TosCN in a solvent, in the presence of a base.

In some embodiments, the solvent is CCl$_4$. In others, the base is triethylamine. In some embodiments, the method is performed at a temperature of about −23° C.

In some embodiments, the methods further comprise preparing a compound of formula (50):

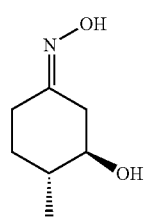
(50)

the methods comprising contacting a compound of formula (49):

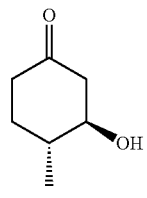
(49)

with NH$_4$Cl and Amberlyst A21, in a solvent.

In some embodiments, the solvent is ethanol.

In some embodiments, the methods further comprise preparing a compound of formula (49):

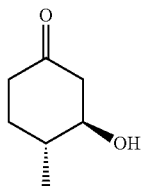

(49)

the methods comprising contacting a compound of formula (48a):

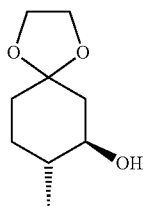

(48a)

with FeCl₃, in a solvent.

In some embodiments, the solvent is DCM.

In some embodiments, the methods further comprise purifying a compound of formula (48a):

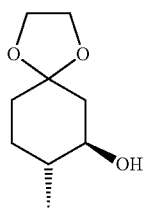

(48a)

the methods comprising separating a mixture of compounds of formulae (48a and 48b):

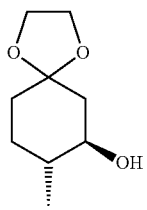

(48a)

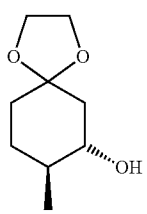

(48b)

by employing a chiral separation method.

In one embodiment, the chiral separation method is chiral supercritical fluid chromatography (SFC), recrystallization, chiral HPLC, chiral LC, or chiral resolution. In one embodiment, the chiral separation method is chiral supercritical fluid chromatography (SFC) or chiral resolution.

In some embodiments, the methods further comprise preparing a mixture of compounds of formulae (48a and 48b):

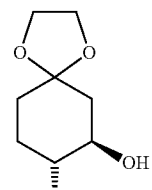

(48a)

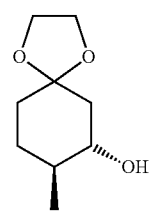

(48b)

the methods comprising contacting a compound of formula (47):

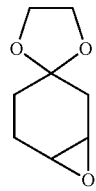

(47)

with MeLi, in the presence of AlMe₃, in a solvent.

In one embodiment, the solvent is heptanes.

In some embodiments, the methods further comprise preparing a compound of formula (47):

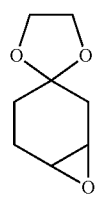

(47)

the methods comprising contacting a compound of formula (46):

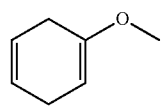

(46)

with catalytic amount of p-TsOH, in a solvent, followed by treatment with an oxidant.

In one embodiment, the oxidant is m-CPBA. In some embodiments, the solvent is DCM.

Solid Forms of Compound 1

In certain embodiments, provided herein are solid forms of Compound 1. In certain embodiments, the solid form is crystalline. In certain embodiments, the solid form is a single-component solid form. In certain embodiments, the solid form is a solvate.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The solid forms provided herein (e.g., Form A, Form B, Form C, Form D, Form E, Form F, Form G, Form H, Form I, and the amorphous solid of Compound 1) may be characterized using a number of methods known to a person skilled in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), dynamic vapor sorption (DVS), thermal gravimetric analysis (TGA), and hot-stage microscopy), spectroscopy (e.g., infrared, Raman, and solid-state nuclear magnetic resonance), ultra-high performance liquid chromatography (UHPLC), and proton nuclear magnetic resonance ($^1$H NMR) spectrum. The particle size and size distribution of the solid form provided herein may be determined by conventional methods, such as laser light scattering technique.

The purity of the solid forms provided herein may be determined by standard analytical methods, such as thin layer chromatography (TLC), gel electrophoresis, gas chromatography, ultra-high performance liquid chromatography (UHPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as ±0.2° 2θ (see United State Pharmacopoeia, page 2228 (2003)).

In certain embodiments, provided herein are methods for making a solid form of Compound 1, comprising 1) obtaining a slurry of Form A in a solvent; 2) stirring the slurry for a period of time (e.g., about 24 h) at a certain temperature (e.g., about 25° C. or about 50° C.); and 3) collecting solids from the slurry by filtration and optionally drying. In certain embodiments, provided herein are methods for making a solid form of Compound 1, comprising 1) obtaining a slurry of Form A in a solvent; 2) stirring the slurry for about 24 h at about 25° C. or about 50° C.; and 3) collecting solids from the slurry by filtration through 0.45 µm PTFE syring filters and optionally air drying. In certain embodiments, the methods for making a solid form of Compound 1 are equilibration experiments, such as slurry experiments.

In certain embodiments, provided herein are methods for making a solid form of Compound 1, comprising 1) dissolving Form A in a solvent to yield a solution; 2) filtering the solution if Form A does not dissolve completely; and 3) evaporating the solution under certain air pressure (e.g., about 1 atm) at a certain temperature (e.g., about 25° C. or about 50° C.) to yield a solid. In certain embodiments, provided herein are methods for making a solid form of Compound 1, comprising 1) dissolving Form A in a solvent to yield a solution; 2) filtering the solution through 0.45 µm PTFE syring filters if Form A does not dissolve completely; and 3) evaporating the solution under about 1 atm air pressure at about 25° C. or about 50° C. under nitrogen to yield a solid. In certain embodiments, the methods for making a solid form of Compound 1 are evaporation experiments.

In certain embodiments, provided herein are methods for making a solid form of Compound 1, comprising 1) obtaining a saturated solution of Form A in a solvent at a first temperature (e.g., about 60° C.); 2) stirring the solution at the first temperature for a period of time (e.g., 10 minutes); 3) filtering the solution; 4) cooling the solution slowly to a second temperature (e.g., about −5° C. to about 15° C.); and 5) isolating solids from the solution and optionally drying. In certain embodiments, provided herein are methods for making a solid form of Compound 1, comprising 1) obtaining a saturated solution of Form A in a solvent at about 60° C.; 2) stirring the solution at about 60° C. for 10 minutes; 3) filtering the solution through 0.45 µm PTFE syring filters; 4) cooling the solution slowly to about 5° C.; and 5) isolating solids from the solution and optionally air-drying. In certain embodiments, the methods for making a solid form of Compound 1 are cooling recrystallization experiments.

In certain embodiments, provided herein are methods for making a solid form of Compound 1, comprising 1) obtaining a saturated solution of Form A in a solvent at a first temperature (e.g., about 60° C.); 2) adding an anti-solvent into the saturated solution at the first temperature; 3) cooling down to a second temperature (e.g., about −5° C. to about 15° C.); and 4) collecting a solid if there is precipitation, and evaporating the solvent to collect a solid if there is no precipitation; and 5) optionally drying. In certain embodiments, provided herein are methods for making a solid form of Compound 1, comprising 1) obtaining a saturated solution of Form A in a solvent at about 60° C.; 2) adding an anti-solvent into the saturated solution at about 60° C.; 3) cooling down to about 5° C.; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the methods for making a solid form of Compound 1 are anti-solvent recrystallization experiments.

In certain embodiments, the solvent is acetone, DCM, EtOAc, EtOH, EtOH/H$_2$O (about 1:1), H$_2$O, heptane, IPA, ACN, ACN/H$_2$O (about 1:1), MEK, MeOH, MTBE, n-BuOH, THF, THF/H$_2$O (about 1:1), toluene or sulfolane.

In certain embodiments, the anti-solvent is ACN, heptane, MTBE, or water.

Form A

In certain embodiments, provided herein is Form A.

In one embodiment, Form A is a solid form of Compound 1. In one embodiment, Form A is a non-stoichiometric channel hydrate solid form of Compound 1. In another embodiment, Form A is crystalline.

In certain embodiments, Form A provided herein is obtained by equilibration experiments, evaporation experiments and anti-solvent recrystallization experiments (see Table 1, Table 2 and Table 3). In certain embodiments, Form A is obtained from certain solvent systems including MTBE, heptane, water, EtOH/H$_2$O (about 1:1), MeOH with water as anti-solvent, EtOH with water as anti-solvent, EtOH with MTBE as anti-solvent, and IPA with heptane as anti-solvent.

In one embodiment, a method of preparing Form A comprises the steps of 1) mixing Form H with a solvent (e.g., DMSO) mixture containing water (e.g., at least about 70% by volume of water); 2) stirring at a temperature (e.g., from about 20° C. to about 25° C., such as about 22° C.) for a period of time (e.g., from about 1 hour to about 6 hours, such as about 3 hours); and 3) collecting solids and optionally drying.

In one embodiment, a method of preparing Form A comprises the steps of 1) mixing Form H with a solvent (e.g., DMSO) mixture containing water (e.g., at least about 50% by volume of water); 2) heating to a temperature (e.g., from between about 60° C. to about 100° C., such as about 60° C. or about 70° C.) for a period of time (e.g., from about 1 hour to about 6 hours, such as about 3 hours); 3) cooling to a second temperature (e.g., from between about 10° C. to about 40° C., such as about 25° C.); and 4) collecting solids and optionally drying.

In one embodiment, a method of preparing Form A comprises the steps of 1) mixing Form H with a solvent (e.g., DMSO) mixture containing water (e.g., at least about 70% by volume of water); 2) heating the resulting mixture to a first temperature (e.g., from between about 60° C. to about 100° C., such as about 60° C. or about 70° C.) for a period of time (e.g., from about 1 hour to about 6 hours, such as 3 hours); 3) cooling the mixture to a second temperature (e.g., from between about 10° C. to about 40° C., such as about 25° C.); and 4) collecting solids and optionally drying.

In another embodiment, a method of preparing Form A comprises the steps of 1) mixing Form H with a solvent (e.g., DMSO) mixture containing at least about 70% by volume of water; 2) heating the resulting mixture to a temperature (e.g., from between about 60° C. to about 100° C., such as about 60° C. or about 70° C.) for from about 1 hour to about 6 hours, such as about 3 hours; 3) cooling the mixture to a temperature (e.g., from between about 10° C. to about 40° C., such as about 25° C.); and 4) collecting solids and optionally drying.

In certain embodiments, a solid form provided herein, e.g., Form A, is substantially crystalline, as indicated by, e.g., X-ray powder diffraction measurements. In one embodiment, Form A has an X-ray powder diffraction pattern substantially as shown in FIG. 1. In one embodiment, Form A has one or more characteristic X-ray powder diffraction peaks at approximately 9.74, 10.55, 11.86, 12.98, 13.61, 15.90, 16.41, 17.20, 17.85, 18.04, 18.54, 19.29, 19.56, 19.84, 20.19, 21.37, 21.83, 22.90, 23.46, 23.84, 24.36, 24.88, 25.29, 26.14, 26.92, 27.83, 28.30, 28.69, 29.21, 30.50, 31.63, 32.11, 32.63, 33.17, 34.32, 34.74, 36.00, 36.56, 36.95, 37.26, 37.61, 38.40, 39.07, 39.34 or 39.64° 2θ as depicted in FIG. 1. In a specific embodiment, Form A has one, two, three, four, five, six, seven or eight characteristic X-ray powder diffraction peaks at approximately 10.55, 13.61, 17.20, 17.85, 18.04, 19.84, 22.90 or 24.36° 2θ. In another embodiment, Form A has one, two, three or four characteristic X-ray powder diffraction peaks at approximately 10.55, 13.61, 17.20 or 19.84° 2θ. In another embodiment, Form A has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four or forty-five characteristic X-ray powder diffraction peaks as set forth in Table 8.

Figure 2:
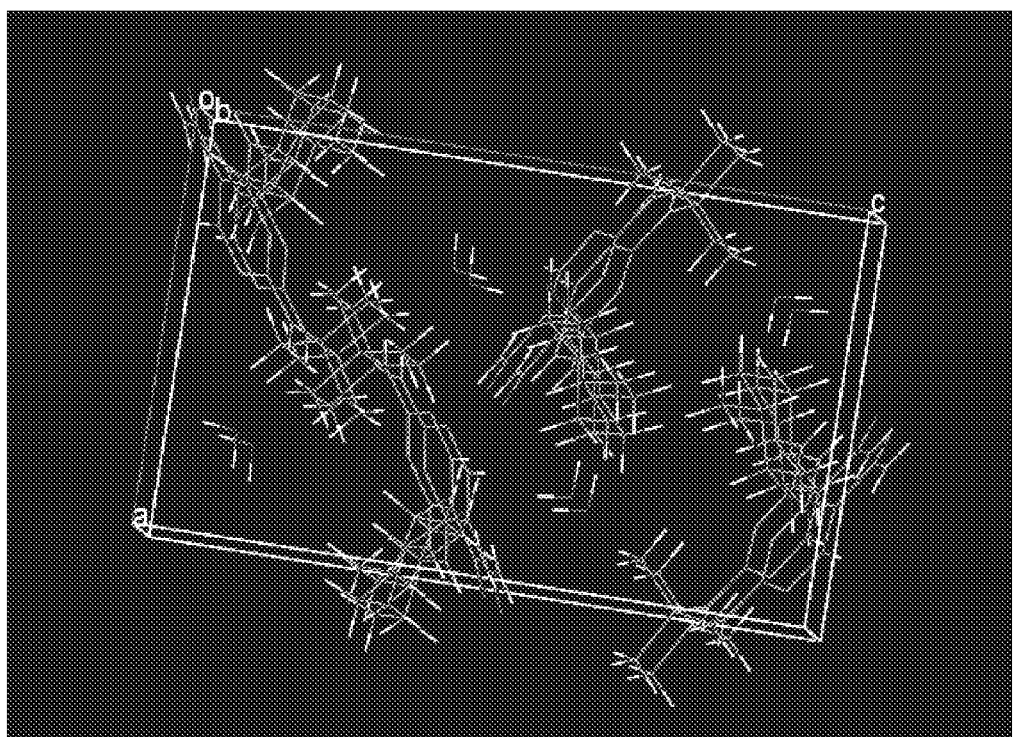
FIG. 2 depicts a crystal packing pattern and H-bond scheme of Form A.

Table 7 presents a summary of the crystallographic data from a single-crystal structure determination. In one embodiment, Form A has a crystal packing pattern substantially as shown in FIG. 2. In one embodiment, Form A is a solid form crystallizing in the space group P2(1)2(1)2(1). In one embodiment, Form A is a non-stoichiometric channel hydrate.

Figure 3:
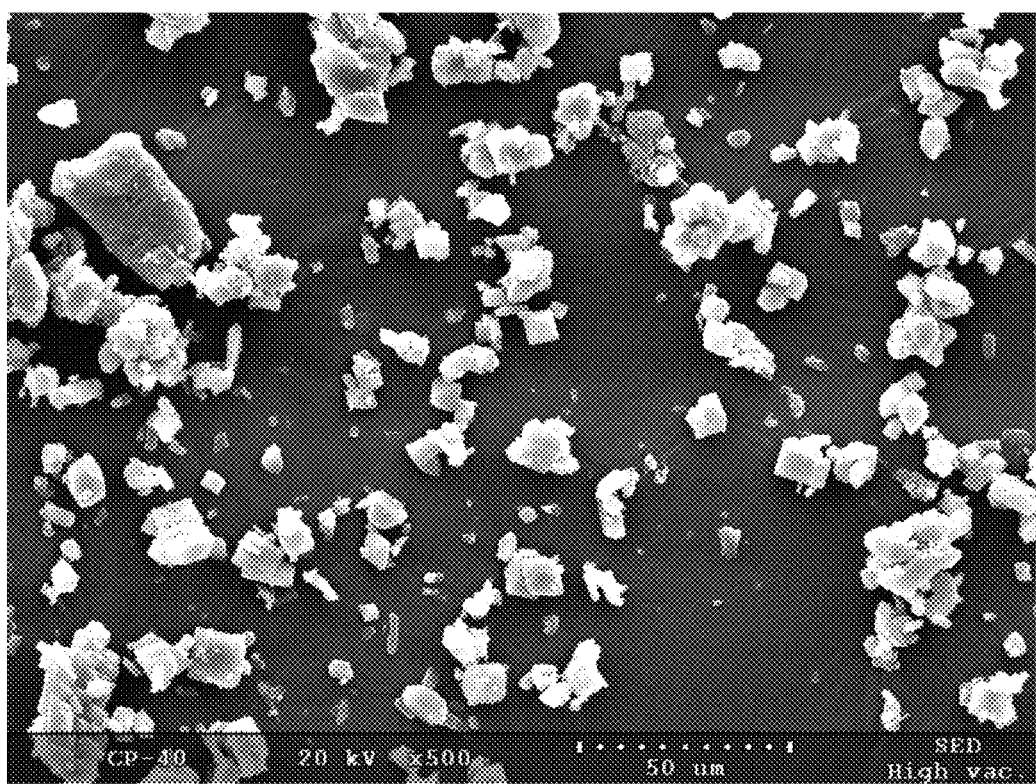
FIG. 3 depicts a scanning electron microscope (SEM) image of Form A.

In one embodiment, Form A has a SEM image substantially as shown in FIG. 3.

Figure 4:
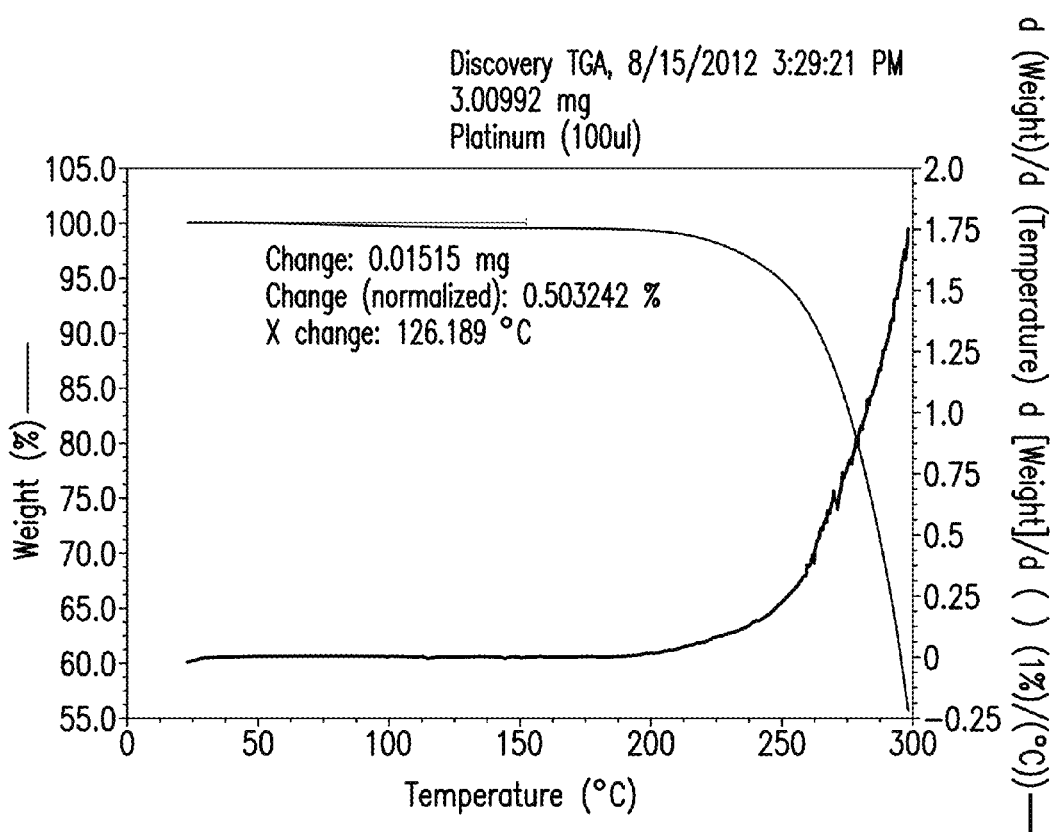
FIG. 4 depicts a thermogravimetrical analysis (TGA) thermogram of Form A.

In one embodiment, provided herein is Form A having a TGA thermograph corresponding substantially to the representative TGA thermogram as depicted in FIG. 4. In certain embodiments, the crystalline form exhibits a TGA thermogram comprising a total mass loss of approximately 0.45% of the total mass of the sample between approximately 30° C. and approximately 150° C. when heated from approximately 20° C. to approximately 300° C. Thus, in certain embodiments, the crystalline form loses from about 0.1% to about 5%, for example, about 0.45% or about 3.3%, of its total mass when heated from about ambient temperature to about 300° C.

Figure 5:
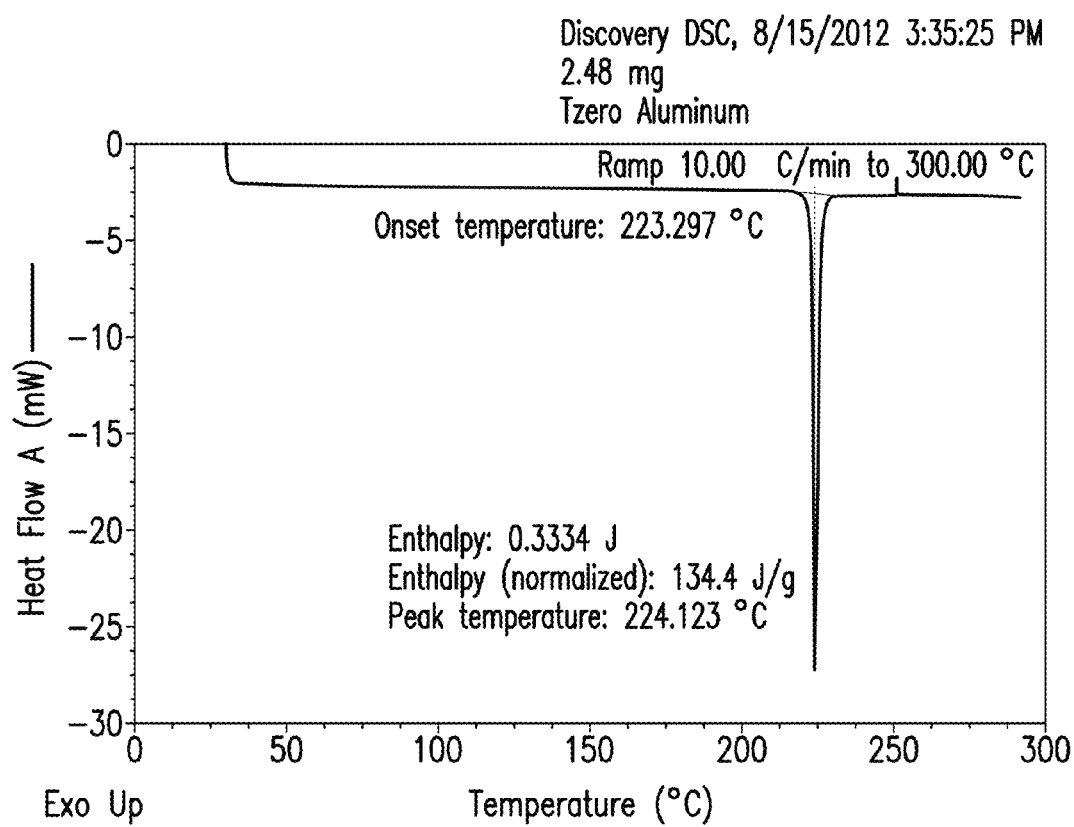
FIG. 5 depicts a differential scanning calorimetry (DSC) thermogram of Form A.

In one embodiment, provided herein is Form A having a DSC thermogram substantially as depicted in FIG. 5 comprising an endothermic event with an onset temperature of about 223° C. when heated from approximately 25° C. to approximately 300° C.

Figure 6:
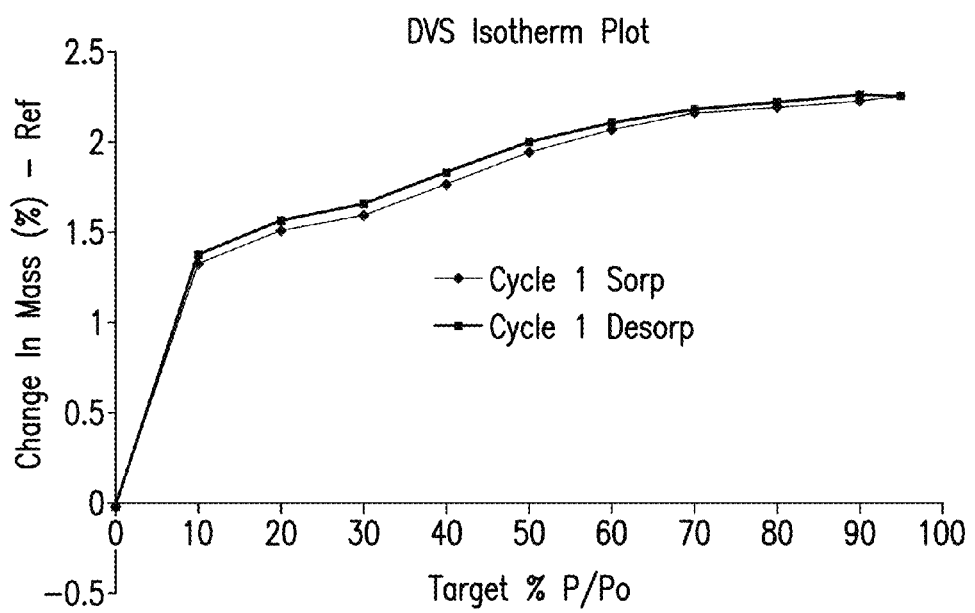
FIG. 6 depicts a dynamic vapor sorption (DVS) isotherm plot of Form A.

In one embodiment, provided herein is Form A having a DVS isotherm plot substantially as depicted in FIG. 6.

Figure 7:
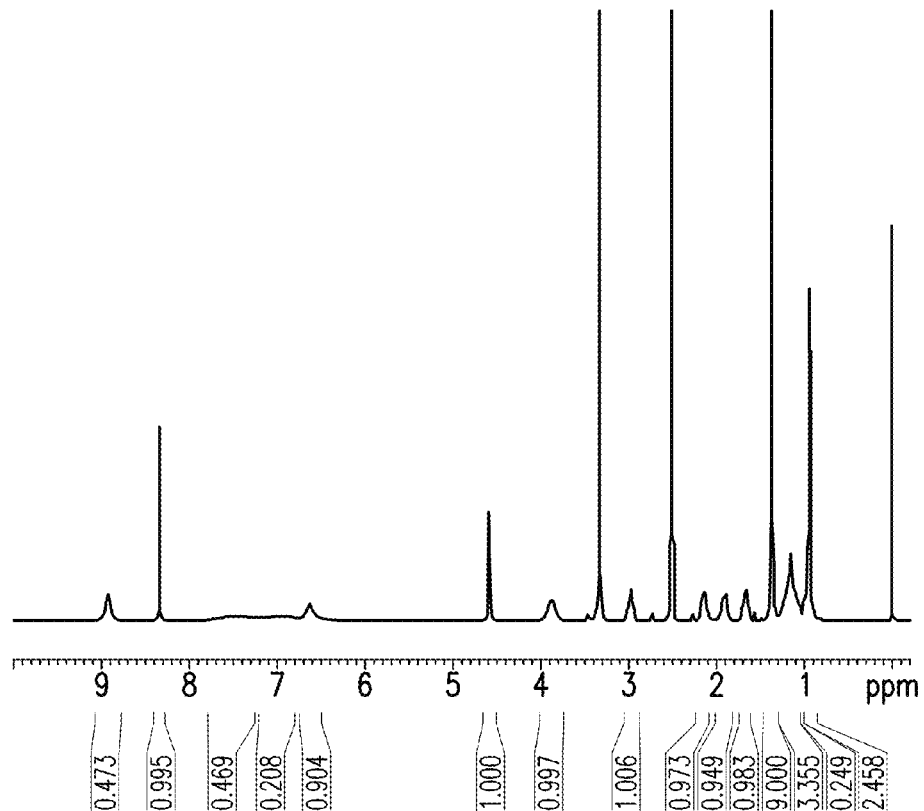
FIG. 7 depicts a $^1$H nuclear magnetic resonance (NMR) spectrum of Form A.

In one embodiment, provided herein is Form A having a $^1$H NMR spectrum substantially as depicted in FIG. 7.

In still another embodiment, Form A is substantially pure. In certain embodiments, the substantially pure Form A is substantially free of other solid forms, e.g., amorphous solid. In certain embodiments, the purity of the substantially pure Form A is no less than about 95%, no less than about 96%, no less than about 97%, no less than about 98%, no less than about 98.5%, no less than about 99%, no less than about 99.5%, or no less than about 99.8%.

Form B

In certain embodiments, provided herein is Form B.

In one embodiment, Form B is a solid form of Compound 1. In another embodiment, Form B is crystalline. In one embodiment, Form B is a solvated form of Compound 1. In one embodiment, Form B is an acetone solvated form of Compound 1. In one embodiment, Form B is an acetone hemi-solvated form of Compound 1.

In certain embodiments, Form B provided herein is obtained by equilibration experiments, evaporation experiments and anti-solvent recrystallization experiments (see Table 1, Table 2 and Table 3). In certain embodiments, Form B is obtained from certain solvent systems including acetone, MEK, DCM, THF, THF/H$_2$O (about 1:1), and IPA with heptane as anti-solvent.

Figure 10:
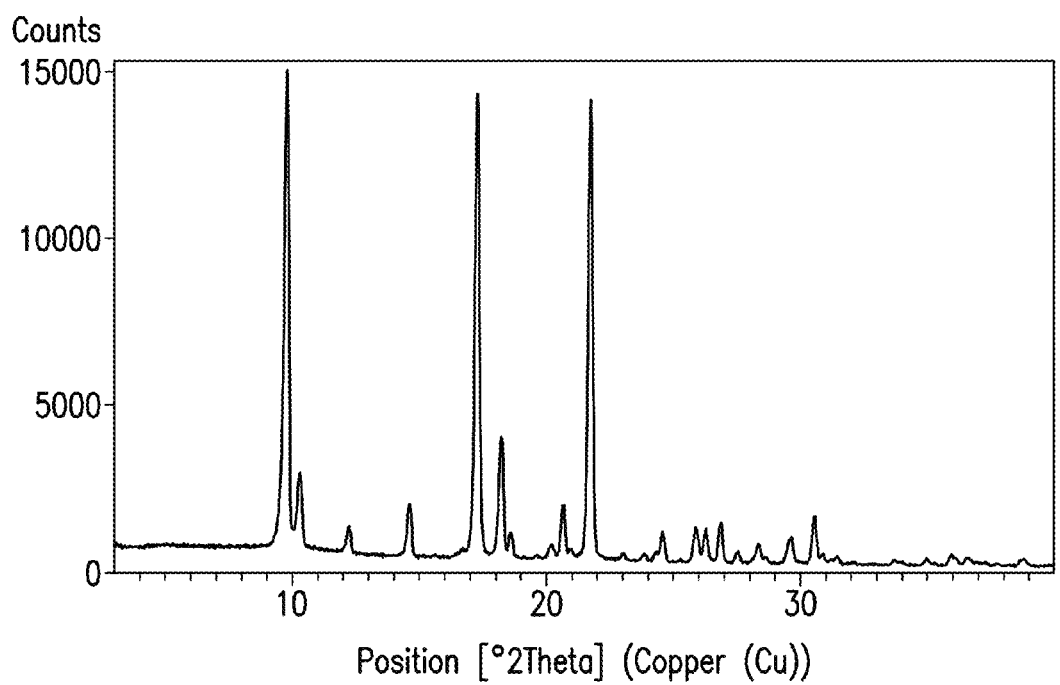
FIG. 10 depicts an XRPD pattern of Form B.

In certain embodiments, a solid form provided herein, e.g., Form B, is substantially crystalline, as indicated by, e.g., X-ray powder diffraction measurements. In one embodiment, Form B has an X-ray powder diffraction pattern substantially as shown in FIG. 10. In one embodiment, Form B has one or more characteristic X-ray powder diffraction peaks at approximately 9.80, 10.30, 12.23, 14.62, 16.70, 17.29, 18.23, 18.59, 19.61, 20.19, 20.66, 20.94, 21.74, 23.03, 23.84, 24.32, 24.58, 25.88, 26.27, 26.86, 27.52, 28.35, 28.62, 29.63, 30.55, 30.87, 31.44, 32.12, 33.71, 33.95, 34.96, 35.94, 36.14, 36.56, 37.22 or 38.76° 2θ as depicted in FIG. 10. In a specific embodiment, Form B has one, two, three, four, five, six, seven or eight characteristic X-ray powder diffraction peaks at approximately 9.80, 10.30, 14.62, 17.29, 18.23, 20.66, 21.74 or 30.55° 2θ. In another embodiment, Form B has one, two, three or four characteristic X-ray powder diffraction peaks at approximately 9.80, 17.29, 18.23 or 21.74° 2θ. In another embodiment, Form B has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five or thirty-six characteristic X-ray powder diffraction peaks as set forth in Table 9.

Figure 11:
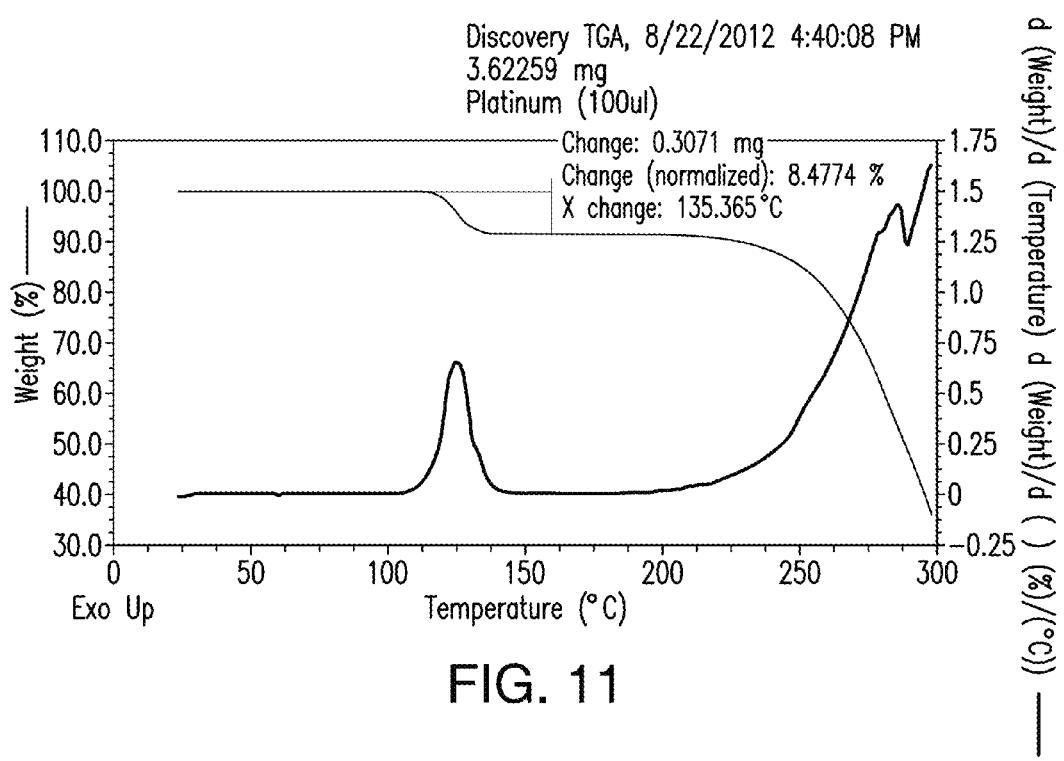
FIG. 11 depicts a TGA thermogram of Form B.

In one embodiment, provided herein is a crystalline form of Compound 1 having a TGA thermograph corresponding substantially to the representative TGA thermogram as depicted in FIG. 11. In certain embodiments, the crystalline form exhibits a TGA thermogram comprising a total mass loss of approximately 8.5% of the total mass of the sample between approximately 75° C. and approximately 175° C. when heated from approximately 25° C. to approximately 300° C. Thus, in certain embodiments, the crystalline form loses about 8.5% of its total mass when heated from about ambient temperature to about 300° C. In certain embodiments, the crystalline form contains 0.5 molar equivalents of solvent in the crystal lattice corresponding to approximately 0.5 mole of acetone per mole of Compound 1. The theoretical acetone content of an acetone hemi-solvate of Compound 1 is 8.3% by weight, matching the TGA weight loss observed. In certain embodiments, the crystalline form is an acetone hemi-solvate of Compound 1.

Figure 12:
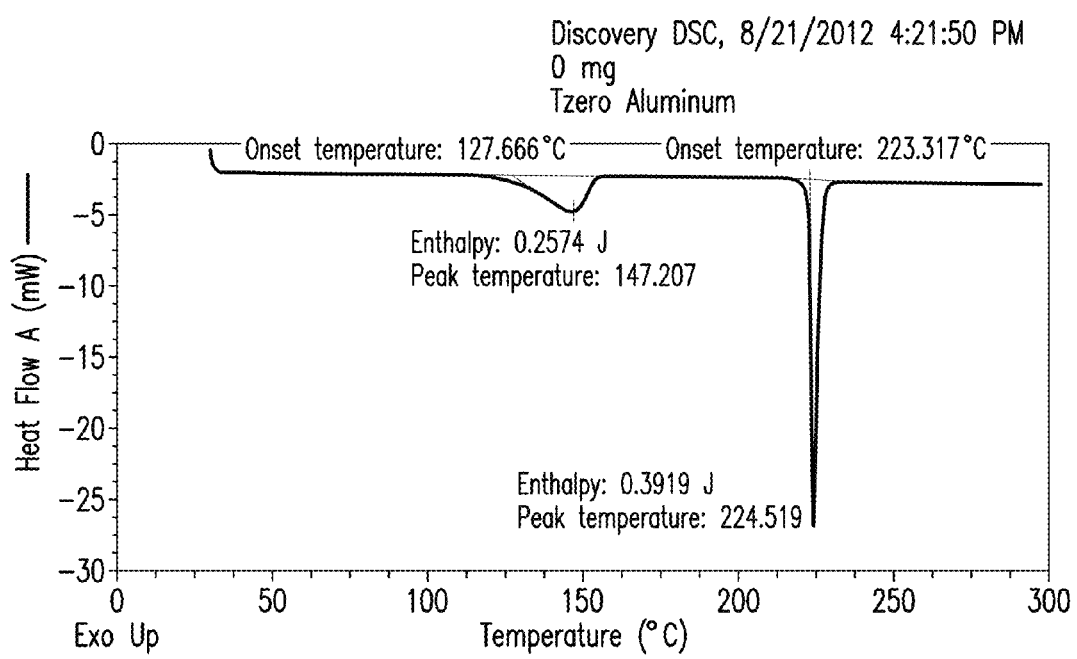
FIG. 12 depicts a DSC thermogram of Form B.

In one embodiment, provided herein is a crystalline form of Compound 1 having a DSC thermogram as depicted in FIG. 12 comprising an endothermic event with a maximum at about 147° C. when heated from approximately 25° C. to approximately 300° C.

In one embodiment, provided herein is a crystalline form of Compound 1 having a DSC thermogram as depicted in FIG. 12 comprising an endothermic event with an onset temperature of about 223° C. when heated from approximately 25° C. to approximately 300° C.

Figure 13:
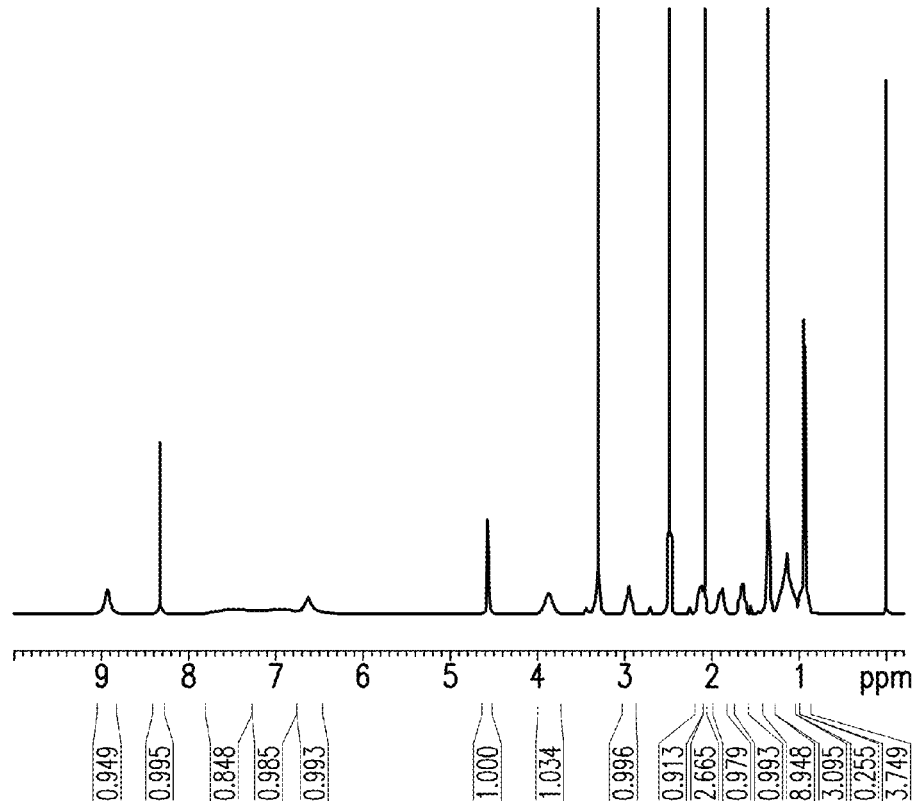
FIG. 13 depicts a $^1$H NMR spectrum of Form B.

In one embodiment, provided herein is Form B having a $^1$H NMR spectrum substantially as depicted in FIG. 13.

In still another embodiment, Form B is substantially pure. In certain embodiments, the substantially pure Form B is substantially free of other solid forms, e.g., amorphous solid. In certain embodiments, the purity of the substantially pure Form B is no less than about 95%, no less than about 96%, no less than about 97%, no less than about 98%, no less than about 98.5%, no less than about 99%, no less than about 99.5%, or no less than about 99.8%.

Form C

In certain embodiments, provided herein is Form C.

In one embodiment, Form C is a solid form of Compound 1. In another embodiment, Form C is crystalline. In one embodiment, Form C is a solvated form of Compound 1. In one embodiment, Form C is an ethanol solvated form of Compound 1. In one embodiment, Form C is an ethanol hemi-solvated form of Compound 1.

In certain embodiments, Form C provided herein is obtained by equilibration experiments, evaporation experiments, cooling recrystallization experiments and anti-solvent recrystallization experiments (see Table 1, Table 2 and Table 3). In certain embodiments, Form C is obtained from certain solvent systems including ACN, ACN/H$_2$O (about 1:1), EtOH, EtOH/H$_2$O (about 1:1), IPA, MEK, EtOH with MTBE as anti-solvent, EtOH with heptane as anti-solvent, EtOH with ACN as anti-solvent and IPA with heptane as anti-solvent.

Figure 14:
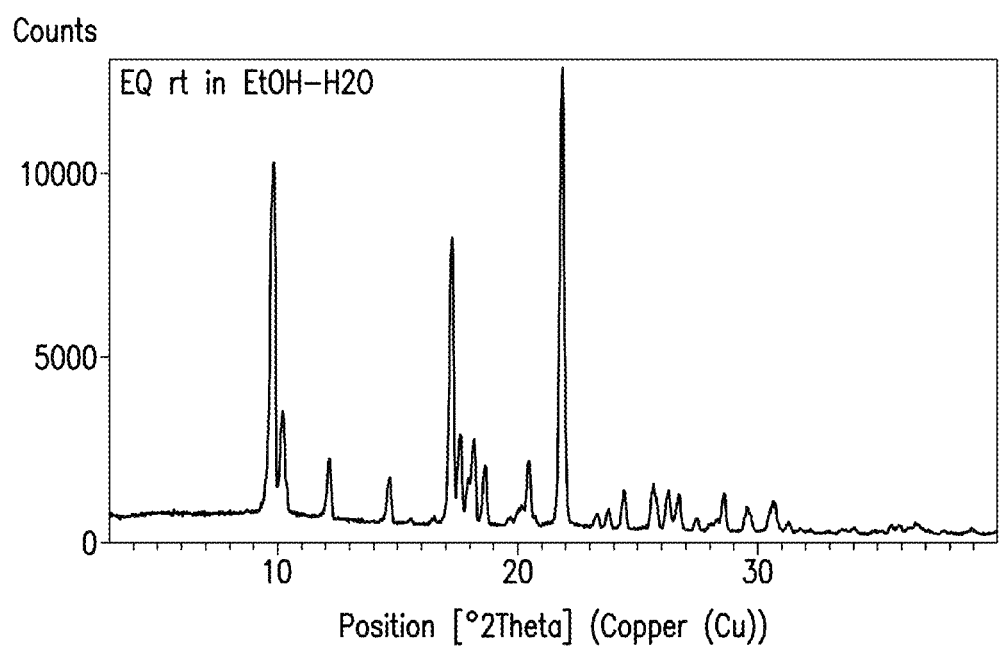
FIG. 14 depicts an XRPD pattern of Form C.

In certain embodiments, a solid form provided herein, e.g., Form C, is substantially crystalline, as indicated by, e.g., X-ray powder diffraction measurements. In one embodiment, Form C has an X-ray powder diffraction pattern substantially as shown in FIG. 14. In one embodiment, Form C has one or more characteristic X-ray powder diffraction peaks at approximately 9.83, 10.21, 12.16, 14.66, 15.52, 16.50, 17.26, 17.61, 17.91, 18.18, 18.65, 19.67, 19.99, 20.46, 21.86, 23.32, 23.78, 24.44, 25.65, 25.81, 26.28, 26.72, 27.46, 28.04, 28.30, 28.60, 29.56, 30.47, 30.70, 31.29, 31.77, 32.16, 32.94, 33.55, 34.00, 34.85, 35.14, 35.57, 35.90, 36.62, 37.76 or 38.93° 2θ as depicted in FIG. 14. In a specific embodiment, Form C has one, two, three, four, five, six, seven or eight characteristic X-ray powder diffraction peaks at approximately 9.83, 10.21, 12.16, 17.26, 17.61, 18.18, 20.46 or 21.86° 2θ. In another embodiment, Form C has one, two, three or four characteristic X-ray powder diffraction peaks at approximately 9.83, 10.21, 17.26 or 21.86° 2θ. In another embodiment, Form C has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one or forty-two characteristic X-ray powder diffraction peaks as set forth in Table 10.

Figure 15:
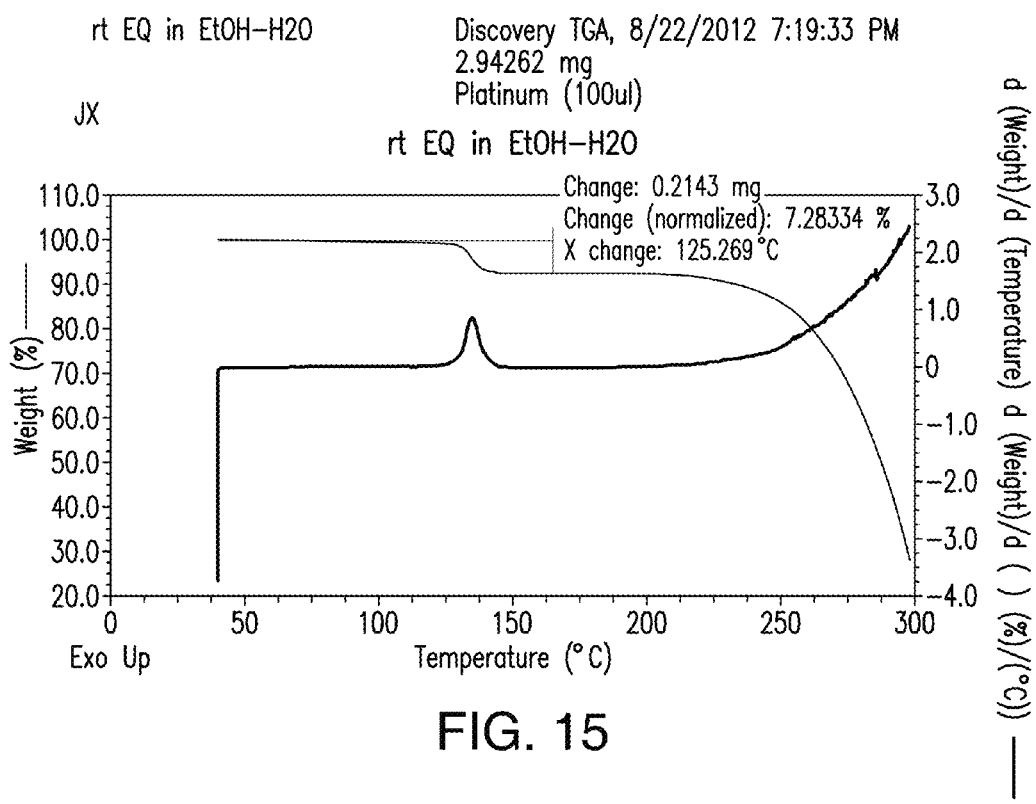
FIG. 15 depicts a TGA thermogram of Form C.

In one embodiment, provided herein is a crystalline form of Compound 1 having a TGA thermograph corresponding substantially to the representative TGA thermogram as depicted in FIG. 15. In certain embodiments, the crystalline form exhibits a TGA thermogram comprising a total mass loss of approximately 7.3% of the total mass of the sample between approximately 75° C. and approximately 175° C. when heated from approximately 25° C. to approximately 300° C. Thus, in certain embodiments, the crystalline form loses about 7.3% of its total mass when heated from about ambient temperature to about 300° C. In certain embodiments, the crystalline form contains 0.5 molar equivalents of solvent in the crystal lattice corresponding to approximately 0.5 mole of ethanol per mole of Compound 1. The theoretical ethanol content of an ethanol hemi-solvate of Compound 1 is 6.7% by weight, matching the TGA weight loss observed. In certain embodiments, the crystalline form is an ethanol hemi-solvate of Compound 1.

Figure 16:
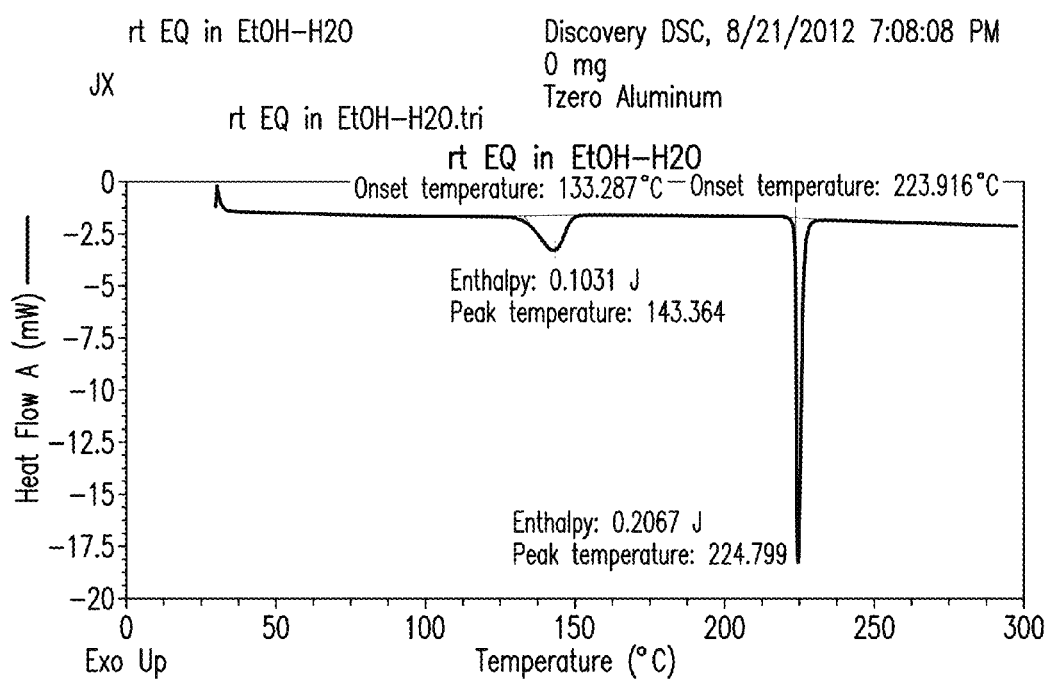
FIG. 16 depicts a DSC thermogram of Form C.

In one embodiment, provided herein is a crystalline form of Compound 1 having a DSC thermogram as depicted in FIG. 16 comprising an endothermic event with a maximum at about 143° C. when heated from approximately 25° C. to approximately 300° C.

In one embodiment, provided herein is a crystalline form of Compound 1 having a DSC thermogram as depicted in FIG. 16 comprising an endothermic event with an onset temperature of about 224° C. when heated from approximately 25° C. to approximately 300° C.

Figure 17:
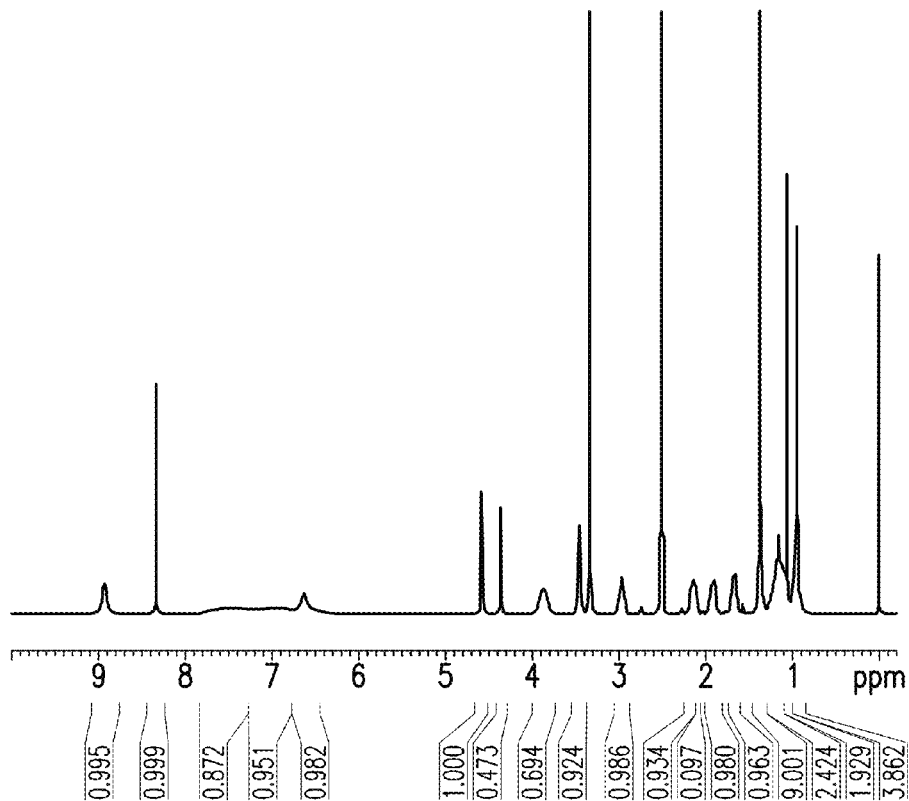
FIG. 17 depicts a $^1$H NMR spectrum of Form C.

In one embodiment, provided herein is Form C having a $^1$H NMR spectrum substantially as depicted in FIG. 17.

In still another embodiment, Form C is substantially pure. In certain embodiments, the substantially pure Form C is substantially free of other solid forms, e.g., amorphous solid. In certain embodiments, the purity of the substantially pure Form C is no less than about 95%, no less than about 96%, no less than about 97%, no less than about 98%, no less than about 98.5%, no less than about 99%, no less than about 99.5%, or no less than about 99.8%.

Form D

In certain embodiments, provided herein is Form D.

In one embodiment, Form D is a solid form of Compound 1. In another embodiment, Form D is crystalline. In one embodiment, Form D is a solvated form of Compound 1. In one embodiment, Form D is a methanol solvated form of Compound 1. In one embodiment, Form D is a methanol hemi-solvated form of Compound 1.

In certain embodiments, Form D provided herein is obtained by equilibration experiments, evaporation experiments, cooling recrystallization experiments and anti-solvent recrystallization experiments (see Table 1, Table 2 and Table 3). In certain embodiments, Form D is obtained from certain solvent systems including MeOH and MeOH with MTBE as anti-solvent.

Figure 18:
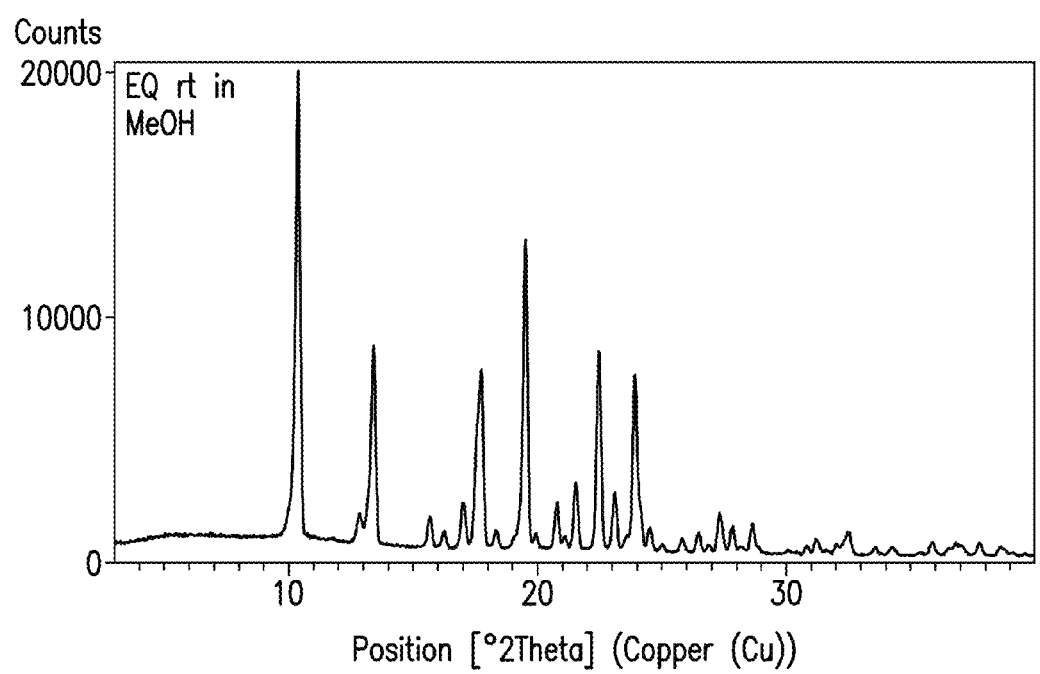
FIG. 18 depicts an XRPD pattern of Form D.

In certain embodiments, a solid form provided herein, e.g., Form D, is substantially crystalline, as indicated by, e.g., X-ray powder diffraction measurements. In one embodiment, Form D has an X-ray powder diffraction pattern substantially as shown in FIG. 18. In one embodiment, Form D has one or more characteristic X-ray powder diffraction peaks at approximately 10.37, 12.85, 13.41, 15.68, 16.25, 17.02, 17.54, 17.73, 18.34, 19.52, 19.93, 20.78, 21.09, 21.54, 22.47, 23.11, 23.55, 23.92, 24.51, 24.99, 25.81, 26.47, 26.88, 27.33, 27.83, 28.19, 28.64, 30.08, 30.82, 31.20, 31.60, 32.02, 32.50, 33.58, 34.25, 35.39, 35.87, 36.55, 36.81, 37.06, 37.77 or 38.60° 2θ as depicted in FIG. 18. In a specific embodiment, Form D has one, two, three, four, five, six, seven or eight characteristic X-ray powder diffraction peaks at approximately 10.37, 13.41, 17.54, 17.73, 19.52, 21.54, 22.47 or 23.92° 2θ. In another embodiment, Form D has one, two, three or four characteristic X-ray powder diffraction peaks at approximately 10.37, 13.41, 19.52 or 22.47° 2θ. In another embodiment, Form D has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two characteristic X-ray powder diffraction peaks as set forth in Table 11.

Figure 19:
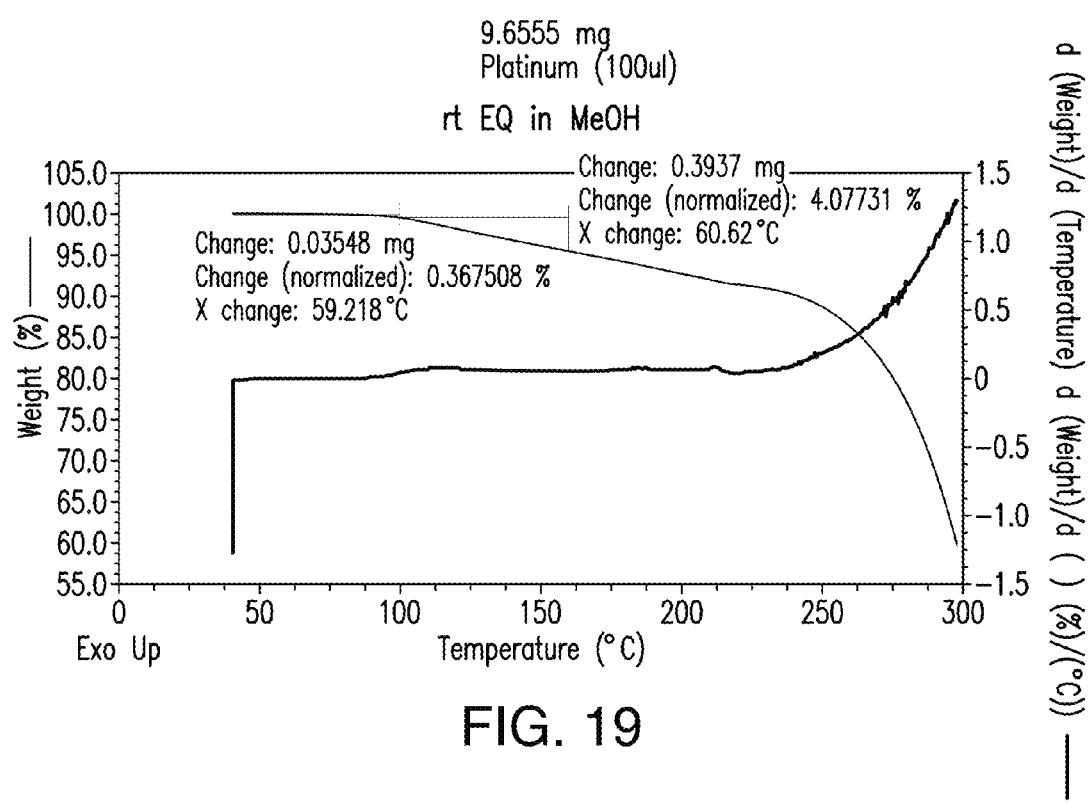
FIG. 19 depicts a TGA thermogram of Form D.

In one embodiment, provided herein is a crystalline form of Compound 1 having a TGA thermograph corresponding substantially to the representative TGA thermogram as depicted in FIG. 19. In certain embodiments, the crystalline form exhibits a TGA thermogram comprising a total mass loss of approximately 4% of the total mass of the sample between approximately 100° C. and approximately 160° C. when heated from approximately 25° C. to approximately 300° C. Thus, in certain embodiments, the crystalline form loses about 4% of its total mass when heated from about ambient temperature to about 300° C. In certain embodiments, the crystalline form contains 0.5 molar equivalents of solvent in the crystal lattice corresponding to approximately 0.5 mole of methanol per mole of Compound 1. The theoretical methanol content of a methanol hemi-solvate of Compound 1 is 4.7% by weight, matching the TGA weight loss observed. In certain embodiments, the crystalline form is a methanol hemi-solvate of Compound 1.

Figure 20:
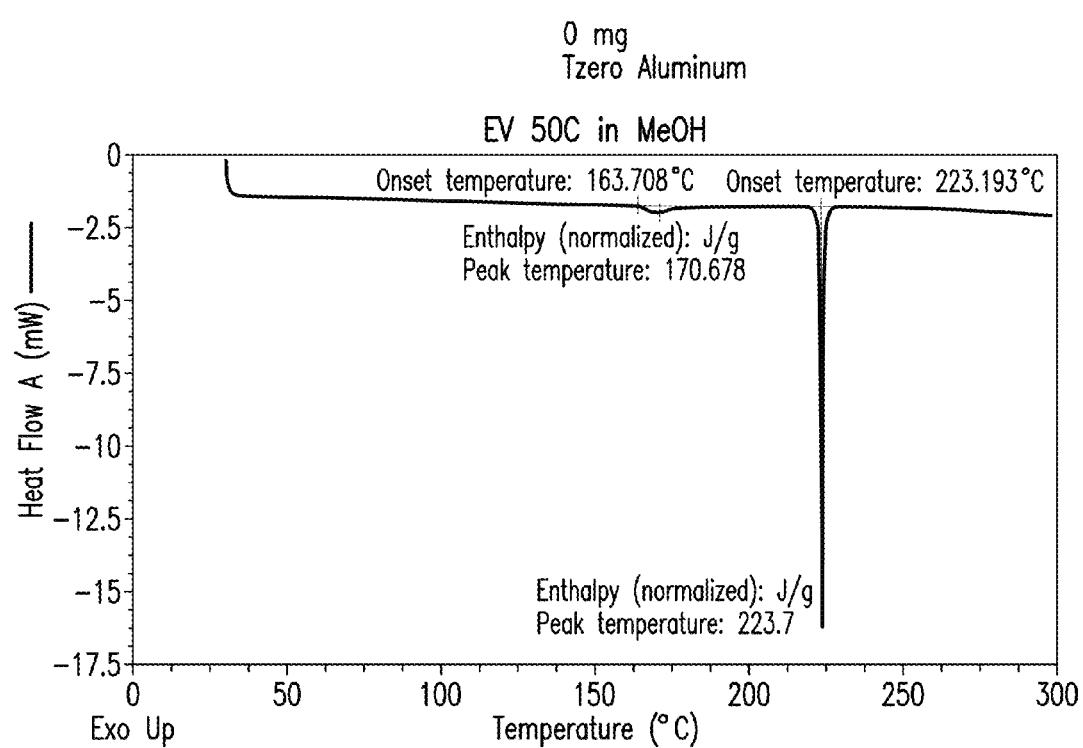
FIG. 20 depicts a DSC thermogram of Form D.

In one embodiment, provided herein is a crystalline form of Compound 1 having a DSC thermogram as depicted in FIG. 20 comprising an endothermic event with a maximum at about 170° C. when heated from approximately 25° C. to approximately 300° C.

In one embodiment, provided herein is a crystalline form of Compound 1 having a DSC thermogram as depicted in FIG. 20 comprising an endothermic event with an onset temperature of about 223° C. when heated from approximately 25° C. to approximately 300° C.

Figure 21:
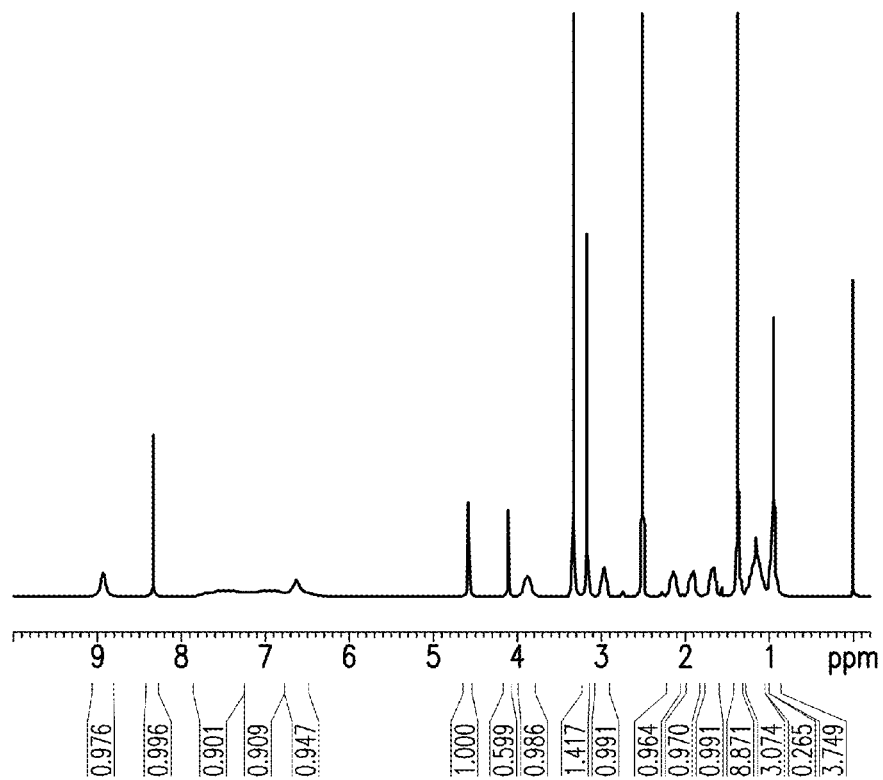
FIG. 21 depicts a $^1$H NMR spectrum of Form D.

In one embodiment, provided herein is Form D having a $^1$H NMR spectrum substantially as depicted in FIG. 21.

In still another embodiment, Form D is substantially pure. In certain embodiments, the substantially pure Form D is substantially free of other solid forms, e.g., amorphous solid. In certain embodiments, the purity of the substantially pure Form D is no less than about 95%, no less than about 96%, no less than about 97%, no less than about 98%, no less than about 98.5%, no less than about 99%, no less than about 99.5%, or no less than about 99.8%.

Form E

In certain embodiments, provided herein is Form E.

In one embodiment, Form E is a solid form of Compound 1. In another embodiment, Form E is crystalline. In one embodiment, Form E is a solvated form of Compound 1. In one embodiment, Form E is an n-butanol solvated form of Compound 1. In one embodiment, Form E is an n-butanol hemi-solvated form of Compound 1.

In certain embodiments, Form E provided herein is obtained by equilibration experiments and evaporation experiments (see Table 1 and Table 2). In certain embodiments, Form E is obtained from certain solvent systems including n-butanol.

Figure 22:
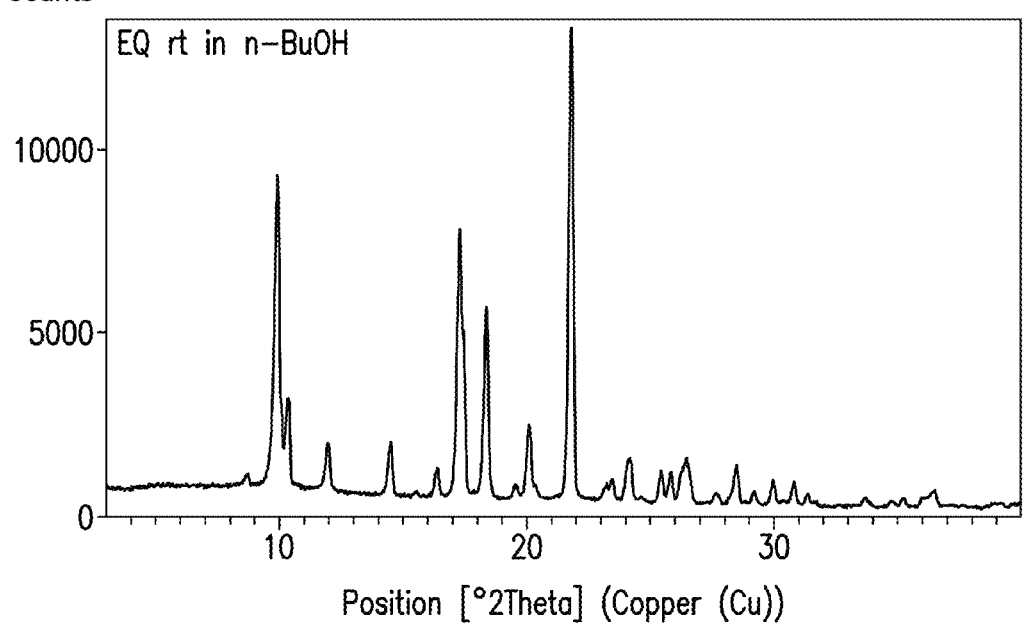
FIG. 22 depicts an XRPD pattern of Form E.

In certain embodiments, a solid form provided herein, e.g., Form E, is substantially crystalline, as indicated by, e.g., X-ray powder diffraction measurements. In one embodiment, Form E has an X-ray powder diffraction pattern substantially as shown in FIG. 22. In one embodiment, Form E has one or more characteristic X-ray powder diffraction peaks at approximately 8.70, 9.92, 10.36, 11.97, 14.50, 15.51, 16.39, 17.29, 18.37, 19.55, 20.10, 21.81, 23.21, 23.45, 24.17, 24.61, 25.44, 25.83, 26.23, 26.45, 26.61, 27.64, 28.48, 29.19, 29.97, 30.39, 30.81, 31.36, 31.66, 32.62, 33.67, 34.75, 35.24, 35.96, 36.48, 37.20, 37.62, 38.93 or 39.20° 2θ as depicted in FIG. 22. In a specific embodiment, Form E has one, two, three, four, five, six, seven or eight characteristic X-ray powder diffraction peaks at approximately 9.92, 10.36, 11.97, 14.50, 17.29, 18.37, 20.10 or 21.81° 2θ. In another embodiment, Form E has one, two, three or four characteristic X-ray powder diffraction peaks at approximately 9.92, 17.29, 18.37 or 21.81° 2θ. In another embodiment, Form E has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight or thirty-nine characteristic X-ray powder diffraction peaks as set forth in Table 12.

Figure 23:
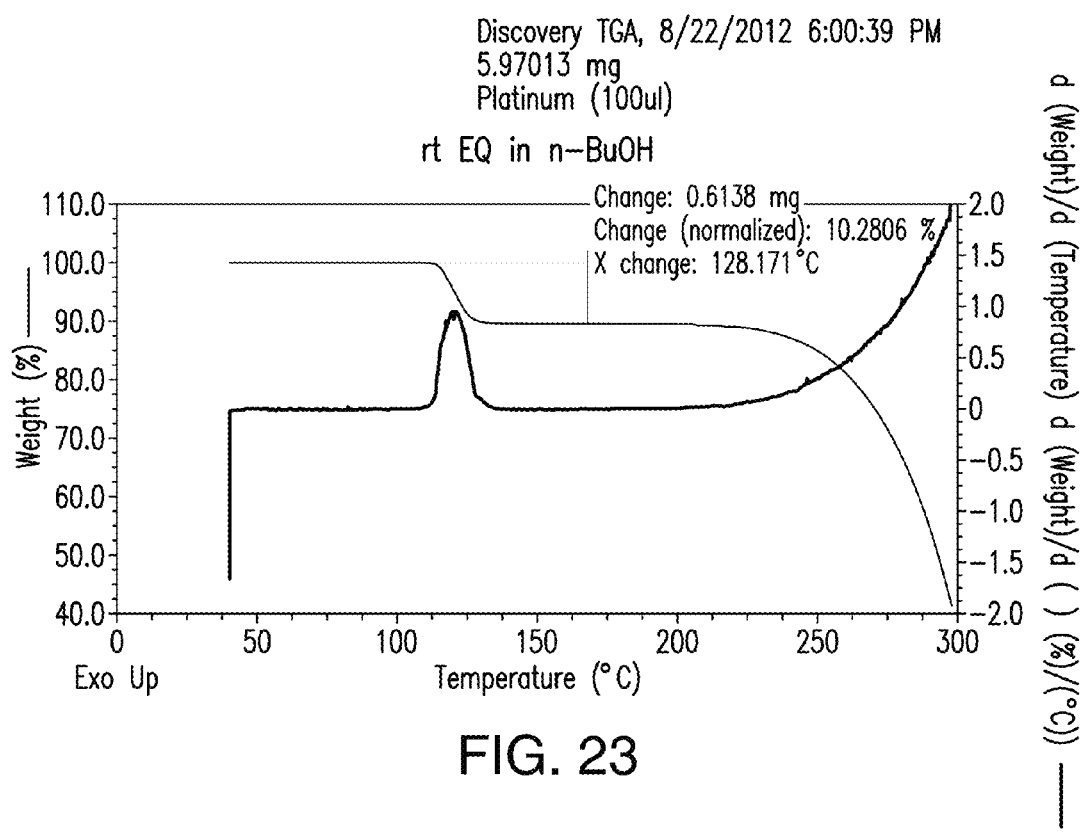
FIG. 23 depicts a TGA thermogram of Form E.

In one embodiment, provided herein is a crystalline form of Compound 1 having a TGA thermograph corresponding substantially to the representative TGA thermogram as depicted in FIG. 23. In certain embodiments, the crystalline form exhibits a TGA thermogram comprising a total mass loss of approximately 10.3% of the total mass of the sample between approximately 75° C. and approximately 175° C. when heated from approximately 25° C. to approximately 300° C. Thus, in certain embodiments, the crystalline form loses about 10.3% of its total mass when heated from about ambient temperature to about 300° C. In certain embodiments, the crystalline form contains 0.5 molar equivalents of solvent in the crystal lattice corresponding to approximately 0.5 mole of n-butanol per mole of Compound 1. The theoretical n-butanol content of an n-butanol hemi-solvate of Compound 1 is 10.3% by weight, matching the TGA weight loss observed. In certain embodiments, the crystalline form is an n-butanol hemi-solvate of Compound 1.

Figure 24:
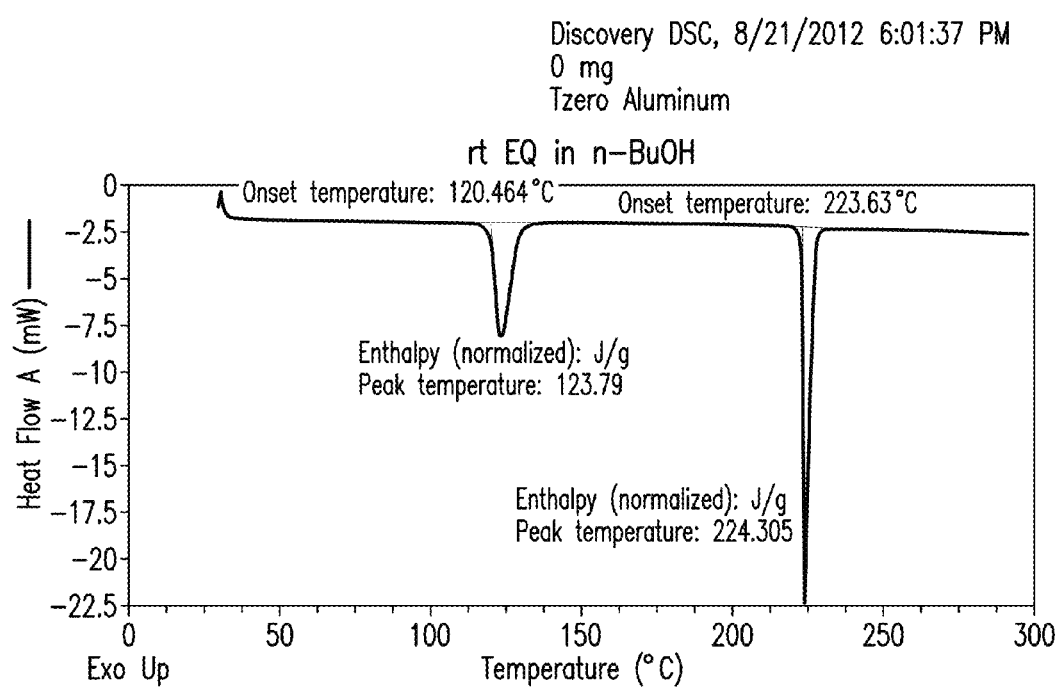
FIG. 24 depicts a DSC thermogram of Form E.

In one embodiment, provided herein is a crystalline form of Compound 1 having a DSC thermogram as depicted in FIG. 24 comprising an endothermic event with a maximum at about 124° C. when heated from approximately 25° C. to approximately 300° C.

In one embodiment, provided herein is a crystalline form of Compound 1 having a DSC thermogram as depicted in FIG. 24 comprising an endothermic event with an onset temperature of about 224° C. when heated from approximately 25° C. to approximately 300° C.

Figure 25:
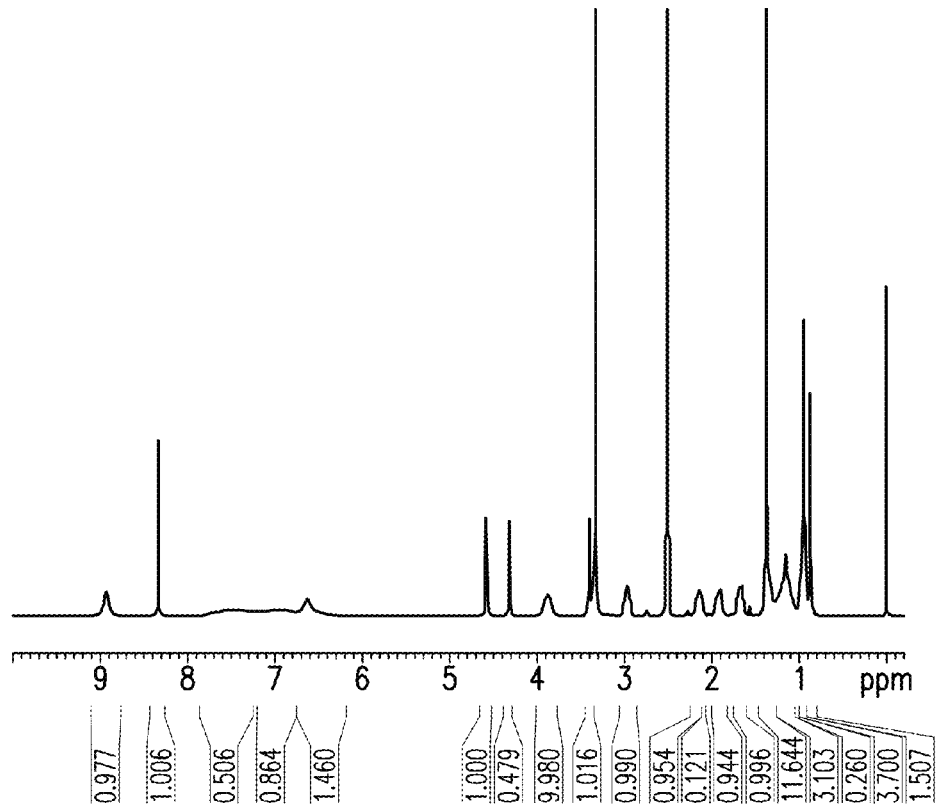
FIG. 25 depicts a $^1$H NMR spectrum of Form E.

In one embodiment, provided herein is Form E having a $^1$H NMR spectrum substantially as depicted in FIG. 25.

In still another embodiment, Form E is substantially pure. In certain embodiments, the substantially pure Form E is substantially free of other solid forms, e.g., amorphous solid. In certain embodiments, the purity of the substantially pure Form E is no less than about 95%, no less than about 96%, no less than about 97%, no less than about 98%, no less than about 98.5%, no less than about 99%, no less than about 99.5%, or no less than about 99.8%.

Form F

In certain embodiments, provided herein is Form F.

In one embodiment, Form F is a solid form of Compound 1. In another embodiment, Form F is crystalline. In one embodiment, Form F is a solvated form of Compound 1. In one embodiment, Form F is a toluene solvated form of Compound 1. In one embodiment, Form F is a 0.3 molar toluene solvated form of Compound 1.

In certain embodiments, Form F provided herein is obtained by equilibration experiments (see Table 1). In certain embodiments, Form F is obtained from certain solvent systems including toluene.

Figure 26:
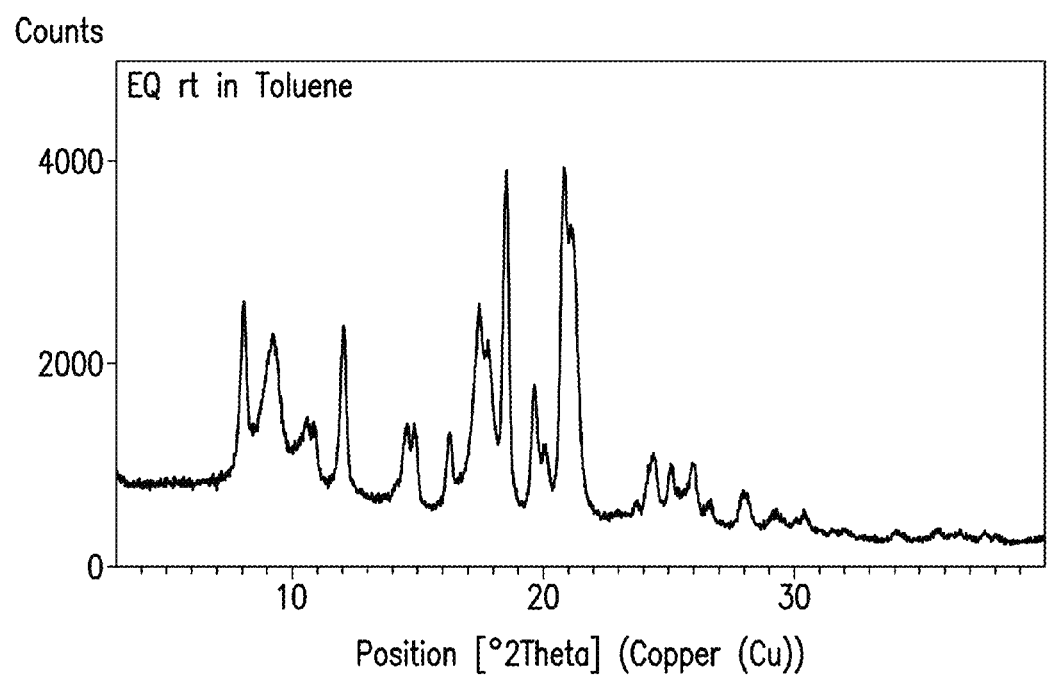
FIG. 26 depicts an XRPD pattern of Form F.

In certain embodiments, a solid form provided herein, e.g., Form F, is substantially crystalline, as indicated by, e.g., X-ray powder diffraction measurements. In one embodiment, Form F has an X-ray powder diffraction pattern substantially as shown in FIG. 26. In one embodiment, Form F has one or more characteristic X-ray powder diffraction peaks at approximately 8.07, 9.21, 10.58, 10.88, 12.06, 14.56, 14.87, 16.28, 17.45, 17.79, 18.53, 19.65, 20.05, 20.85, 21.10, 23.72, 24.41, 25.11, 25.98, 26.61, 27.94, 29.25, 30.40, 32.00, 34.06, 35.72, 36.58 or 37.59° 2θ as depicted in FIG. 26. In a specific embodiment, Form F has one, two, three, four, five, six, seven or eight characteristic X-ray powder diffraction peaks at approximately 8.07, 9.21, 12.06, 17.45, 17.79, 18.53, 20.85 or 21.10° 2θ. In another embodiment, Form F has one, two, three or four characteristic X-ray powder diffraction peaks at approximately 17.45, 18.53, 20.85 or 21.10° 2θ. In another embodiment, Form F has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven or twenty-eight characteristic X-ray powder diffraction peaks as set forth in Table 13.

Figure 27:
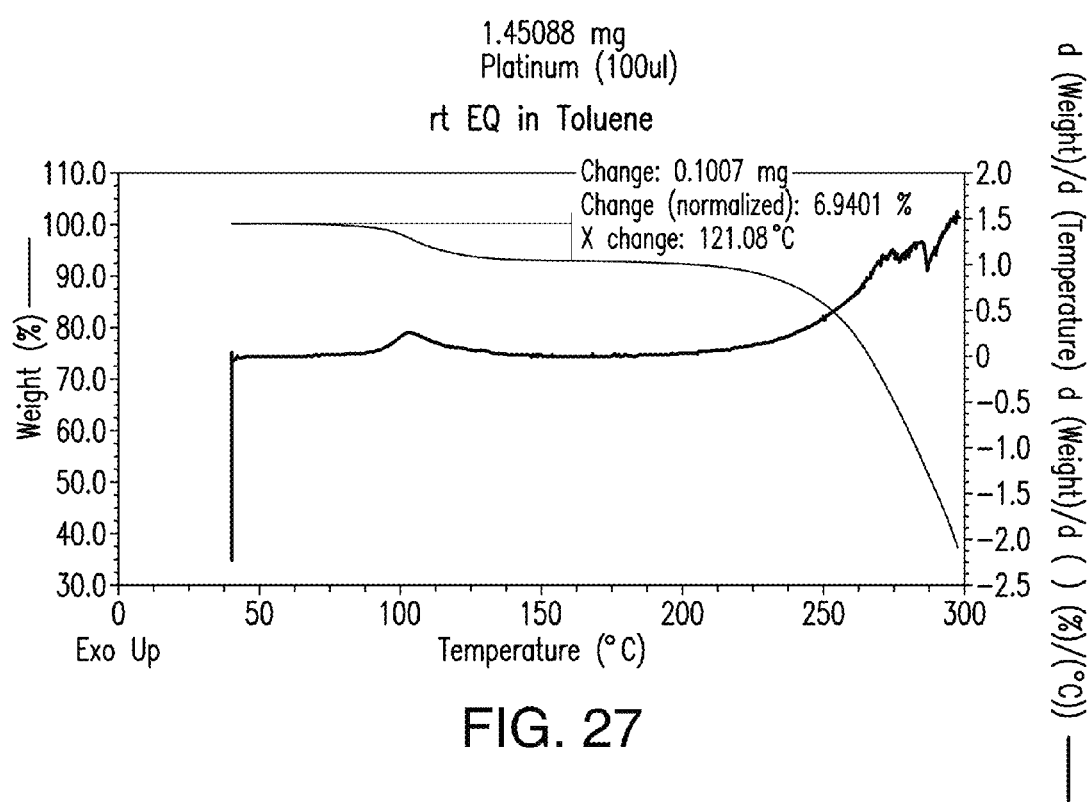
FIG. 27 depicts a TGA thermogram of Form F.

In one embodiment, provided herein is a crystalline form of Compound 1 having a TGA thermograph corresponding substantially to the representative TGA thermogram as depicted in FIG. 27. In certain embodiments, the crystalline form exhibits a TGA thermogram comprising a total mass loss of approximately 6.9% of the total mass of the sample between approximately 75° C. and approximately 175° C. when heated from approximately 25° C. to approximately 300° C. Thus, in certain embodiments, the crystalline form loses about 6.9% of its total mass when heated from about ambient temperature to about 300° C.

Figure 28:
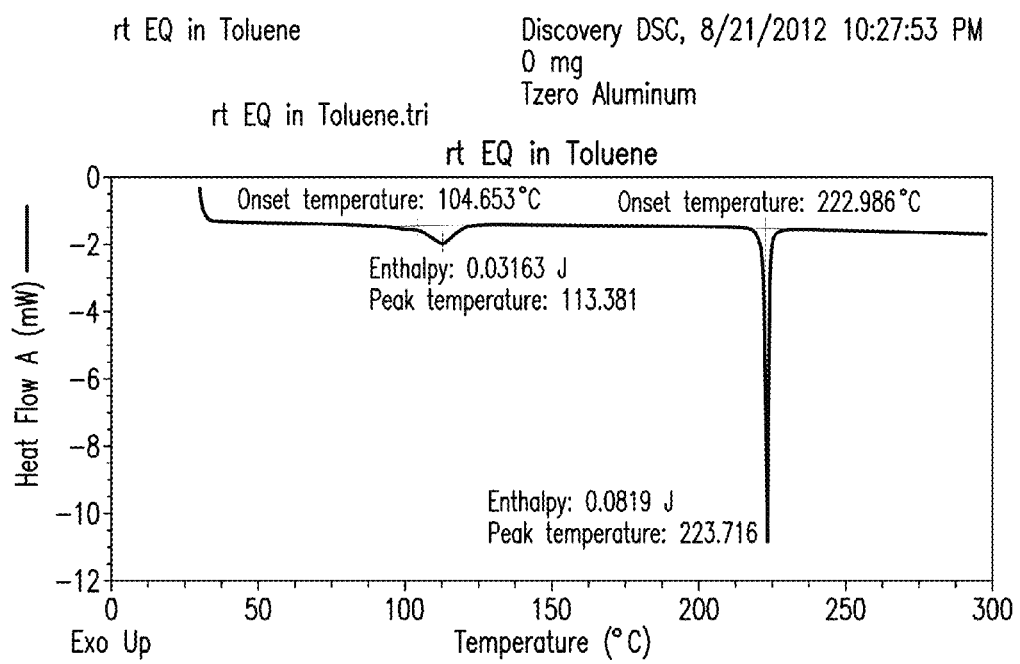
FIG. 28 depicts a DSC thermogram of Form F.

In one embodiment, provided herein is a crystalline form of Compound 1 having a DSC thermogram as depicted in FIG. 28 comprising an endothermic event with a maximum at about 113° C. when heated from approximately 25° C. to approximately 300° C.

In one embodiment, provided herein is a crystalline form of Compound 1 having a DSC thermogram as depicted in FIG. 28 comprising an endothermic event with an onset temperature of about 223° C. when heated from approximately 25° C. to approximately 300° C.

Figure 29:
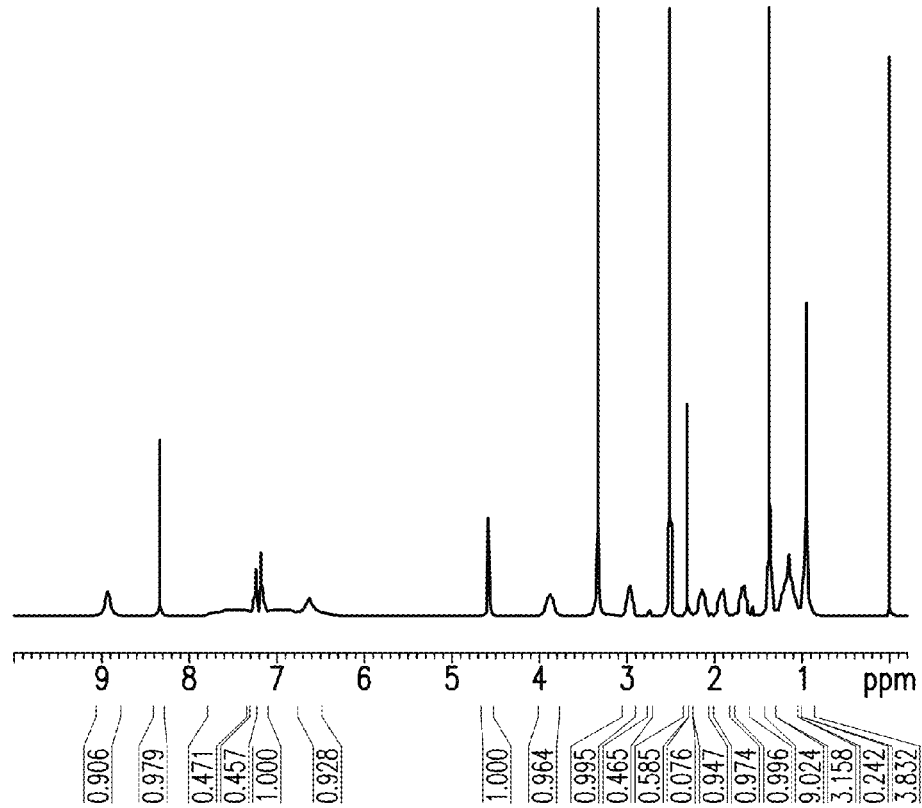
FIG. 29 depicts a $^1$H NMR spectrum of Form F.

In one embodiment, provided herein is Form F having a $^1$H NMR spectrum substantially as depicted in FIG. 29. In one embodiment, the $^1$H NMR spectrum of Form F shows Form F contains about 0.3 molar equivalents of toluene. In certain embodiments, Form F is a 0.3 molar equivalents toluene solvate of Compound 1.

In still another embodiment, Form F is substantially pure. In certain embodiments, the substantially pure Form F is substantially free of other solid forms, e.g., amorphous solid. In certain embodiments, the purity of the substantially pure Form F is no less than about 95%, no less than about 96%, no less than about 97%, no less than about 98%, no less than about 98.5%, no less than about 99%, no less than about 99.5%, or no less than about 99.8%.

Form G

In certain embodiments, provided herein is Form G.

In one embodiment, Form G is a solid form of Compound 1. In another embodiment, Form G is crystalline. In one embodiment, Form G is a solvated form of Compound 1. In one embodiment, Form G is an EtOAc solvated form of Compound 1. In one embodiment, Form G is an EtOAc hemi-solvated form of Compound 1.

In certain embodiments, Form G provided herein is obtained by equilibration experiments, evaporation experiments and anti-solvent recrystallization experiments (see Table 1, Table 2 and Table 3). In certain embodiments, Form G is obtained from certain solvent systems including EtOAc.

Figure 30:
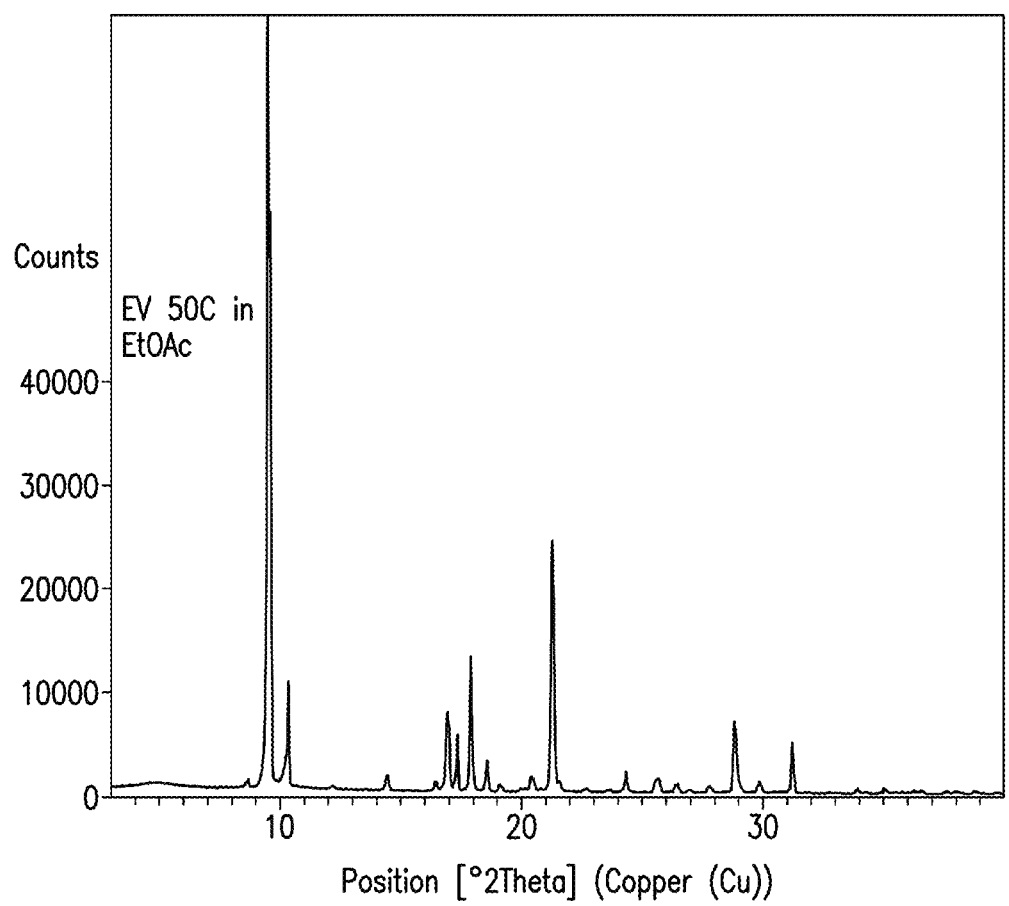
FIG. 30 depicts an XRPD pattern of Form G.

In certain embodiments, a solid form provided herein, e.g., Form G, is substantially crystalline, as indicated by, e.g., X-ray powder diffraction measurements. In one embodiment, Form G has an X-ray powder diffraction pattern substantially as shown in FIG. 30. In one embodiment, Form G has one or more characteristic X-ray powder diffraction peaks at approximately 8.63, 9.51, 10.34, 12.14, 14.43, 16.44, 16.94, 17.33, 17.90, 18.58, 19.10, 20.09, 20.41, 20.80, 21.28, 22.66, 23.62, 24.33, 25.55, 25.65, 26.42, 26.89, 27.00, 27.78, 28.83, 29.86, 31.22, 31.77, 32.67, 33.90, 34.28, 35.04, 35.44, 36.24, 36.57, 37.59, 38.00 or 38.76° 2θ as depicted in FIG. 30. In a specific embodiment, Form G has one, two, three, four, five, six, seven or eight characteristic X-ray powder diffraction peaks at approximately 9.51, 10.34, 16.94, 17.33, 17.90, 21.28, 28.83 or 31.22° 2θ. In another embodiment, Form G has one, two, three or four characteristic X-ray powder diffraction peaks at approximately 9.51, 10.34, 17.90 or 21.28° 2θ. In another embodiment, Form G has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven or thirty-eight characteristic X-ray powder diffraction peaks as set forth in Table 14.

Figure 31:
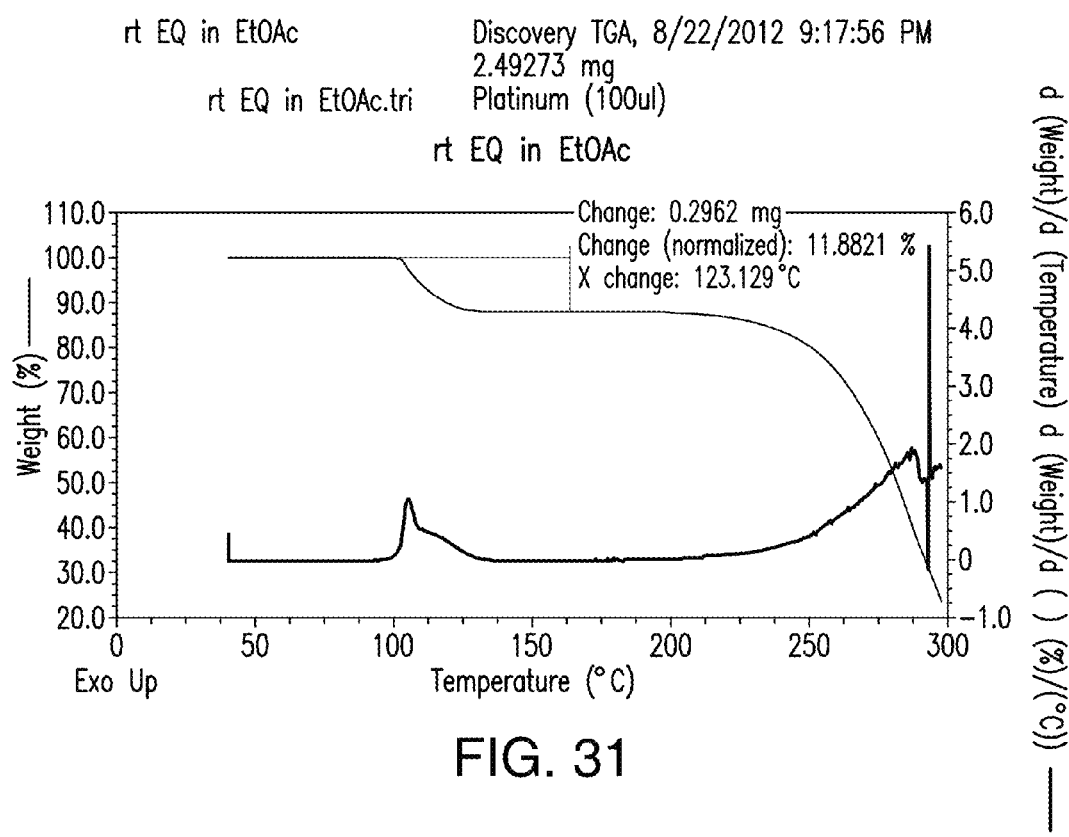
FIG. 31 depicts a TGA thermogram of Form G.

In one embodiment, provided herein is a crystalline form of Compound 1 having a TGA thermograph corresponding substantially to the representative TGA thermogram as depicted in FIG. 31. In certain embodiments, the crystalline form exhibits a TGA thermogram comprising a total mass loss of approximately 11.9% of the total mass of the sample between approximately 75° C. and approximately 175° C. when heated from approximately 25° C. to approximately 300° C. Thus, in certain embodiments, the crystalline form loses about 11.9% of its total mass when heated from about ambient temperature to about 300° C. In certain embodiments, the crystalline form contains 0.5 molar equivalents of solvent in the crystal lattice corresponding to approximately 0.5 mole of EtOAc per mole of Compound 1. The theoretical EtOAc content of an EtOAc hemi-solvate of Compound 1 is 12.1% by weight, matching the TGA weight loss observed. In certain embodiments, the crystalline form is an EtOAc hemi-solvate of Compound 1.

Figure 32:
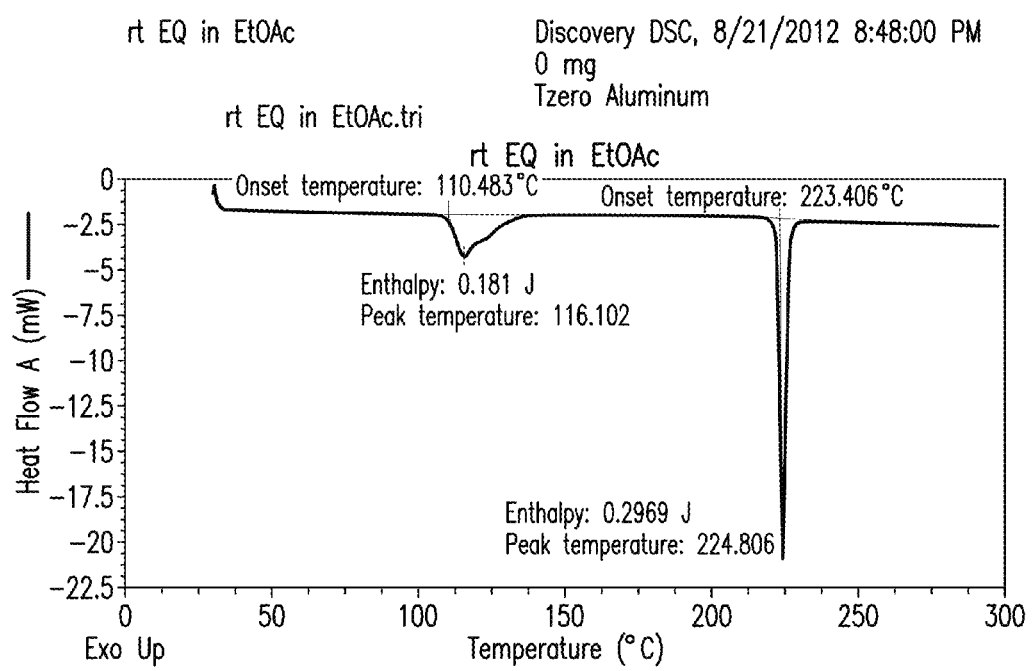
FIG. 32 depicts a DSC thermogram of Form G.

In one embodiment, provided herein is a crystalline form of Compound 1 having a DSC thermogram as depicted in FIG. 32 comprising an endothermic event with a maximum at about 116° C. when heated from approximately 25° C. to approximately 300° C.

In one embodiment, provided herein is a crystalline form of Compound 1 having a DSC thermogram as depicted in FIG. 32 comprising an endothermic event with an onset temperature of about 223° C. when heated from approximately 25° C. to approximately 300° C.

Figure 33:
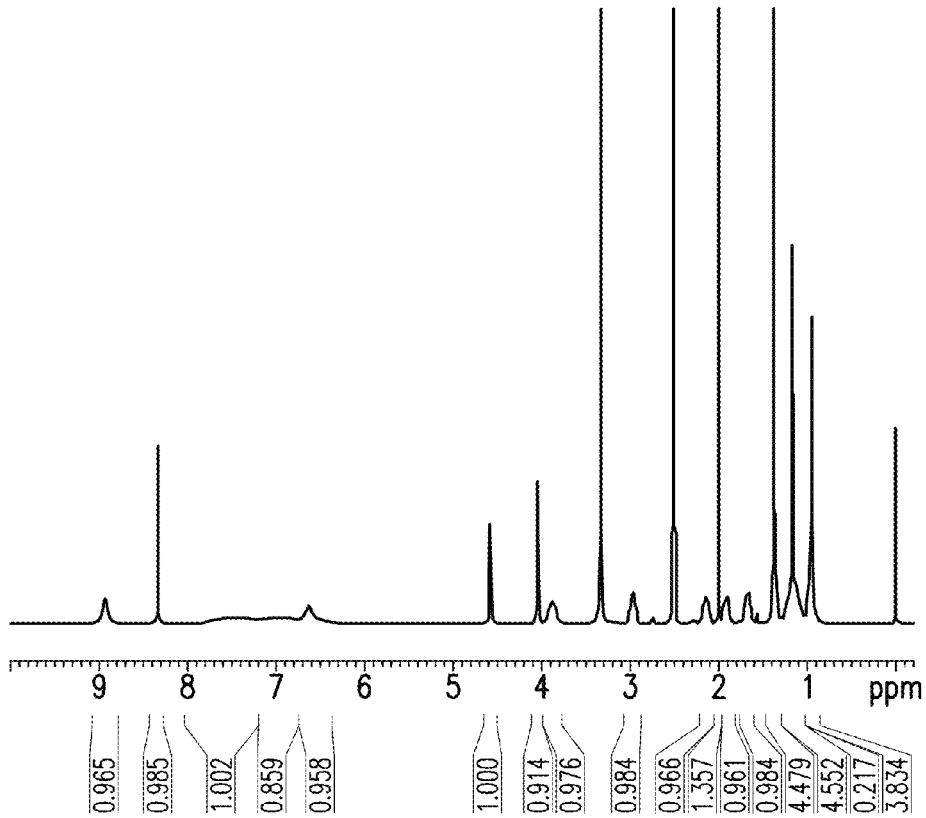
FIG. 33 depicts a $^1$H NMR spectrum of Form G.

In one embodiment, provided herein is Form G having a $^1$H NMR spectrum substantially as depicted in FIG. 33. In one embodiment, the $^1$H NMR spectrum of Form G shows Form G contains about 0.5 molar equivalents of EtOAc. In certain embodiments, Form G is an EtOAc hemi-solvate of Compound 1.

In still another embodiment, Form G is substantially pure. In certain embodiments, the substantially pure Form G is substantially free of other solid forms, e.g., amorphous solid. In certain embodiments, the purity of the substantially pure Form G is no less than about 95%, no less than about 96%, no less than about 97%, no less than about 98%, no less than about 98.5%, no less than about 99%, no less than about 99.5%, or no less than about 99.8%.

Form H

In certain embodiments, provided herein is Form H.

In one embodiment, Form H is a solid form of Compound 1. In another embodiment, Form H is crystalline. In one embodiment, Form H is a solvated form of Compound 1. In one embodiment, Form H is a DMSO solvated form of Compound 1. In one embodiment, Form H is a DMSO hemi-solvated form of Compound 1.

In certain embodiments, Form H provided herein is obtained by equilibration experiments, evaporation experiments, cooling recrystallization experiments and anti-solvent recrystallization experiments. In certain embodiments, Form H is obtained from certain solvent systems including DMSO.

In certain embodiments, provided herein are methods of preparing Form H comprising the steps of 1) mixing 2-chloro-4-((1R,3R,4R)-3-hydroxy-4-methylcyclohexylamino)pyrimidine-5-carboxamide with tert-butylamine and DMSO; 2) heating to a temperature (e.g., from between about 55 to about 80° C., such as about 68° C.) for a period of time (e.g., from about 40 hours to about 80 hours, such as about 60 hours); 3) cooling to ambient temperature; 4) adding water; and 5) collecting solids and optionally drying. In one embodiment, the temperature is from between about 55 to about 80° C., such as about 68° C. In one embodiment, the period of time is from about 40 hours to about 80 hours, such as about 60 hours. In another embodiment, water is added over from about 1 hour to about 4 hours, such as about 2 hours.

Figure 34:
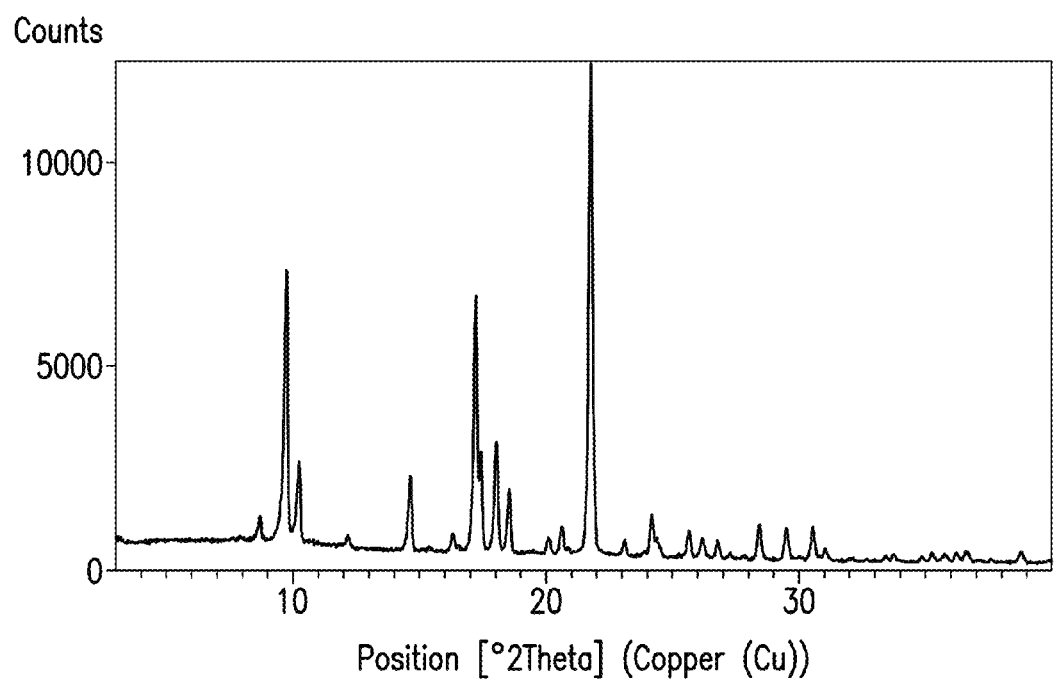
FIG. 34 depicts an XRPD pattern of Form H.

In certain embodiments, a solid form provided herein, e.g., Form H, is substantially crystalline, as indicated by, e.g., X-ray powder diffraction measurements. In one embodiment, Form H has an X-ray powder diffraction pattern substantially as shown in FIG. 34. In one embodiment, Form H has one or more characteristic X-ray powder diffraction peaks at approximately 8.69, 9.74, 10.23, 12.17, 14.64, 15.38, 16.33, 17.22, 18.04, 18.55, 20.10, 20.62, 21.76, 23.10, 24.18, 25.65, 26.18, 26.78, 27.27, 27.83, 28.43, 29.50, 30.00, 30.54, 31.03, 32.07, 32.65, 33.41, 33.74, 34.86, 35.25, 35.77, 36.22, 36.62, 37.08, 37.59 or 38.78° 2θ as depicted in FIG. 34. In a specific embodiment, Form H has one, two, three, four, five, six, seven or eight characteristic X-ray powder diffraction peaks at approximately 9.74, 10.23, 14.64, 17.22, 18.04, 18.55, 21.76 or 24.18° 2θ. In another embodiment, Form H has one, two, three or four characteristic X-ray powder diffraction peaks at approximately 9.74, 17.22, 18.04 or 21.76° 2θ. In another embodiment, Form H has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six or thirty-seven characteristic X-ray powder diffraction peaks as set forth in Table 15.

Figure 35:
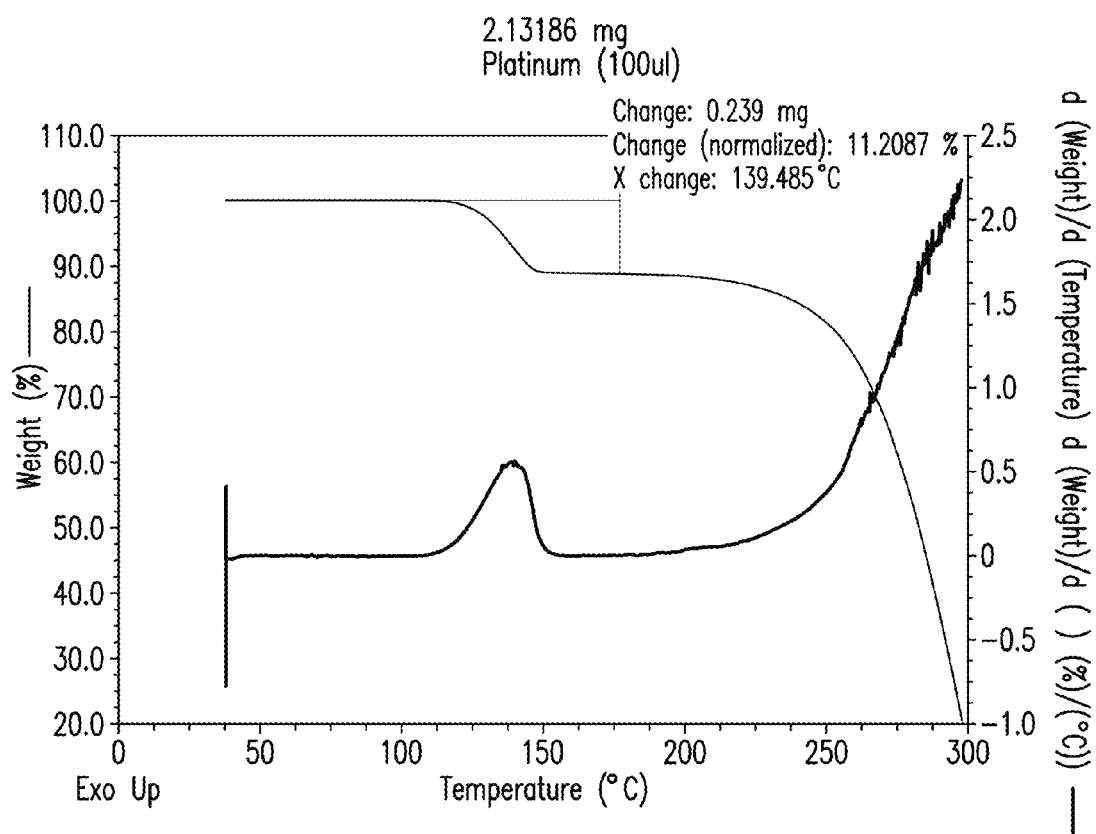
FIG. 35 depicts a TGA thermogram of Form H.

In one embodiment, provided herein is a crystalline form of Compound 1 having a TGA thermograph corresponding substantially to the representative TGA thermogram as depicted in FIG. 35. In certain embodiments, the crystalline form exhibits a TGA thermogram comprising a total mass loss of approximately 11.2% of the total mass of the sample between approximately 75° C. and approximately 175° C. when heated from approximately 25° C. to approximately 300° C. Thus, in certain embodiments, the crystalline form loses about 11.2% of its total mass when heated from about ambient temperature to about 300° C. In certain embodiments, the crystalline form contains 0.5 molar equivalents of solvent in the crystal lattice corresponding to approximately 0.5 mole of DMSO per mole of Compound 1. The theoretical DMSO content of a DMSO hemi-solvate of Compound 1 is 10.8% by weight, matching the TGA weight loss observed. In certain embodiments, the crystalline form is a DMSO hemi-solvate of Compound 1.

Figure 36:
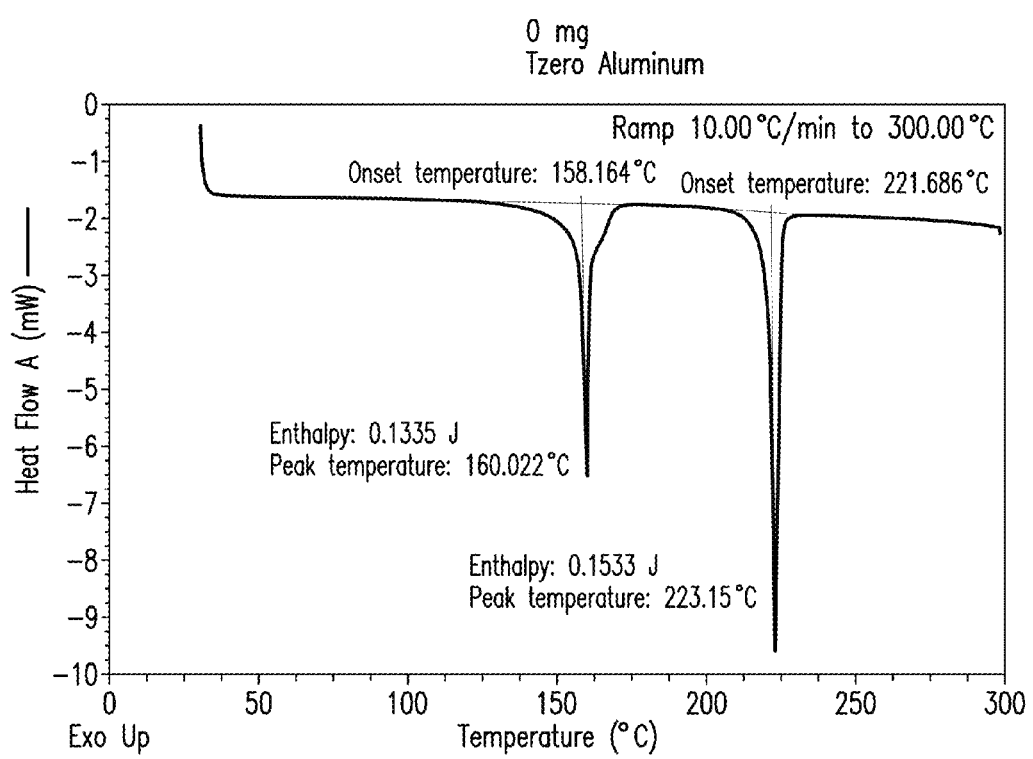
FIG. 36 depicts a DSC thermogram of Form H.

In one embodiment, provided herein is a crystalline form of Compound 1 having a DSC thermogram as depicted in FIG. 36 comprising an endothermic event with a maximum at about 160° C. when heated from approximately 25° C. to approximately 300° C.

In one embodiment, provided herein is a crystalline form of Compound 1 having a DSC thermogram as depicted in FIG.

36 comprising an endothermic event with an onset temperature of about 222° C. when heated from approximately 25° C. to approximately 300° C.

In still another embodiment, Form H is substantially pure. In certain embodiments, the substantially pure Form H is substantially free of other solid forms, e.g., amorphous solid. In certain embodiments, the purity of the substantially pure Form H is no less than about 95%, no less than about 96%, no less than about 97%, no less than about 98%, no less than about 98.5%, no less than about 99%, no less than about 99.5%, or no less than about 99.8%.

Form I

In certain embodiments, provided herein is Form I.

In one embodiment, Form I is a solid form of Compound 1. In another embodiment, Form I is crystalline. In one embodiment, Form I is a solvated form of Compound 1. In one embodiment, Form I is a sulfolane solvated form of Compound 1. In one embodiment, Form I is a 0.75 molar sulfolane solvated form of Compound 1.

In certain embodiments, Form I provided herein is obtained by cooling recrystallization experiments and antisolvent recrystallization experiments. In certain embodiments, Form I is obtained from certain solvent systems including sulfolane and water. In certain embodiments, Form I is obtained from a solvent mixture of sulfolane and water (e.g., about 1:1).

Figure 38:
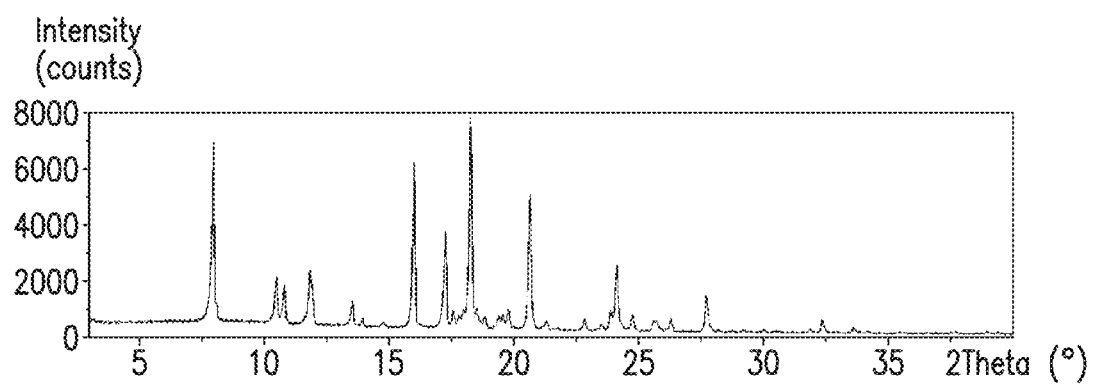
FIG. 38 depicts an XRPD pattern of Form I.

In certain embodiments, a solid form provided herein, e.g., Form I, is substantially crystalline, as indicated by, e.g., X-ray powder diffraction measurements. In one embodiment, Form I has an X-ray powder diffraction pattern substantially as shown in FIG. 38. In one embodiment, Form I has one or more characteristic X-ray powder diffraction peaks at approximately 7.94, 10.50, 10.80, 11.86, 13.54, 13.92, 14.79, 16.00, 17.26, 18.27, 18.82, 19.48, 19.78, 20.65, 21.31, 21.78, 22.83, 23.53, 24.12, 24.75, 25.66, 26.29, 27.71, 28.18, 28.73, 29.17, 30.01, 30.52, 31.18, 31.60, 31.85, 32.36, 32.93, 33.59, 34.20, 34.76, 35.42, 36.56 or 37.67° 2θ as depicted in FIG. 38. In a specific embodiment, Form I has one, two, three, four, five, six, seven or eight characteristic X-ray powder diffraction peaks at approximately 7.94, 10.50, 11.86, 16.00, 17.26, 18.27, 20.65 or 24.12° 2θ. In another embodiment, Form I has one, two, three or four characteristic X-ray powder diffraction peaks at approximately 7.94, 16.00, 18.27 or 20.65° 2θ. In another embodiment, Form I has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight or thirty-nine characteristic X-ray powder diffraction peaks as set forth in Table 16.

Figure 39:
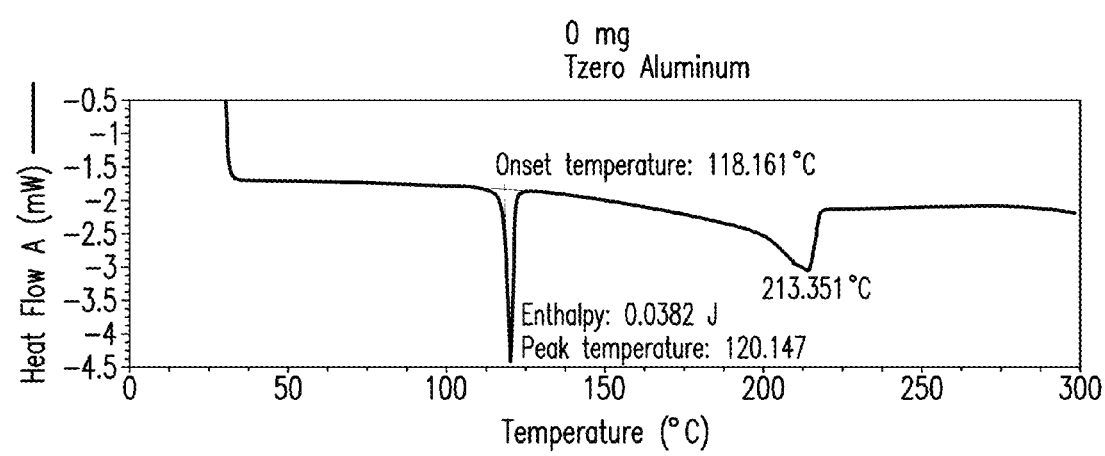
FIG. 39 depicts a DSC thermogram of Form I.

In one embodiment, provided herein is a crystalline form of Compound 1 having a DSC thermogram as depicted in FIG. 39 comprising an endothermic event with a maximum at about 118° C. when heated from approximately 25° C. to approximately 300° C.

In one embodiment, provided herein is a crystalline form of Compound 1 having a DSC thermogram as depicted in FIG. 39 comprising an endothermic event with an onset temperature of about 213° C. when heated from approximately 25° C. to approximately 300° C.

In still another embodiment, Form I is substantially pure. In certain embodiments, the substantially pure Form I is substantially free of other solid forms, e.g., amorphous solid. In certain embodiments, the purity of the substantially pure Form I is no less than about 95%, no less than about 96%, no less than about 97%, no less than about 98%, no less than about 98.5%, no less than about 99%, no less than about 99.5%, or no less than about 99.8%.

Amorphous Solid

In certain embodiments, provided herein is an amorphous solid of Compound 1.

In certain embodiments, the amorphous solid provided herein is obtained by heat treatment of Form A. In certain embodiments, the heat treatment process comprises: (1) equilibrating the temperature of Form A at a particular temperature (e.g., about 25° C.); (2) heating to a first temperature (e.g., about 235° C.) at a first speed (e.g., about 10° C. per minute); (3) holding isothermally for a first period of time (e.g., about 2 minutes); (4) cooling to a second temperature (e.g., about −10° C.) at a second speed (e.g., about 30° C. per minute); (5) modulating the temperature at a third speed (e.g., about 0.64° C. every 40 seconds); (6) holding isothermally for a second period of time (e.g., about 5 minutes); (7) heating to a third temperature (e.g., about 213° C.) at a fourth speed (e.g., about 3° C. per minute); and (8) collecting the resulted solid.

Figure 41:
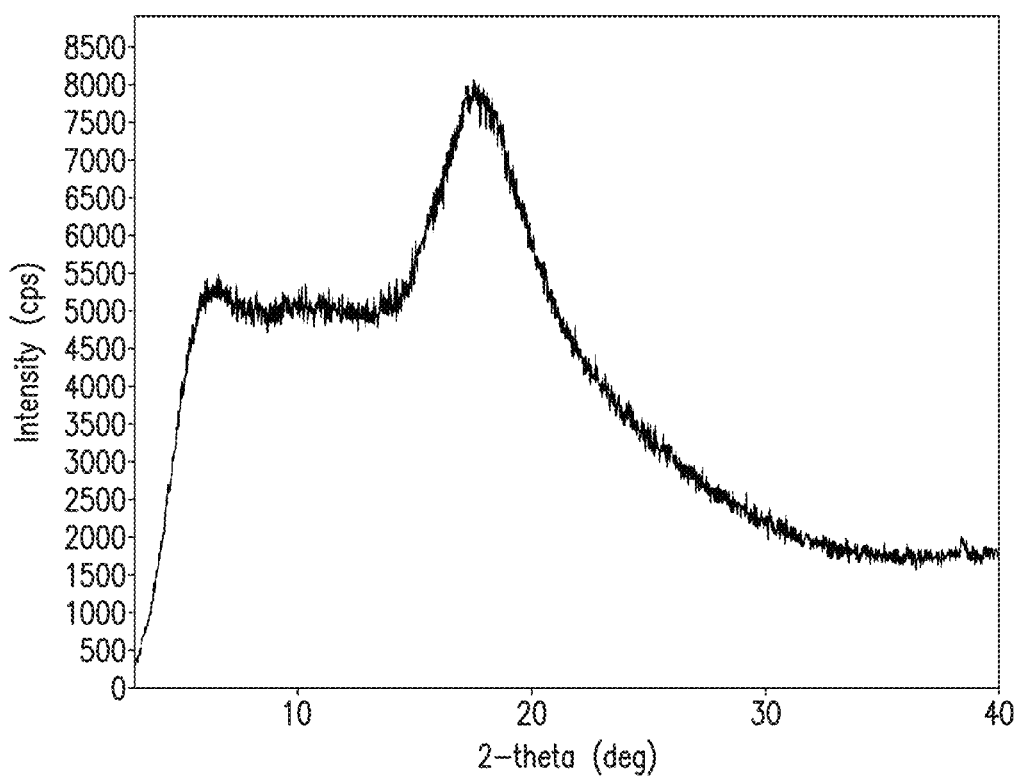
FIG. 41 depicts an XRPD pattern of the amorphous solid.

In one embodiment, the amorphous solid has an X-ray powder diffraction spectrum substantially as shown in FIG. 41.

Figure 42:
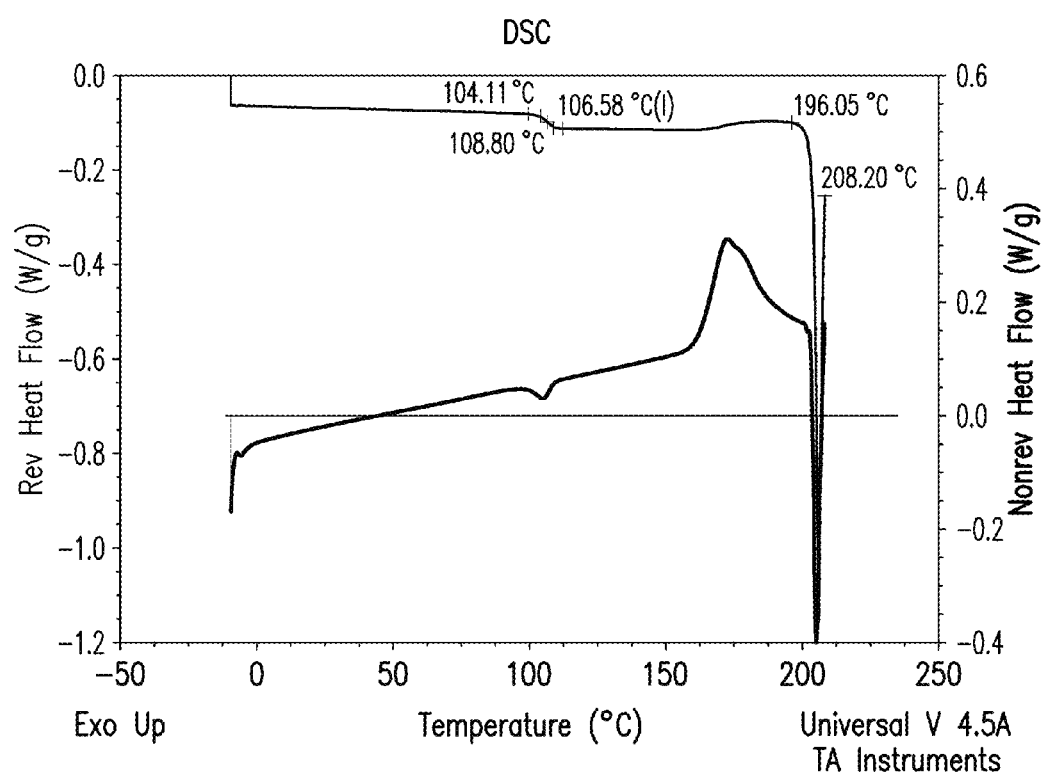
FIG. 42 depicts a DSC thermogram of the amorphous solid.

In one embodiment, provided herein is an amorphous solid of Compound 1 having a DSC thermogram as depicted in FIG. 42 comprising a glass transition temperature of 106.6° C. when heated from approximately 25° C. to approximately 300° C.

In still another embodiment, the amorphous solid of Compound 1 is substantially pure. In certain embodiments, the substantially pure amorphous solid of Compound 1 is substantially free of other solid forms, e.g., Form A, Form B, Form C, Form D, Form E, Form F, Form G, Form H, and Form I. In certain embodiments, the purity of the substantially pure amorphous solid is no less than about 95%, no less than about 96%, no less than about 97%, no less than about 98%, no less than about 98.5%, no less than about 99%, no less than about 99.5%, or no less than about 99.8%.

Methods of Use

Solid forms of Compound 1 have utility as pharmaceuticals to treat, prevent or improve conditions in animals or humans. Further, the solid forms of Compound 1 are active against protein kinases, particularly JNK1 and/or JNK2. Accordingly, provided herein are many uses of the solid forms of Compound 1, including the treatment or prevention of those diseases set forth below. The methods provided herein comprise the administration of an effective amount of one or more solid form(s) of Compound 1 to a subject in need thereof.

In one aspect provided herein are methods of inhibiting a kinase in a cell expressing said kinase, comprising contacting said cell with an effective amount of a solid form of Compound 1. In one embodiment the kinase is JNK1, JNK2, or mutants or isoforms thereof, or a combination thereof. For example, the solid form of Compound A is Form A, Form B, Form C, Form D, Form E, Form F, Form G, Form H, Form I, the amorphous solid or a mixture thereof. In a further aspect provided herein are the solid forms of Compound 1 for use in such methods of inhibiting a kinase in a cell expressing said kinase.

In another aspect provided herein are methods for treating or preventing one or more disorders selected from interstitial pulmonary fibrosis, systemic sclerosis, scleroderma, chronic allograft nephropathy, antibody mediated rejection, or lupus, comprising administering to a subject in need thereof an effective amount of a solid form of Compound 1. In some such embodiments, the lupus is lupus erythematosus (such as discoid lupus erythematosus, or cutaneous lupus erythematosus) or systemic lupus. In a further aspect provided herein are the solid forms of Compound 1 for use in such methods for treating or preventing one or more disorders selected from interstitial pulmonary fibrosis, systemic sclerosis, scleroderma, chronic allograft nephropathy, antibody mediated rejection, or lupus.

In another aspect provided herein are methods for treating or preventing liver fibrotic disorders, such as non-alcoholic steatohepatitis, steatosis (i.e. fatty liver), cirrhosis, primary sclerosing cholangitis, primary biliary cirrhosis, hepatitis, hepatocellular carcinoma, and liver fibrosis coincident with chronic or repeated alcohol ingestion (alcoholic hepatitis), with infection (e.g., viral infection such as HCV), with liver transplant, or with drug induced liver injury (e.g., acetaminophen toxicity), comprising administering to a subject in need thereof an effective amount of a solid form of Compound 1. In some such aspects, provided herein are methods for treating or preventing diabetes or metabolic syndrome leading to liver fibrotic disorders, such as non-alcoholic steatohepatitis, steatosis (i.e. fatty liver), cirrhosis, primary sclerosing cholangitis, primary biliary cirrhosis, and hepatitis, comprising administering to a subject in need thereof an effective amount of a solid form of Compound 1. In a further aspect provided herein are the solid forms of Compound 1 for use in such methods.

In another aspect provided herein are methods for treating or preventing conditions treatable or preventable by inhibition of JNK1 and/or JNK2, the method comprising administering to a subject in need thereof an effective amount of a solid form of Compound 1. Examples of such conditions include rheumatoid arthritis; rheumatoid spondylitis; osteoarthritis; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; hepatitis; pancreatitis; nephritis; multiple sclerosis; lupus erythematosus; Type II diabetes; obesity; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine. In a further aspect provided herein are the solid forms of Compound 1 for use in such methods. Generally, all compounds of the present invention are intended for use in a method of treatment of all diseases disclosed.

Pharmaceutical Compositions and Routes of Administration

The solid forms of Compound 1 can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the solid forms of Compound 1 in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a solid form of Compound 1 to be administered to a subject is rather widely variable and can be subject to the judgment of a healthcare practitioner. In general, the solid forms of Compound 1 can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the solid form of Compound 1 administered will depend on such factors as the solubility of the active component, the formulation used and the route of administration. In one embodiment, application of a topical concentration provides intracellular exposures or concentrations of about 0.01-10 µM.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a solid form of Compound 1 to a subject in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day, about 60 mg/day to about 720 mg/day, about 240 mg/day to about 720 mg/day or about 600 mg/day to about 800 mg/day of a solid form of Compound 1 to a subject in need thereof. In a particular embodiment, the methods disclosed herein comprise the administration of 400 mg/day, 600 mg/day or 800 mg/day of a solid form of Compound 1 to a subject in need thereof.

In another embodiment, provided herein are methods for the treatment or prevention of a disease or disorder comprising the administration of about 10 mg/day to about 720 mg/day, about 10 mg/day to about 480 mg/day, about 60 mg/day to about 720 mg/day or about 240 mg/day to about 720 mg/day of a solid form of Compound 1 to a subject in need thereof.

In another embodiment, provided herein are unit dosage formulations that comprise between about 10 mg and 100 mg, about 1 mg and 200 mg, about 35 mg and about 1400 mg, about 125 mg and about 1000 mg, about 250 mg and about 1000 mg, or about 500 mg and about 1000 mg of a solid form of Compound 1.

In a particular embodiment, provided herein are unit dosage formulations comprising about 100 mg or 400 mg of a solid form of Compound 1.

In another embodiment, provided herein are unit dosage formulations that comprise about 1 mg, 5 mg, 10 mg, 15 mg, 20 mg, 30 mg, 35 mg, 50 mg, 60 mg, 70 mg, 100 mg, 120 mg, 125 mg, 140 mg, 175 mg, 200 mg, 240 mg, 250 mg, 280 mg, 350 mg, 480 mg, 500 mg, 560 mg, 700 mg, 720 mg, 750 mg, 1000 mg or 1400 mg of a solid form of Compound 1.

In another embodiment, provided herein are unit dosage formulations that comprise about 10 mg, 30 mg or 100 mg of a solid form of Compound 1.

A solid form of Compound 1 can be administered once, twice, three, four or more times daily. In a particular embodiment, doses of 600 mg or less are administered as a once daily dose and doses of more than 600 mg are administered twice daily in an amount equal to one half of the total daily dose. In one embodiment, a solid form of Compound 1 can be administered once daily for 14 days.

A solid form of Compound 1 can be administered orally for reasons of convenience. In one embodiment, when administered orally, a solid form of Compound 1 is administered with a meal and water. In another embodiment, the solid form of Compound 1 is dispersed in water or juice (e.g., apple juice or orange juice) and administered orally as a suspension.

The solid form of Compound 1 can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a solid form of Compound 1 without an additional carrier, excipient or vehicle.

In another embodiment, provided herein are compositions comprising an effective amount of a solid form of Compound 1 and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a solid form of Compound 1 with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a solid form of Compound 1 as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

In certain embodiments, the pharmaceutical compositions provided herein comprise Form A, including substantially pure Form A.

In certain embodiments, the pharmaceutical compositions provided herein comprise Form B, including substantially pure Form B.

In certain embodiments, the pharmaceutical compositions provided herein comprise Form C, including substantially pure Form C.

In certain embodiments, the pharmaceutical compositions provided herein comprise Form D, including substantially pure Form D.

In certain embodiments, the pharmaceutical compositions provided herein comprise Form E, including substantially pure Form E.

In certain embodiments, the pharmaceutical compositions provided herein comprise Form F, including substantially pure Form F.

In certain embodiments, the pharmaceutical compositions provided herein comprise Form G, including substantially pure Form G.

In certain embodiments, the pharmaceutical compositions provided herein comprise Form H, including substantially pure Form H.

In certain embodiments, the pharmaceutical compositions provided herein comprise Form I, including substantially pure Form I.

In certain embodiments, the pharmaceutical compositions provided herein comprise the amorphous solid, including the substantially pure amorphous solid.

In certain embodiments, the pharmaceutical compositions provided herein comprise a mixture of one or more solid form(s) of Compound 1, including Form A, Form B, Form C, Form D, Form E, Form F, Form G, Form H, Form I and the amorphous solid, wherein every possible combination of the solid forms of Compound 1 is possible.

EXAMPLES

The following Examples are presented by way of illustration, not limitation. The following abbreviations are used in descriptions and examples:
ACN: Acetonitrile
Am: Amorphous
AmPhos: p-Dimethylamino phenylditbutylphosphine
API: Active Pharmaceutical Ingredient
Boc: tert-Butoxycarbonyl
n-BuOH: n-Butanol
dba: Dibenzylidene acetone
DBU: 1,8-Diazabicyclo[5.4.0]undec-7-ene
DCM: Dichloromethane
DIPEA: N,N-Diisopropylethylamine
DMAc: N,N-Dimethylacetamide
DMF: N,N-Dimethylformide
DMSO: Dimethylsulfoxide
DSC: Differential Scanning calorimetry
DVS: Dynamic Vapor Sorption
EDTA: Ethylenediamine tetraacetate
ESI: Electronspray ionization
EtOAc: Ethyl acetate
EtOH: Ethanol
FTIR: Fourier Transform Infra Red Spectroscopy
HPLC: High performance liquid chromatography
IPA: 2-Propanol
IPAc: Isopropyl acetate
LCMS: Liquid Chromatography with Mass Spectroscopy
MEK: Methyl ethyl ketone
MeOH: Methanol
2-MeTHF: 2-Methyl tetrahydrofuran
mp: Melting point
MS: Mass spectrometry
MTBE: tert-Butyl methyl ether
NBS: N-Bromosuccinimide
NMP: N-Methyl-2-pyrrolidone
NMR: Nuclear magnetic resonance
RH: Relative Humidity
RT: Room Temperature
Rx Recrystallization
S: Solvent
SDTA: Single Differential Thermal Analysis
SM: Starting material
S-SegPhos (S)-(−)-5,5-Bis(diphenylphosphino)-4,4-bi-1,3-benzodioxole
TA: Thermal Analysis
Tf: Triflate or trifluoromethanesulfonyl
TFA: Trifluoroacetic acid
TFE: 2,2,2-Trifluoroethanol
TGA: Thermogravimetric Analysis
TGA-MS/TG-MS: Thermogravimetric Analysis coupled with Mass Spectroscopy
THF: Tetrahydrofuran
TLC: Thin layer chromatography
XRPD: X-Ray Powder Diffraction Synthetic Examples The following non-limiting synthetic examples show methods for the preparation of Compound 1. ACD/NAME (Advanced Chemistry Development, Inc., Ontario, Canada) was used to generate names for chemical structures and Chemdraw (Cambridgesoft, Perkin Elmer, Waltham, Mass.) draw the chemical structures.

Example 1

2-(tert-Butylamino)-4-{[(1R,3R,4R)-3-hydroxy-4-methylcyclohexyl]amino}pyrimidine-5-carboxamide

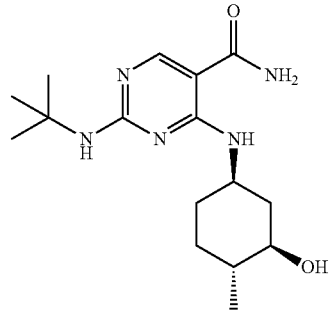 [SMILES: C[C@@H]1CC[C@@H](Nc2nc(NC(C)(C)C)ncc2C(N)=O)C[C@H]1O]

2-Chloro-4-{[(1R,3R,4R)-3-hydroxy-4-methylcyclohexyl]amino}pyrimidine-5-carboxamide To a reactor was added (1R,2R,5R)-5-amino-2-methylcyclohexanol hydrochloride (16.0 kg), 2,4-dichloropyrimidine-5-carboxamide (19.0 kg), K$_2$CO$_3$ (14.9 kg) and THF (160 L) at 25° C. The batch was cooled to 0° C., and water (160 L) was added. The batch was stirred for an additional 1 h at 0° C., warmed to 25° C. and held for 16 h. Water (288 L) was added to the batch while keeping the batch at 25° C., and the batch was cooled to 15° C. and agitated for an additional 4 hs. The batch was filtered, rinsed twice with water (2×80 L), and dried in a vacuum oven at 40° C. with nitrogen bleed for 24 h to give 2-chloro-4-{[(1R,3R,4R)-3-hydroxy-4-methylcyclohexyl]amino}pyrimidine-5-carboxamide as white powder (23.3 kg, 86% yield). $^1$H NMR (DMSO-d$_6$) δ 0.93 (d, J=5.7 Hz, 3H), 0.97-1.29 (m, 4H), 1.63-1.68 (m, 1H), 1.75-1.88 (m, 1H), 2.09-2.13 (m, 1H), 3.00-3.08 (m, 1H), 3.80-3.95 (m, 1H), 4.65 (d, J=5.1 Hz, 1H), 7.69 (br. s., 1H), 8.20 (br. s., 1H), 8.53 (s, 1H), 9.22 (d, J=7.5 Hz, 1H).

2-(tert-Butylamino)-4-{[(1R,3R,4R)-3-hydroxy-4-methylcyclohexyl]amino}pyrimidine-5-carboxamide (Compound 1)

To a reactor was charged 2-chloro-4-{[(1R,3R,4R)-3-hydroxy-4-methylcyclohexyl]amino}pyrimidine-5-carboxamide (41 kg), t-butylamine (105.3 kg) and DMSO (205 L). The batch was heated to 68° C. under 10 psig of nitrogen pressure, held for 80 h, and cooled to 25° C. The batch was filtered through a 0.45 µm in-line filter to a second reactor. The batch was heated to 60° C., and water (205 L) was charged through a 0.45 µm in-line filter. The batch was seeded with micronized Compound 1 (820 g) agitated at 60° C. for over an hour, and water (615 L) was charged to the batch through a 0.45 µm in-line filter in 3 h at 60° C. The batch was agitated for 1 h at 60° C., cooled to 25° C. over 6 h, filtered, and washed with water (410 mL), which was filtered through a 0.45 µm in-line filter. The solids were dried in a vacuum oven at 40° C. with nitrogen bleed for over 72 h to give 2-(tert-butylamino)-4-{[(1R,3R,4R)-3-hydroxy-4-methylcyclohexyl]amino}pyrimidine-5-carboxamide as Form A and a white solid (43.5 kg, 94% yield). $^1$H NMR (DMSO-d$_6$) δ 0.95 (d, J=6.2 Hz, 3H), 0.97-1.28 (m, 4H), 1.37 (s, 9H), 1.60-1.75 (m, 1H), 1.83-2.00 (m, 1H), 2.06-2.26 (m, 1H), 2.86-3.07 (m, 1H), 3.74-4.01 (m, 1H), 4.59 (d, J=5.7 Hz, 1H), 6.65 (br. s., 1H), 7.03 (br. s., 1H), 7.57 (br. s., 1H), 8.36 (s, 1H), 8.93 (br. s., 1H).

Recrystallization of 2-(tert-butylamino)-4-{[(1R,3R,4R)-3-hydroxy-4-methylcyclohexyl]amino}pyrimidine-5-carboxamide (Compound 1)

To a reactor was charged 2-(tert-butylamino)-4-{[(1R,3R,4R)-3-hydroxy-4-methylcyclohexyl]amino}pyrimidine-5-carboxamide (30 g), 2-propanol (203 mL) and water (67.5 mL). The batch was heated to 35° C. and filtered through a 0.45 µm in-line filter at 35° C. into a second reactor. The first reactor and transfer lines were rinsed with a mixture of 2-propanol (33.75 mL) and water (11.25 mL) that was filtered through a 0.45 µm filter. The batch was heated to 70° C., and water (360 mL) was charged through a 0.45 µm in-line filter to the batch maintaining a batch temperature of 70° C. The batch was cooled to 60° C., seeded with a slurry of Compound 1 (0.9 g) in filtered 2-propanol:water mixture (9 mL; 1:9 v/v) at 60° C. The batch was agitated at 60° C. for 30 min, cooled to 0° C., agitated at 0° C. for 14 h, filtered, and washed with a 2-propanol:water mixture (60 mL; 1:9 v/v 60 mL) via a 0.45 µm in-line filter. The batch was dried in a vacuum oven at 40° C. with nitrogen bleed for 72 h to give 2-(tert-butylamino)-4-{[(1R,3R,4R)-3-hydroxy-4-methylcyclohexyl]amino}pyrimidine-5-carboxamide as Form A and a white solid (26 g, 85% yield). $^1$H NMR (DMSO-d$_6$) δ 0.95 (d, J=6.2 Hz, 3H), 0.97-1.28 (m, 4H), 1.37 (s, 9H), 1.60-1.75 (m, 1H), 1.83-2.00 (m, 1H), 2.06-2.26 (m, 1H), 2.86-3.07 (m, 1H), 3.74-4.01 (m, 1H), 4.59 (d, J=5.7 Hz, 1H), 6.65 (br. s., 1H), 7.03 (br. s., 1H), 7.57 (br. s., 1H), 8.36 (s, 1H), 8.93 (br. s., 1H).

Example 2

4-(tert-Butylamino)-2-((trans-4-hydroxycyclohexyl)amino)pyrimidine-5-carboxamide

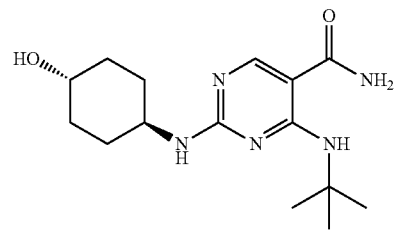 [SMILES: CC(C)(C)Nc1nc(N[C@H]2CC[C@H](O)CC2)ncc1C(N)=O]

4-(tert-Butylamino)-2-chloropyrimidine-5-carboxamide

A mixture of 2,4-dichloro-pyrimidine-5-carboxamide (10.0 g), DIPEA (11 mL) in NMP (30 mL) were stirred at 25° C. tert-Butylamine (6.6 mL) was charged to the mixture, and the mixture was stirred at 25° C. for 16 h. Water (100 mL) was added to the mixture at 25° C. The mixture was stirred for 1 h. The suspension was filtered, washed with water (50 mL) and dried in a vacuum oven at 40° C. with a nitrogen bleed for 24 h to give 4-(tert-butylamino)-2-chloropyrimidine-5-carboxamide as a white solid (8.7 g, 84%). $^1$H NMR (DMSO-d$_6$) δ 9.41 (s, 1H), 8.55 (s, 1H), 8.19 (s, 1H), 7.67 (s, 1H), 1.42 (s, 9H).

4-(tert-Butylamino)-2-((trans-4-hydroxycyclohexyl)amino)pyrimidine-5-carboxamide A mixture of 4-(tert-butylamino)-2-chloropyrimidine-5-carboxamide (0.5 g), trans-4-aminocyclohexanol hydrochloride (0.40 g), Na$_2$CO$_3$ (0.28 g) in NMP (3.5 mL) was heated at 85° C. and held for 6 h. The mixture was cooled to 35° C., and water (10 mL) was added. After 30 minutes, the batch was cooled to 25° C. and held for 1 h. The suspension was filtered, washed with water (2.5 mL) and dried in a vacuum oven at 40° C. with a nitrogen bleed for 24 h to give 4-(tert-butylamino)-2-((trans-4-hydroxycyclohexyl)amino)pyrimidine-5-carboxamide as a white solid (0.6 g, 89%). $^1$H NMR (DMSO-d$_6$) δ 9.17 (broads, 1H), 8.32 (s, 1H), 7.01 (broads, 1H), 4.52 (d, J=4.5 Hz, 1H), 3.70-3.25 (m, 2H), 1.84 (m, 4H), 1.41 (s, 9H), 1.33-1.16 (m, 4H).

Recrystallization of 4-(tert-butylamino)-2-((trans-4-hydroxycyclohexyl)amino)pyrimidine-5-carboxamide A mixture of 4-(tert-butylamino)-2-((trans-4-hydroxycyclohexyl)amino)pyrimidine-5-carboxamide (0.2 g) in ethanol (1.0 mL) was heated to 60° C. and held for 30 minutes. Water (4 mL) was charged over 1 h. The mixture was cooled to 25° C. over 1 h and held for 1 h. The suspension was filtered, washed with water (4 mL), and dried in a vacuum oven at 40° C. with a nitrogen bleed for 24 h to give 4-(tert-butylamino)-2-((trans-4-hydroxycyclohexyl)amino)pyrimidine-5-carboxamide (0.18 g, 90% yield). $^1$H NMR (DMSO-d$_6$) δ 9.17 (broads, 1H), 8.32 (s, 1H), 7.01 (broads, 1H), 4.52 (d, J=4.5 Hz, 1H), 3.70-3.25 (m, 2H), 1.84 (m, 4H), 1.41 (s, 9H), 1.33-1.16 (m, 4H).

Example 3

4-(Bicyclo[1.1.1]pentan-1-ylamino)-2-(((1R,3S)-3-hydroxycyclohexyl)amino)pyrimidine-5-carboxamide

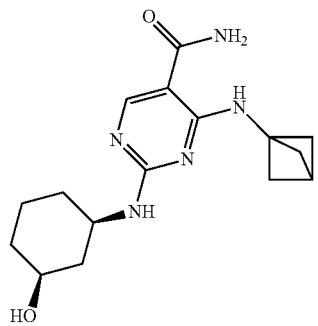 [SMILES: NC(=O)c1cnc(N[C@@H]2CCC[C@H](O)C2)nc1NC12CC(C1)C2]

4-(Bicyclo[1.1.1]pentan-1-ylamino)-2-chloropyrimidine-5-carboxamide

A mixture of 2,4-dichloro-pyrimidine-5-carboxamide (2 g), bicyclo[1.1.1]pentan-1-amine hydrochloride (1.18 g), sodium bicarbonate (1.75 g), and NMP (10 mL) was stirred at 25° C. for 24 h. Water (10 mL) was charged maintaining the reaction temperature less than 30° C., and the mixture was stirred at 25° C. for 2 h. The suspension was filtered, and washed with NMP:water (1:1 10 mL), then water (2×10 mL), and dried in a vacuum oven at 40° C. with nitrogen sweep to give 4-(bicyclo[1.1.1]pentan-1-ylamino)-2-chloropyrimidine-5-carboxamide as a white solid (1.97 g, 83% yield). $^1$H NMR (DMSO-d$_6$) δ 2.14 (s, 6H), 2.51-2.53 (m, 1H), 7.76 (br. s., 1H), 8.23 (br. s., 1H), 8.60 (s, 1H), 9.57 (s, 1H).

4-(Bicyclo[1.1.1]pentan-1-ylamino)-2-(((1R,3S)-3-hydroxycyclohexyl)amino)pyrimidine-5-carboxamide A mixture of 4-(bicyclo[1.1.1]pentan-1-ylamino)-2-chloropyrimidine-5-carboxamide (44 g), (1S,3R)-3-aminocyclohexanol (27.6 g), potassium carbonate (38.2 g) and DMSO (300 mL) was heated at 85° C. for 12 h. After cooling to room temperature, water (2 L) and a mixture of THF and EtOAc (1:1, 2 L) were added. The aqueous phase was separated and the organic layer was washed with saturated brine (2 L). The organic layer was concentrated under reduced pressure to give the crude product as a purple foam which was triturated with hot acetonitrile (1 L). After cooling to room temperature the solid was filtered and washed with acetonitrile (200 mL). The solids was dried in a vacuum oven at 50° C. to give 4-(bicyclo[1.1.1]pentan-1-ylamino)-2-(((1R,3S)-3-hydroxycyclohexyl)amino)pyrimidine-5-carboxamide as an off-white solid (4 g, 79% yield). $^1$H NMR (DMSO-d$_6$) δ 0.91-1.31 (m, 4H), 1.60-1.89 (m, 3H), 2.01-2.20 (m, 7H), 3.34 (s, 1H), 3.37-3.52 (m, 1H), 3.58-3.85 (m, 1H), 4.65 (d, J=4.3 Hz, 1H), 6.90 (br. s., 1H), 7.20 (d, J=7.9 Hz, 1H), 7.61 (br. s., 1H), 8.37 (s, 1H), [9.23 (s, 0.14H)], 9.41 (s, 0.86H).

Example 4

2-(tert-butylamino)-4-((1R,3R,4R)-3-hydroxy-4-methylcyclohexylamino)-pyrimidine-5-carboxamide

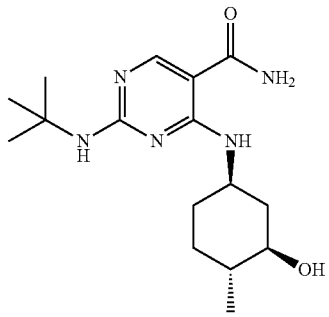 [SMILES: C[C@@H]1CC[C@@H](Nc2nc(NC(C)(C)C)ncc2C(N)=O)C[C@H]1O]

A mixture of 2-chloro-4-((1R,3R,4R)-3-hydroxy-4-methylcyclohexylamino)pyrimidine-5-carboxamide (4 g), tert-butylamine (14 mL) and DMSO (20 mL) was heated to 68° C. and held for 60 hours. After cooling to room temperature, water (20× vol, 80 mL) was added over 2 hours. The slurry was agitated for 2 hours and the crude product was collected as the DMSO hemi-solvate of 2-(tert-butylamino)-4-((1R,3R,4R)-3-hydroxy-4-methylcyclohexylamino)-pyrimidine-5-carboxamide (Form H) by suction filtration.

Example 5

Route 1 for synthesis of (1R,2R,5R)-5-amino-2-methylcyclohexanol and its HCl salt

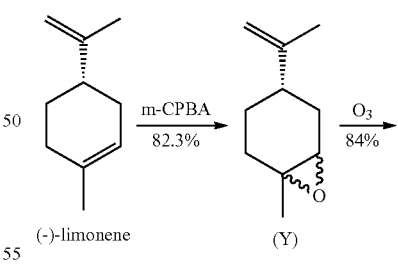

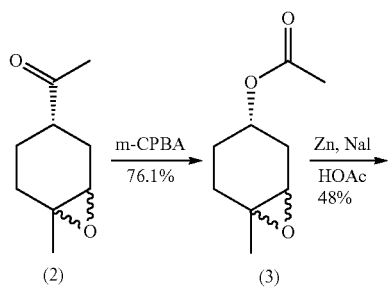

-continued

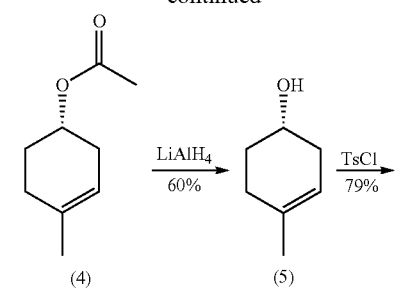

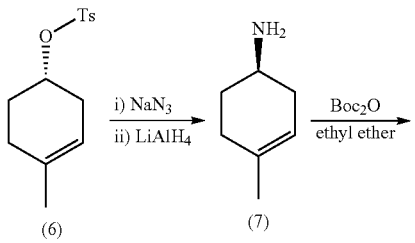

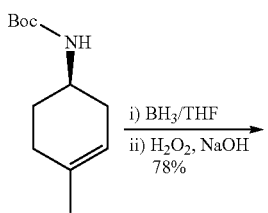

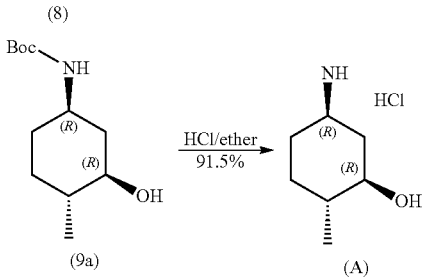

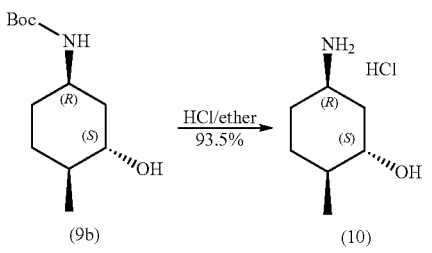

Route 1 has been used to make (1R,2R,5R)-5-amino-2-methylcyclohexanol and its HCl salt starting from Limonene. Epoxidation of (−)-Limonene with m-CPBA yielded compound (Y). Cleavage of the double bond in compound (Y) with O₃, followed by Baeyer-Villiger oxidation provided compound (3). The epoxide of compound (3) was converted back to the alkene (4). Reductive hydrolysis of the acetyl group in compound (4) gave alcohol (5). The chiral center of compound (5) was inverted by a sequence of tosylation, azide addition, and reduction, to give compound (7). Protection of compound (7) with Boc₂O yielded compound (8). The trans hydroxyl group was installed by hydroboration/oxidation of compound (8) to give a 1:1 mixture of diastereomers of compound (9a) and (9b). The diastereomers were separated by chiral SFC to give compound (9a). Deprotection of compound (9a) with acid, such as HCl, provided (1R,2R,5R)-5-amino-2-methylcyclohexanol HCl salt (A).

Example 6

Route 2 for synthesis of (1R,2R,5R)-5-amino-2-methylcyclohexanol and its HCl salt

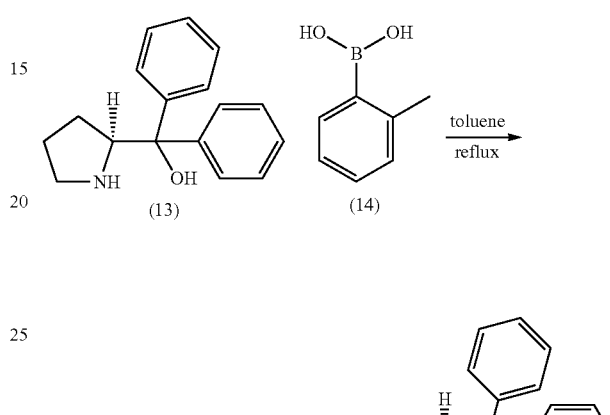

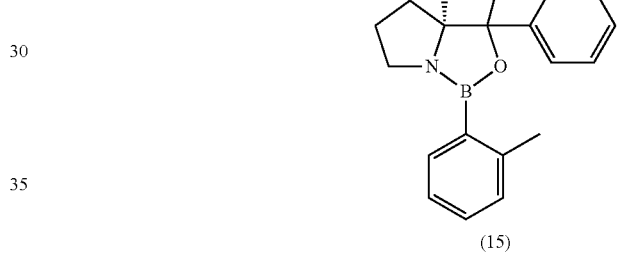

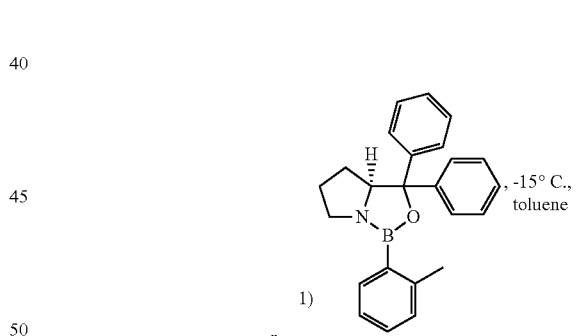

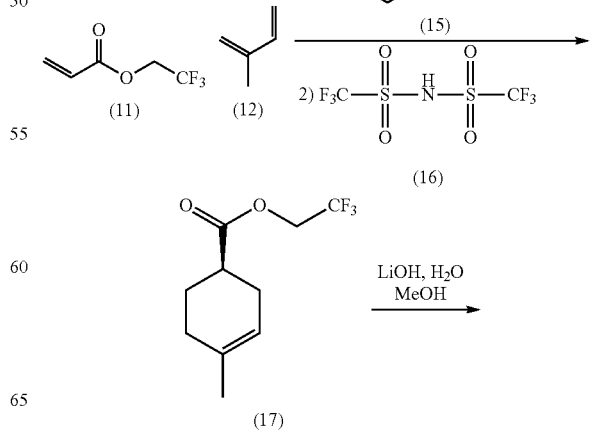

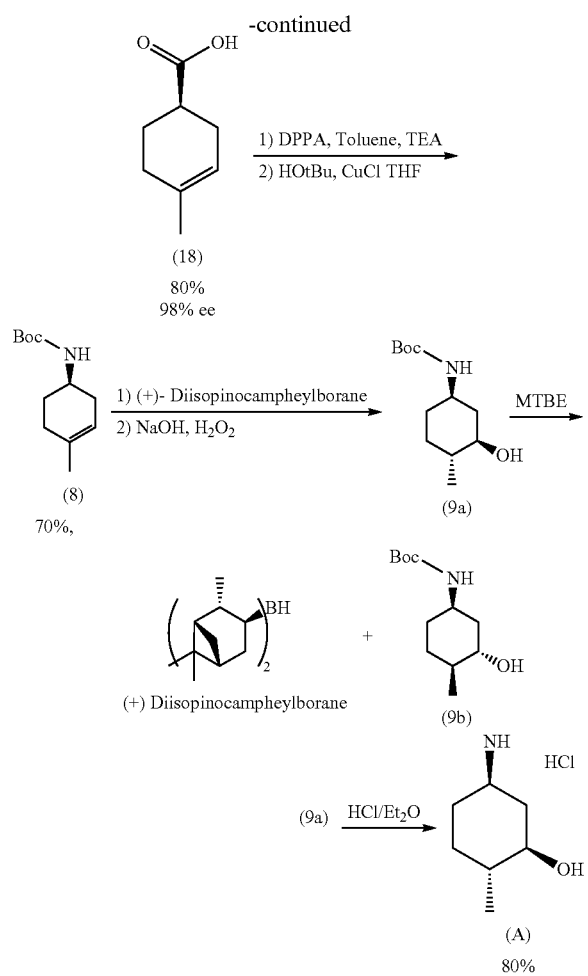

Route 2 was used to make (1R,2R,5R)-5-amino-2-methylcyclohexanol and its HCl salt starting from isoprene. Route 2 shares a common intermediate compound (8) as in Route 1. Asymmetric Diels-Alder reaction of isoprene (12) and ester (11) in the presence of the catalysts (15) and (16) provided compound (17) in >98% ee. Catalyst (15) was formed from the reaction of compound (13) and compound (14). Hydrolysis of compound (17) with base, such as LiOH or NaOH, afforded the acid (18). Curtis rearrangement of (18) with diphenylphosphoryl azide (DPPA), followed by t-butanol addition, led to compound (8) with retention of stereochemistry. The trans hydroxyl group was installed by hydroboration/oxidation of compound (8) to give a mixture of diastereomers of compound (9a) and (9b). When (+)-diisopinocampheylborane, which is prepared from (−)-alfapinene and borane-methyl sulfide, was used as a hydroboration agent, a ratio of 5-8:1 of compound 9a and 9b was obtained. The diastereomers were separated by recrystallization with MTBE to give compound 9a. Deprotection of compound 9a with acid provided (1R,2R,5R)-5-amino-2-methylcyclohexanol HCl salt (A). The enantiomeric purity could be further enhanced by recrystallization in 2-propanol.

Several reaction conditions affected the enantio-selectivity during the formation of compound (17):

Triflimide (16) load: The load of triflimide (16) must be less than the load of catalyst (15). As shown in the table below, enantio-selectivity and conversion was high with excess catalyst (15) relative to triflimide (16), such as 0.3 eq:0.2 eq, 0.24 eq:0.20 eq, and 0.24 eq:0.15 eq respectively. However, charging just 0.05 eq of triflimide to above completed reactions resulted in compound (17) in various % ee. While the total amount of triflimide (16) is lower than catalyst (15) as in column 1 and 2, no erosion of ee was observed. While the total amount of triflimide (16) was higher than catalyst (15) as in column 3 and 4, the ee of compound (17) decreased to 50% within one hour and then to 0% after 2.5 h. While the quantity of catalyst (15), (0.18 eq) was lower than triflimide (16) (0.20 eq) in the beginning of the reaction, compound (17) has 50% ee at 1 h time point, and is completely racemized after 16 h. (column 5).

| Compound (15) | 0.24 eq | 0.30 eq | 0.24 eq | 0.24 eq | 0.18 eq |
|---|---|---|---|---|---|
| triflimide (16) | 0.15 eq | 0.20 eq | 0.20 eq | 0.20 eq | 0.20 eq |
| additive | n/a | n/a | 3% prolinol (13) | 5% boronic acid (14) | n/a |
| conversion (% e.e.) | 100 (98%) | 100 (98%) | 100 (98%) | 100 (98%) | 100 (0%) |
| Triflimide (16) added | 0.05 eq | 0.05 eq | 0.05 eq | 0.05 eq | |
| % e.e. 1 h 0° C. | 98% | 98% | 50% | 50% | |
| % e.e. 2.5 h rt | 98% | 98% | 0% | 0% | |

Catalytic load: The load of catalyst (15) was between 5-20% mole. When the reaction was preformed at −20° C., compound (17) has 99% ee irrespective of the catalyst load.

| Catalyst (15) (% mole) | Reaction time (h) | Conversion (%) | Solution yield (%) | Compound (17) % ee |
|---|---|---|---|---|
| 20 | 9 | 98 | 83 | 99 |
| 10 | 18 | 97 | 84 | 99 |
| 5 | 24 | 94 | 82 | 99 |

Reaction temperature: Higher reaction temperature led to lower enantio-selectivity. It is preferred to run the reaction below −20-0° C. in order to obtain the % ee>98%.

| Reaction Temperature | Compound (17) % ee |
|---|---|
| −20° C. | 99 |
| 0° C. | 98 |
| 20° C. | 97 |

Example 7

Route 3 for synthesis of (1R,2R,5R)-5-amino-2-methylcyclohexanol and its HCl salt

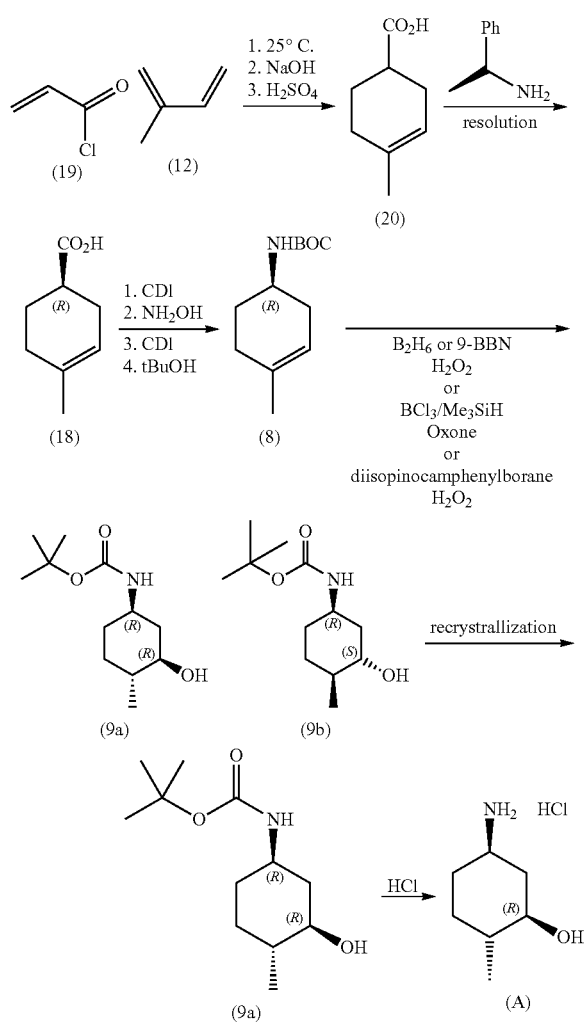

Route 3 can be used to make (1R,2R,5R)-5-amino-2-methylcyclohexanol and its HCl salt starting from isoprene. Diels-Alder reaction of isoprene and acryl chloride (19) gives the racemic compound (20). Resolution of compound (20) with a chiral amine, such as (S)- or (R)-phenylethanamine, affords enantiomerically enriched acid (18). Following the procedure of Route 2, Curtis rearrangement of (18) leads to compound (8) with retention of stereochemistry. Other reagents other than diphenylphosphoryl azide, such as CDI/NH₂OH/tBuOH can be used in the Curtis rearrangement reaction. The trans hydroxyl group is installed by hydroboration/oxidation of compound (8) to give a mixture of diastereomers of compound (9a) and (9b). When diisopinocampheylborane is used as hydroboration agent, a ratio of ~5-8:1 of compound (9a) and (9b) is obtained. The diastereomers are separated by recrystallization with MTBE to give compound (9a). Deprotection of compound (9a) with acid, such as HCl, provides (1R,2R,5R)-5-amino-2-methylcyclohexanol HCl salt (A).

Example 8

Route 4 for synthesis of (1R,2R,5R)-5-amino-2-methylcyclohexanol and its HCl salt

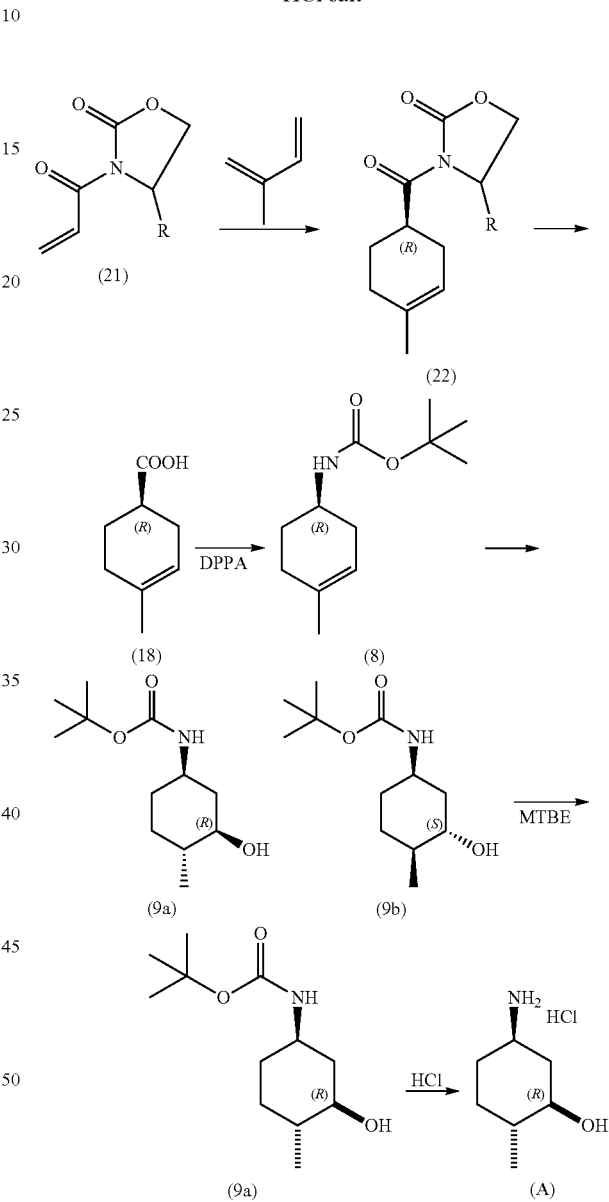

Route 4 can be used to make (1R,2R,5R)-5-amino-2-methylcyclohexanol and its HCl salt starting from isoprene. Diels-Alder reaction of chiral compound (21) (R=iPr, CH₂Ph) and isoprene gives compound (22). Hydrolysis of compound (22) gives the intermediate compound (18). Curtis rearrangement of (18) gives (8) as in route 2. The trans hydroxyl group is installed by hydroboration/oxidation of compound (8) to give a mixture of diastereomers of compound (9a) and (9b). When (+)-diisopinocampheylborane is used as hydroboration agent, a ratio of ~5-8:1 of compound (9a) and (9b) is obtained. The diastereomers are separated by recrystallization with MTBE to give compound (9a). Deprotection of compound 5 with acid provides (1R,2R,5R)-5-amino-2-methylcyclohexanol HCl salt (A).

Example 9

Route 5 for synthesis of (1R,2R,5R)-5-amino-2-methylcyclohexanol and its HCl salt

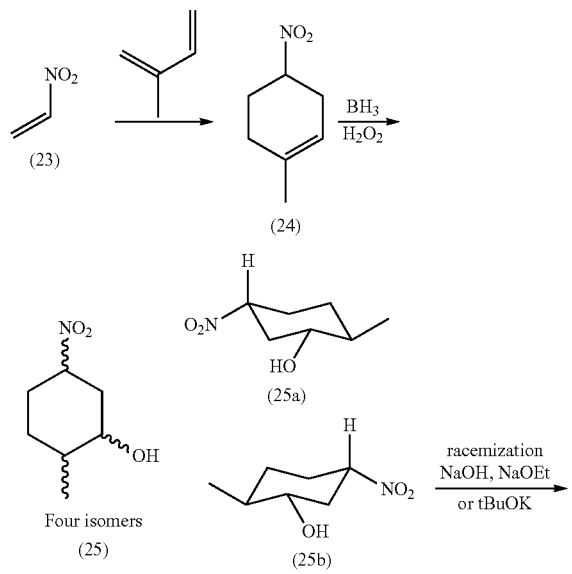

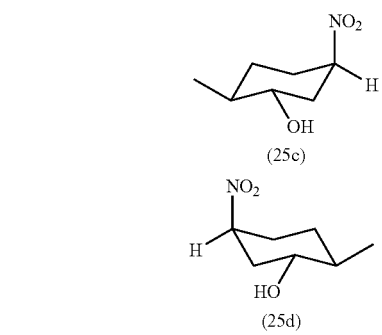

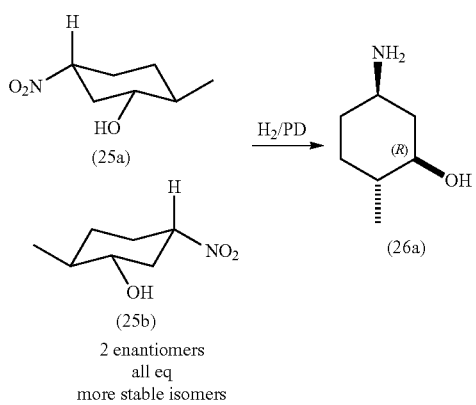

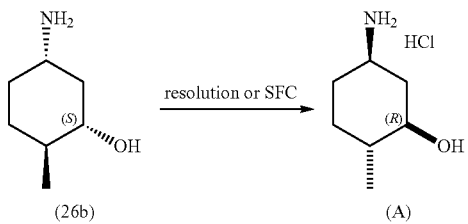

Route 5 can be used to make (1R,2R,5R)-5-amino-2-methylcyclohexanol and its HCl salt starting from nitroethene (23) and isoprene. Diels-Alder reaction of nitroethene (23) and isoprene gives the racemic compound (24). The trans hydroxyl group is installed by hydroboration/oxidation of compound (24) to give a mixture of four diastereomers (25 a-d). The diastereomers (25) are treated with base, such as NaOH, NaOEt or KOtBu, to give a mixture of two enantiomers (25a) and (25b). Reduction of the nitro group of (25a) and (25b) gives amines (26a) and (26b). Compounds (26a) and (26b) are separated by resolution or chiral SFC to give (1R,2R,5R)-5-amino-2-methylcyclohexanol or its HCl salt (A).

Example 10

Route 6 for synthesis of (1R,2R,5R)-5-amino-2-methylcyclohexanol and its HCl salt

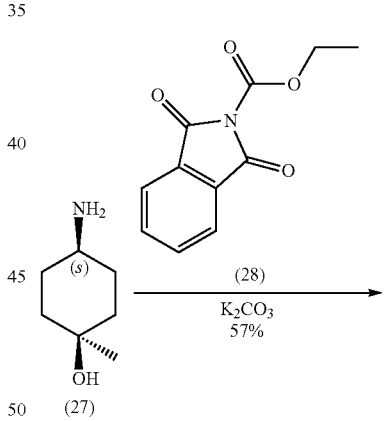

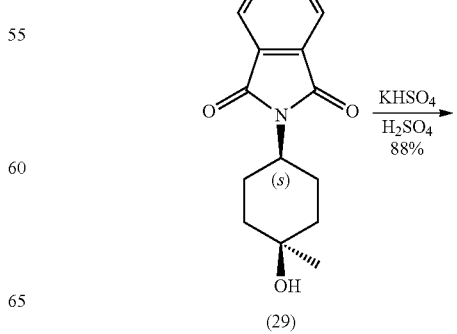

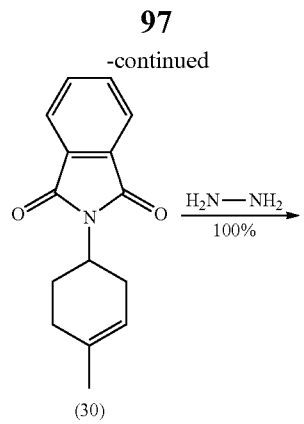

(30)

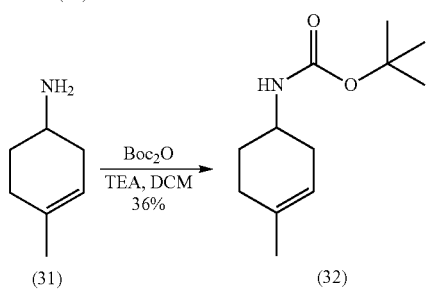

(31) (32)

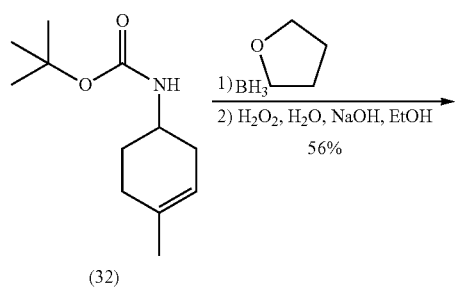

(32)

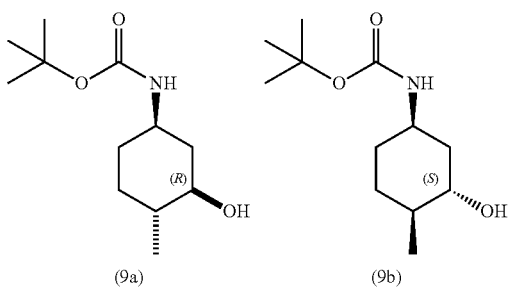

(9a) (9b)

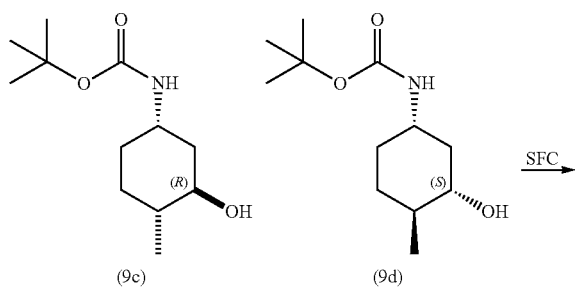

(9c) (9d)

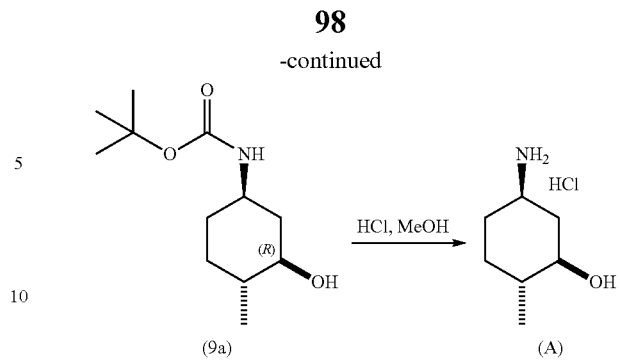

(9a) (A)

Route 6 can be used to make (1R,2R,5R)-5-amino-2-methylcyclohexanol and its HCl salt starting from amine (27). As described in International Patent Application publication WO2012/145569, protection of the amine (27) with compound (28) gave phthalimide (29). Dehydration with acid, such as $H_2SO_4$/$KHSO_4$ gave alkene (30). Deprotection of (30) afforded amine (31). The amine was protected to give the racemic (32). The trans hydroxyl group was installed by hydroboration/oxidation of compound (32) to give a mixture of four diastereomers (9 a-d). Compound 9a is purified by chiral SFC as described in route 1. Deprotection of compound 9a with acid, such as HCl, provides (1R,2R,5R)-5-amino-2-methylcyclohexanol HCl salt (A).

Example 11

Route 7 for synthesis of (1R,2R,5R)-5-amino-2-methylcyclohexanol and its HCl salt

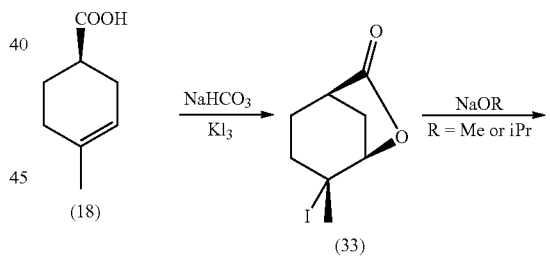

(18) (33)

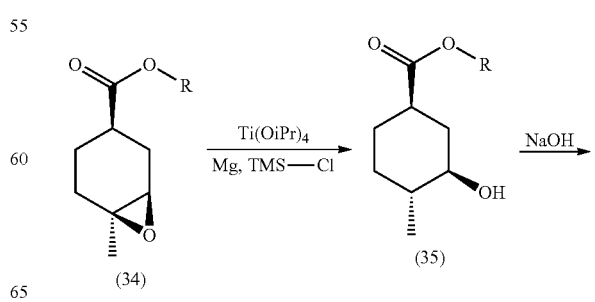

(34) (35)

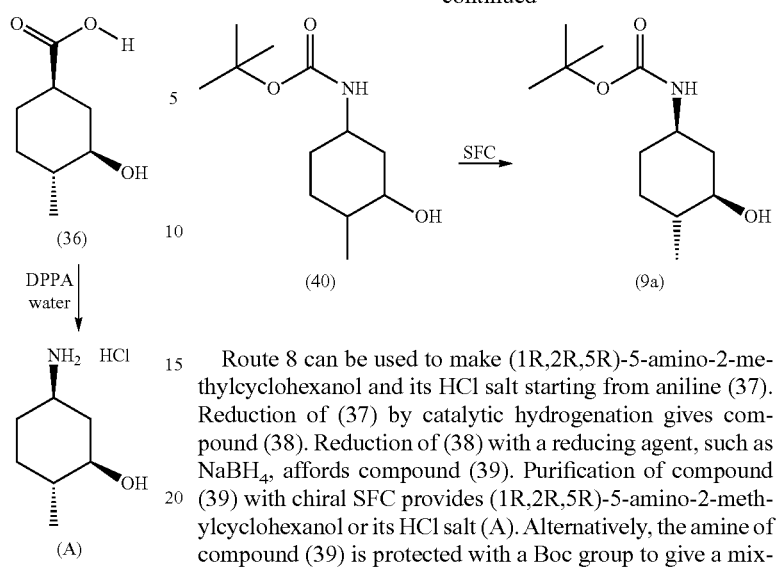

Route 7 can be used to make (1R,2R,5R)-5-amino-2-methylcyclohexanol and its HCl salt starting from (R)-acid (18), which could be prepared as described in Route 2. Iodolactonization of (18) gives lactone (33). Reaction of (33) with an alkoxide, such as NaOMe or NaOiPr, provides epoxide (34). The epoxide is opened by Ti(OiPr)$_4$/Mg/TMSCl to give (35). Hydrolysis of (35), then followed by Curtis rearrangement of (36) affords (1R,2R,5R)-5-amino-2-methylcyclohexanol or its HCl salt.

Example 12

Route 8 for synthesis of (1R,2R,5R)-5-amino-2-methylcyclohexanol and its HCl salt

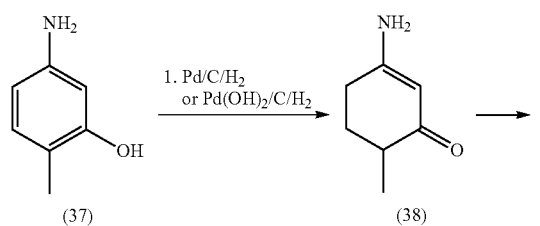

Route 8 can be used to make (1R,2R,5R)-5-amino-2-methylcyclohexanol and its HCl salt starting from aniline (37). Reduction of (37) by catalytic hydrogenation gives compound (38). Reduction of (38) with a reducing agent, such as NaBH$_4$, affords compound (39). Purification of compound (39) with chiral SFC provides (1R,2R,5R)-5-amino-2-methylcyclohexanol or its HCl salt (A). Alternatively, the amine of compound (39) is protected with a Boc group to give a mixture of diastereomers (40). Compound (40) is purified by chiral SFC to give compound (9a). Deprotection of compound (9a) with an acid such as HCl provides (1R,2R,5R)-5-amino-2-methylcyclohexanol HCl salt (A).

Example 13

Route 9 for synthesis of (1R,2R,5R)-5-amino-2-methylcyclohexanol and its HCl salt

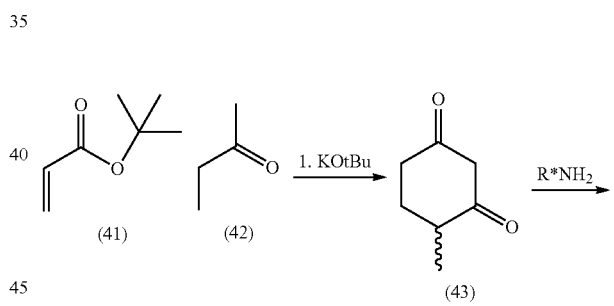

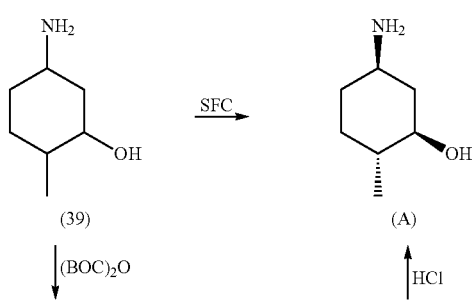

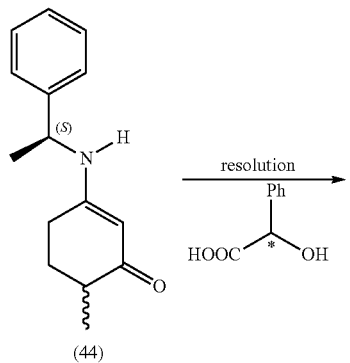

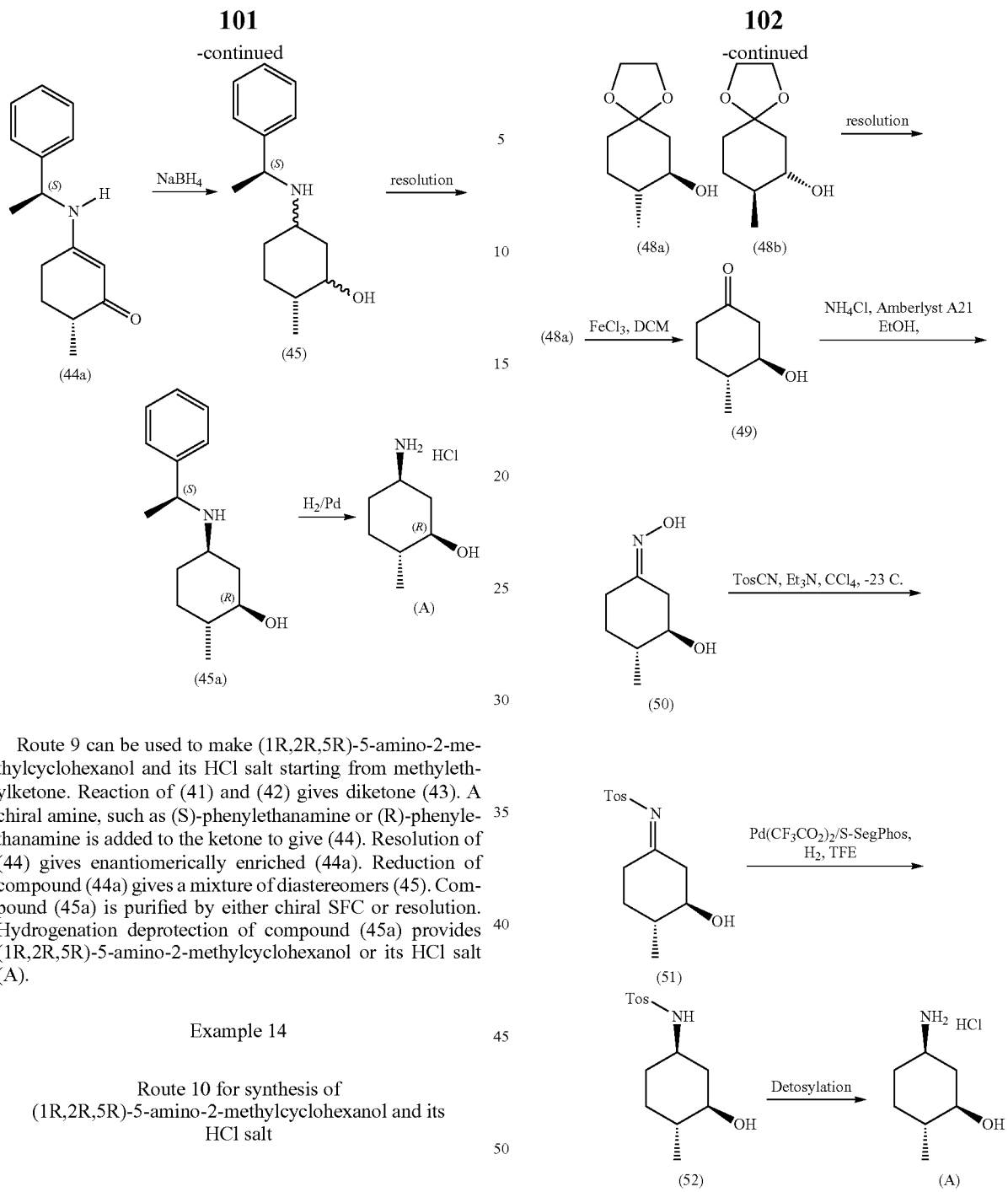

Route 9 can be used to make (1R,2R,5R)-5-amino-2-methylcyclohexanol and its HCl salt starting from methylethylketone. Reaction of (41) and (42) gives diketone (43). A chiral amine, such as (S)-phenylethanamine or (R)-phenylethanamine is added to the ketone to give (44). Resolution of (44) gives enantiomerically enriched (44a). Reduction of compound (44a) gives a mixture of diastereomers (45). Compound (45a) is purified by either chiral SFC or resolution. Hydrogenation deprotection of compound (45a) provides (1R,2R,5R)-5-amino-2-methylcyclohexanol or its HCl salt (A).

Example 14

Route 10 for synthesis of (1R,2R,5R)-5-amino-2-methylcyclohexanol and its HCl salt Route 10 can be used to make (1R,2R,5R)-5-amino-2-methylcyclohexanol and its HCl salt starting from compound (46). Ketal formation followed by epoxidation of (46) gives (47). The trans alcohol is installed by opening the epoxide with AlMe$_3$/MeLi to give (48a) and (48b). Compound (48a) is purified by either chiral SFC or resolution. Deprotection of (48a) gives ketone (49). Reaction of (49) with hydroxylamine produces hydroxylimine (50). Tosylation of (50) gives tosylimine (51). Asymmetric reduction of (51) with Pd(CF$_3$CO$_2$)$_2$/S-SegPhos/H$_2$/TFE or other chiral catalysts, gives the tosylamine (52). Deprotection of compound (52) provides (1R,2R,5R)-5-amino-2-methylcyclohexanol or its salt (A).

Solid Forms

Analytical Methods

A polymorph screen of Compound 1 was performed to investigate whether different solid forms could be generated under various conditions, such as different solvents, temperature and humidity changes.

The solvents used in the polymorph screen were either HPLC or reagent grade, including n-BuOH, acetone, ACN, ACN/water, DCM, DMSO, EtOAc, EtOH, EtOH/water, heptane, heptanes, IPA, MEK, MeOH, MTBE, THF, THF/water, toluene and water.

All of solid samples generated in the polymorph screen were analyzed by XRPD. XRPD analysis was conducted on a PANalytical Empyrean or a Thermo ARL X'TRA X-ray powder diffractometer using Cu Kα radiation at 1.54 Å.

The PANalytical Empyrean instrument was equipped with a fine focus X-ray tube. The voltage and amperage of the X-ray generator were set at 45 kV and 40 mA, respectively. The divergence slits were set at 1/16° and 1/8°, and the receiving slits was set at 1/16°. Diffracted radiation was measured using a Pixel 2D detector. A theta-two theta continuous scan was set at step size 0.013 or 0.026 from 3° to 40° 2θ with sample spinning rate at 4. A sintered alumina standard was used to check the peak positions.

The Thermo ARL X'TRA instrument was equipped with a fine focus X-ray tube. The voltage and amperage of the X-ray generator were set at 45 kV and 40 mA, respectively. The divergence slits were set at 4 mm and 2 mm and the measuring slits were set at 0.5 mm and 0.2 mm. Diffracted radiation was measured using a Peltier-cooled Si (Li) solid-state detector. A theta-two theta continuous scan at 2.40°/min (0.5 sec/0.02° step) from 1.5° to 40° 2θ was used. A sintered alumina standard was used to check the peak positions.

DSC analyses were performed on a TA Discovery Differential Scanning calorimeter. Indium was used as the calibration standard. Approximately 2-5 mg of sample was placed into a DSC pan. The sample was heated under nitrogen at a rate of 10° C./min, up to a final temperature of 300° C. Melting points were reported as the extrapolated onset temperatures.

TGA analyses were performed on a TA Discovery Thermogravimetric Analyzer. Calcium oxalate was used for a performance check. Approximately 2-10 mg of accurately weighed sample was placed on a pan and loaded into the TGA furnace. The sample was heated under nitrogen at a rate of 10° C./min, up to a final temperature of 300° C.

Morphology analysis of the samples was carried out on an Even Mini SEM. Small amounts of samples were dispersed on a sample holder, and then coating with gold and viewed with 500× magnification.

Hygroscopicity was determined on a Surface Measurement Systems DVS. Typically a sample size of 5-20 mg was loaded into the DVS instrument sample pan and the sample was analyzed on a DVS automated sorption analyzer at room temperature. The relative humidity was increased from 0% to 90% RH at 10% RH step, then at 95% RH. The relative humidity was then decreased in a similar manner to accomplish a full adsorption/desorption cycle.

$^1$H NMR spectra were obtained on a Bruker 300 MHz NMR spectrometer. Samples were dissolved in DMSO-$d_6$ and analyzed with 32 scans.

Equilibration/Slurry and Evaporation Experiments

Equilibration (also referred to as slurry experiments) and evaporation experiments were carried out by adding an excess of Compound 1 to up to 2 mL of a test solvent. The resulting mixture was agitated for at least 24 h at room temperature and 50° C. separately. Upon reaching equilibrium, the saturated supernatant solution was removed, filtered using 0.45 μm PTFE filters and allowed to evaporate in an open vial under nitrogen at room temperature and 50° C., respectively. The solid resulting from the equilibration was isolated and air-dried before analysis.

Equilibration experiments were performed at room temperature and 50° C. using Form A as starting material. The results are summarized in Table 1. The solids isolated from MTBE, heptanes and water were confirmed to be Form A by XRPD patterns. All other solvents afforded new forms. The solids isolated from acetone, DCM, THF and THF/water were designated as Form B. The solid isolated from EtOH/water, EtOH, ACN, ACN/water and IPA were designated as Form C. The solids isolated from MeOH were designated as Form D. The solids isolated from n-BuOH were designated as Form E. The solids isolated from toluene were designated as Form F. The solids isolated from EtOAc were designated as Form G. The solids isolated from DMSO were designated as Form H. All forms besides Form A were found to solvate during further characterization.

TABLE 1

Equilibration Experiments of Form A at Room Temperature and 50° C.

| Solvent | Form by XRPD | |
|---|---|---|
| | RT | 50° C. |
| Acetone | B | A + B |
| ACN | C | C |
| ACN/H$_2$O (1:1) | C | C |
| n-BuOH | E | — |
| EtOH | C | — |
| EtOH/H$_2$O (1:1) | C | — |
| MeOH | D | — |
| IPA | C | — |
| EtOAc | G | — |
| MEK | C | B |
| DCM | B | — |
| MTBE | A | A |
| Heptane | A | A |
| Toluene | F | F |
| THF | B | — |
| THF/H$_2$O (1:1) | B | — |
| H$_2$O | A | A |

—: not performed

Evaporation experiments were performed at room temperature and 50° C. The results are summarized in Table 2. The solvents that showed enough solubility for Form A afforded similar solvate forms as observed during the equilibration experiments.

TABLE 2

Evaporation Experiments of Form A at Room Temperature and 50° C.

| Solvent | Form by XRPD | |
|---|---|---|
| | RT | 50° C. |
| Acetone | — | — |
| ACN | — | — |
| ACN/H$_2$O (1:1) | C | C |
| n-BuOH | — | E |
| EtOH | C | C |
| EtOH/H$_2$O (1:1) | C | A |

TABLE 2-continued

Evaporation Experiments of Form A at Room Temperature and 50° C.

| Solvent | Form by XRPD | |
|---|---|---|
| | RT | 50° C. |
| MeOH | D | D |
| IPA | C | C |
| EtOAc | G | G |
| MEK | — | — |
| DCM | — | — |
| MTBE | — | — |
| Heptane | — | — |
| Toluene | — | — |
| THF | B | B |
| THF/H$_2$O (1:1) | B | B |
| H$_2$O | — | — |

—: Not analyzable

Anti-Solvent Recrystallization and Cooling Recrystallization Experiments

For cooling recrystallization, each of the selected solvents (MeOH, EtOH, EtOH/water) was saturated with Compound 1 at 60° C. The solution was stirred at 60° C. for 10 minutes, filtered using a 0.45 μm PTFE syringe filter, and then cooled to room temperature naturally and then placed into a refrigerator. The solid resulting from the recrystallization was isolated and air-dried before analysis.

For anti-solvent recrystallization, the selected solvents (MeOH, EtOH, IPA, and EtOAc) were saturated with Compound 1 at 60° C. Once the solid was completely dissolved, a portion of the solution was filtered into a pre-heated vial and a selected anti-solvent (water, MTBE, or heptane) was added at 60° C. The mixture was cooling to room temperature naturally and then placed into a refrigerator. The solid resulting from the recrystallization was isolated and air-dried before analysis.

MeOH, EtOH, EtOH/water, IPA, and EtOAc were used as single or primary solvents. Water, MTBE, and heptanes were used as anti-solvent. The results are summarized in Table 3. Only crystallizations using water as anti-solvents generated Form A. All other solvents or solvent combinations afforded similar solvate forms as observed during equilibration experiment.

TABLE 3

Summary of Recrystallization Experiments.

| Primary solvent | Anti-Solvent | Solvent ratio | Form by XRPD |
|---|---|---|---|
| MeOH | n/a | n/a | D |
| EtOH | n/a | n/a | C |
| EtOH/H$_2$O (1:1) | n/a | n/a | C |
| MeOH | water | 1:9 | A |
| MeOH | MTBE | 1:9 | D |
| EtOH | water | 1:9 | A |
| EtOH | MTBE | 1:9 | A + C |
| EtOH | heptane | 1:9 | C |
| EtOH | ACN | 1:9 | C |
| IPA | heptane | 1:9 | A + B + C |
| EtOAc | MTBE | 1:9 | G |
| EtOAc | heptane | 1:9 | G | n/a: not applicable.

Additional experiments were performed using DMSO as the primary solvent. The solids isolated were found to be a new form and designated as Form H.

Conversion Experiments

Further form conversion experiments were performed to determine interconversion among solid forms. The results are summarized in Table 4. The solvated forms were isothermally held at 150° C. for 5 min and the resulted solids were consistent with Form A. All aqueous slurries also afforded Form A.

TABLE 4

Converstion Experiments of Compound 1

| Starting Solid Form (s) | Solvent/ Condition | Temperature/Condition | XRPD Result |
|---|---|---|---|
| Form B | Heating | Isothermal hold at 150° C. for 5 min | Form A |
| Form C | Heating | Isothermal hold at 150° C. for 5 min | Form A |
| Form D | Heating | Isothermal hold at 150° C. for 5 min | Form A |
| Form E | Heating | Isothermal hold at 150° C. for 5 min | Form A |
| Form F | Heating | Isothermal hold at 150° C. for 5 min | Form A |
| Form G | Heating | Isothermal hold at 150° C. for 5 min | Form A |
| Form H | Heating | Isothermal hold at 150° C. for 5 min | Form A |
| Form B | Slurry in water | RT, 5 days | Form A |
| Form C | Slurry in water | RT, 5 days | Form A |
| Form D | Slurry in water | RT, 5 days | Form A |
| Form E | Slurry in water | RT, 5 days | Form A |
| Form F | Slurry in water | RT, 5 days | Form A |
| Form G | Slurry in water | RT, 5 days | Form A |
| Form H | Slurry in water | RT, 5 days | Form A |

Summary of Polymorphic Forms

Figure 37:
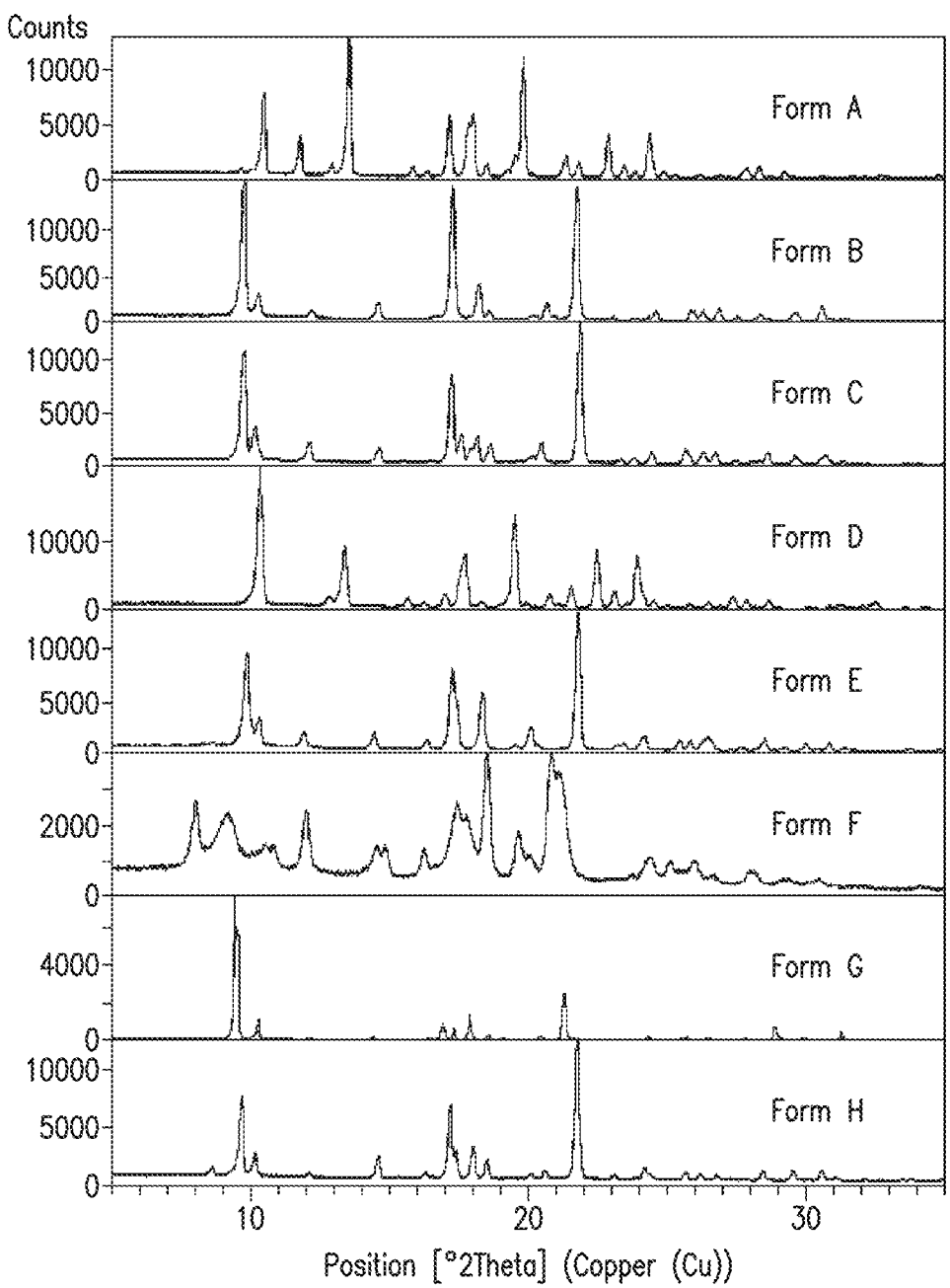
FIG. 37 depicts an overlay of XRPD patterns of Form A, Form B, Form C, Form D, Form E, Form F, Form G and Form H.

A total of eight crystalline forms for Compound 1 were found during this polymorph screen study. The stack plot of XRPD patterns for these forms are shown in FIG. 37, and the physical characteristics are summarized in Table 5.

TABLE 5

Summary of Physical Characterization of Compound 1 Crystalline Forms.

| Form | Description | Representative conditions | DSC onset or peak (° C.) | TGA loss (wt %) | DVS or other comments |
|---|---|---|---|---|---|
| A | non-stoichiome- | Rx from water-rich solvent system | 223 (onset) | 0.5 | 1.2 wt % water uptake at from |

TABLE 5-continued

Summary of Physical Characterization of Compound 1 Crystalline Forms.

| Form | Description | Representative conditions | DSC onset or peak (° C.) | TGA loss (wt %) | DVS or other comments |
|---|---|---|---|---|---|
| | tric channel hydrate | | | | 0 to 95% RH; 1.0 wt % at 80% RH |
| B | solvate | Slurry or Rx from acetone (or DCM, THF) | 147 (small endo), 223 (onset) | 8.5 | n/a |
| C | solvate | Slurry or Rx from EtOH/water (or EtOH, ACN, IPA) | 143 (small endo), 224 (onset) | 7.3 | n/a |
| D | solvate | Slurry or Rx from MeOH | 171 (small endo), 223 (onset) | ~4 | n/a |
| E | solvate | Slurry in n-BuOH | 124 (small endo), 224 (onset) | 10.3 | n/a |
| F | solvate | Slurry in toluene | 113 (small endo), 223 (onset) | 6.9 | n/a |
| G | solvate | Slurry or Rx from EtOAc | 116 (small endo), 223 (onset) | 11.9 | n/a |
| H | solvate | Slurry in DMSO | 160 (small endo), 222 (onset) | 11.2 | n/a |
| I | solvate | Rx from sulfolane and water (1:1). | 118 (small endo), 213 (m.p.) | n/a | n/a |
| amorphous | | Heat treatment | Glass transition temperature: 106.6 | n/a | n/a | n/a: not available.

Form A

Form A is a non-stoichiometric channel hydrate crystalline solid form of Compound 1. This form was mostly obtained from recrystallization or slurry experiments in aqueous or "water-rich" solvent systems.

Form A can also be obtained by conversion from Form H. A mixture of crude Form H (4 g) and water (40 mL) was heated to 70° C. for 3 hours. After cooling to room temperature, the product was collected by suction filtration. The wet cake was dried in a vacuum oven at 40° C. with a nitrogen bleed for 16 hours to give 2-(tert-butylamino)-4-((1R,3R,4R)-3-hydroxy-4-methylcyclohexylamino)pyrimidine-5-carboxamide as Form A and a white solid (3.54 g, 80%).

Figure 45:
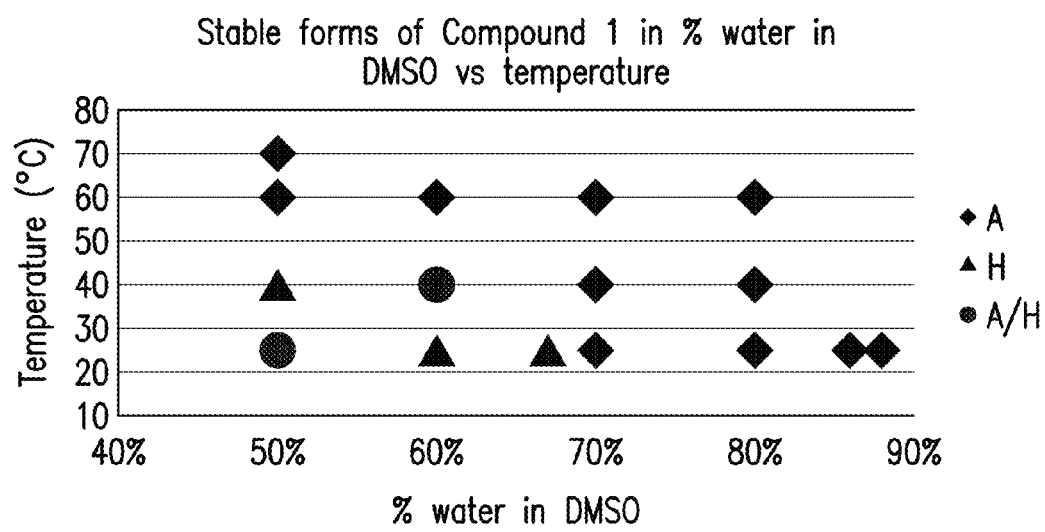
FIG. 45 depicts a form map of Forms A and H of Compound 1 in % water in DMSO vs temperature.

The effect of temperature (22° C.-70° C.) and water compositions in DMSO (50%-88%) on the stability of Form A and Form H of Compound 1 is mapped out in Table 6 and FIG. 45. This information indicates that Form A is the thermodynamically stable form in the water rich water/DMSO mixture (>70%).

TABLE 6

Stable forms after slurry experiments of Form H in ratio of water/DMSO from 50 to 88% and temperatures from 22° C. to 70° C.

| | % water in DMSO (Stable Polymorph Form) | | | | | | |
|---|---|---|---|---|---|---|---|
| Temperature | 50% | 60% | 67% | 70% | 80% | 86% | 88% |
| 70° C. | A | | | | | | |
| 60° C. | A | A | | A | A | | |
| 40° C. | H | A/H | | A | A | | |
| 22° C. | A/H | H | H | A | A | A | A |

Form A was favored at 60° C. from 1:1 (50% water) to 1:4 DMSO:Water (80% water) and remained as Form A at 22° C. in 70-88% water in DMSO. 70% water in DMSO was at the edge of the Form conversion between Form A and Form H. Therefore, the final solvent composition was selected as 80% water in DMSO. These results indicated that for a synthesis of Compound 1 employing 5× vol. of DMSO, the addition of 20× vol of water at 60° C. to the reaction mixture after reaction completion would afford Compound 1 as Form A.

Form A has a crystalline XRPD pattern as shown in FIG. 1. The crystal habit is cube-like or rod-like as shown in FIG. 2. TGA and DSC thermograms of Form A are shown in FIG. 4 and FIG. 5, respectively. The DSC thermogram showed only one major event with an onset temperature of 223° C., corresponding to melt/decomposition. TGA weight loss of 0.45% was observed up to 150° C. The $^1$H NMR spectrum of Form A was consistent with Compound 1 structure (see FIG. 7).

Figure 8:
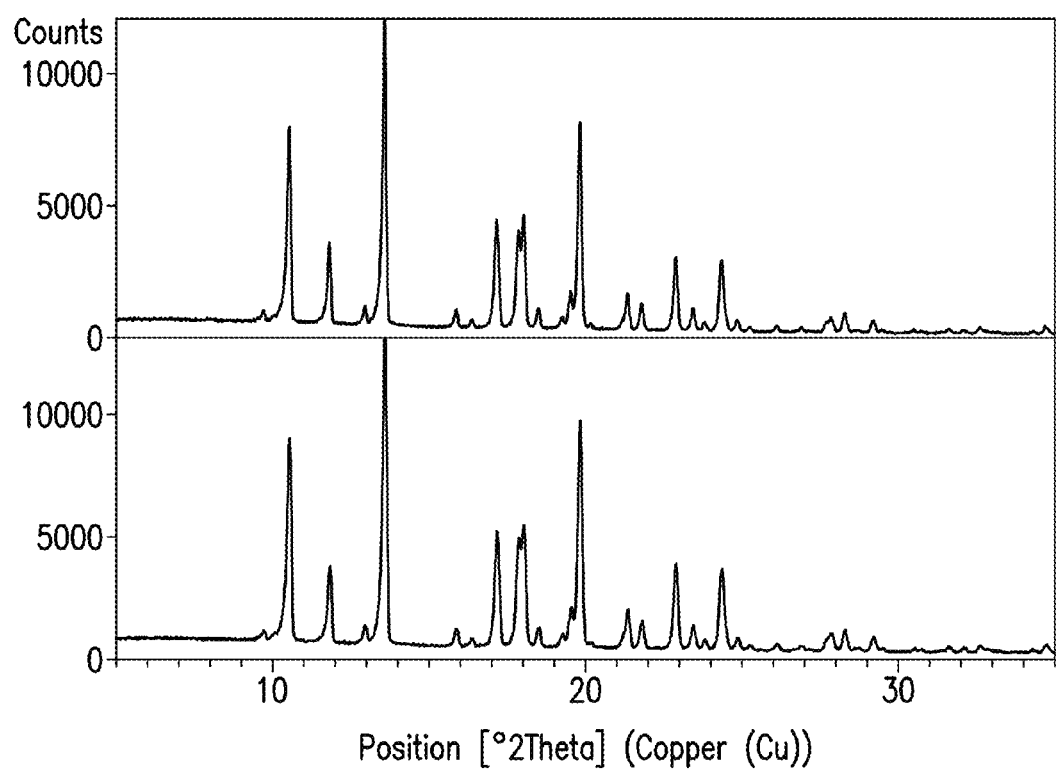
FIG. 8 depicts an overlay of XRPD patterns of Form A before and after DVS (top and bottom).

The moisture sorption/desorption behavior of Form A was determined by DVS. The results are summarized in FIG. 6. A total mass change of 2.3% was observed between 0 and 95% RH, with a steep change of 1.3% between 0 and 10% RH. After undergoing the adsorption/desorption cycles, the XRPD diffractogram of the sample showed no change (see FIG. 8). Steep change between 0 and 10% RH was observed for several samples, but the amount of water uptake varied among samples. The total water uptake between 0 and 95% RH ranged from approximately 0.5% to 2% for all Form A samples analyzed.

Further characterization using single-crystal X-ray diffraction was performed for Form A. The structure was resolved in the space group P2(1)2(1)2(1). The crystal data and structure refinement is summarized in Table 7. The power x-ray pattern was calculated and matched the experimental XRPD patterns observed for Form A, as shown in FIG. 1. Fractional occupancy of water molecules was found in the crystal lattice. Inclusion of roughly 20% of occupancy lowered the R factor from 5.2% to 3.6%. The drawing of cell packing along b-axis as shown in FIG. 2 revealed channeled water molecules in the crystal lattice. These observations suggested that Form A is a channel hydrate. The theoretical water content is 1.1 wt % for 0.2 molar equivalents of water and 2.7 wt % for 0.5 molar equivalents of water.

TABLE 7

Crystal data and structure refinement for Form A.

| | |
|---|---|
| Empirical formula | $C_{16}H_{27}N_5O_2$ (w/ ca. 0.2 $H_2O$) |
| Formula weight | 321.43 |
| Temperature | 100(2) K |
| Wavelength | 0.71073 Å |
| Crystal system | Orthorhombic |
| Space group | P2(1)2(1)2(1) |
| Unit cell dimensions | a = 10.2905(15) Å; α = 90° |
| b = 10.7755(19) Å | β = 90° |
| c = 16.557(2) Å | γ = 90° |
| Volume | 1836.0(5) Å$^3$ |
| Z | 4 |
| Density (calculated) | 1.163 g/cm$^3$ |
| Absorption coefficient | 0.079 mm$^{-1}$ |
| F(000) | 696 |
| Crystal size | 0.35 × 0.35 × 0.30 mm$^3$ |
| Theta range for data collection | 3.68 to 25.43° |
| Index ranges | −12 <= h <= 12, −12 <= k <= 12, −18 <= l <= 19 |
| Reflections collected | 7480 |
| Independent reflections | 3297 [R(int) = 0.0369] |
| Completeness to theta = 25.00° | 99.5% |
| Absorption correction | Multi-scan |
| Max. and min. transmission | 0.9766 and 0.9728 |
| Refinement method | Full-matrix least-squares on F$^2$ |
| Data/restraints/parameters | 3297/2/221 |
| Goodness-of-fit on F$^2$ | 1.046 |
| Final R indices [I > 2sigma(I)] | R1 = 0.0365, wR2 = 0.0868 |
| R indices (all data) | R1 = 0.0433, wR2 = 0.0910 |
| Absolute structure parameter | 0.8(12) |
| Largest diff. peak and hole | 0.175 and −0.170e Å$^{-3}$ |

Figure 9:
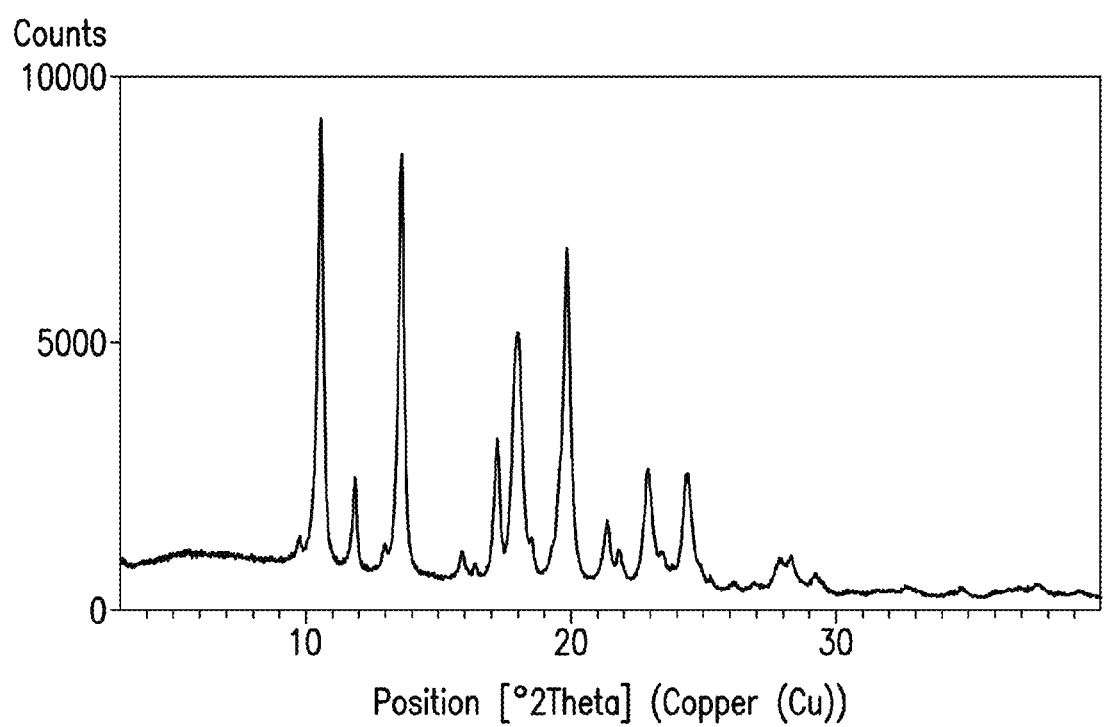
FIG. 9 depicts an XRPD pattern of Form A after compression of 2000-psi for 1 minute.

The stability of Form A was further characterized by compression test and form transfer experiments. Upon application of 2000-psi pressure for about 1 minute, the material was still Form A, with slightly broader diffraction peaks (see FIG. 9). Results from form transfer experiments in Table 4 showed that all solvate forms convert to Form A upon desolvation by heating or upon slurry in water. These results suggested that Form A is a most stable or developable form of Compound 1.

FIG. 1 provides an XRPD pattern of Form A. A list of X-Ray Diffraction Peaks for Form A is provided below in Table 8.

TABLE 8

X-Ray Diffraction Peaks for Form A

| Two-theta angle (°) | d Space (Å) | Relative Intensity (%) |
|---|---|---|
| 9.74 | 9.0811 | 3.7 |
| 10.55 | 8.3820 | 56.2 |
| 11.86 | 7.4633 | 26.2 |
| 12.98 | 6.8187 | 6.9 |
| 13.61 | 6.5079 | 100.0 |
| 15.90 | 5.5750 | 6.4 |
| 16.41 | 5.4031 | 2.9 |
| 17.20 | 5.1550 | 43.0 |
| 17.85 | 4.9706 | 31.9 |
| 18.04 | 4.9180 | 42.6 |
| 18.54 | 4.7868 | 7.8 |
| 19.29 | 4.6003 | 5.3 |
| 19.56 | 4.5386 | 15.2 |
| 19.84 | 4.4744 | 83.5 |
| 20.19 | 4.3989 | 1.8 |
| 21.37 | 4.1572 | 15.1 |
| 21.83 | 4.0715 | 10.8 |
| 22.90 | 3.8842 | 29.7 |
| 23.46 | 3.7920 | 8.5 |
| 23.84 | 3.7320 | 3.6 |
| 24.36 | 3.6537 | 30.0 |
| 24.88 | 3.5782 | 4.6 |
| 25.29 | 3.5222 | 2.3 |
| 26.14 | 3.4093 | 2.7 |
| 26.92 | 3.3120 | 2.1 |
| 27.83 | 3.2055 | 6.8 |
| 28.30 | 3.1538 | 8.8 |
| 28.69 | 3.1115 | 1.5 |
| 29.21 | 3.0574 | 5.6 |
| 30.50 | 2.9314 | 1.2 |
| 31.63 | 2.8286 | 2.1 |
| 32.11 | 2.7878 | 1.5 |
| 32.63 | 2.7444 | 2.7 |
| 33.17 | 2.7008 | 0.6 |
| 34.32 | 2.6129 | 1.1 |
| 34.74 | 2.5826 | 3.1 |
| 36.00 | 2.4950 | 1.7 |
| 36.56 | 2.4582 | 2.7 |
| 36.95 | 2.4330 | 1.8 |
| 37.26 | 2.4131 | 1.5 |
| 37.61 | 2.3918 | 3.3 |
| 38.40 | 2.3442 | 1.5 |
| 39.07 | 2.3056 | 2.7 |
| 39.34 | 2.2905 | 1.5 |
| 39.64 | 2.2739 | 1.0 |

FIG. 3 is an SEM image of Form A.

The intrinsic solubility of Form A at 25° C. after 24 h was 0.038 mg/mL and 0.289 mg/mL at pH 4.5. Although Form A is a channel hydrate, it has a relatively slow water uptake at room temperature. However, Form A may potentially absorb up to 3% water after storage at 40° C./75% RH for 7 months. The water uptake may strongly depend on the humidity of the storage conditions and therefore, it is recommended to protect Compound 1 from moisture during storage.

Form B

Form B was obtained from recrystallization or slurry experiments of Form A in acetone, $CH_2Cl_2$ or THF. Form B had a crystalline XRPD pattern as shown in FIG. 10. TGA and DSC thermograms of Form B obtained from acetone are shown in FIG. 11 and FIG. 12, respectively. The TGA weight loss of 8.5 wt % corresponded to small broad DSC peak around 147° C. and can be attributed to loss of solvent in Form B. The major DSC peak with onset temperature of 223° C. corresponded to the melt/decomposition of Form A. The $^1$H-NMR spectrum was obtained for the Form B sample and showed approximately 0.5 molar equivalents of acetone (see FIG. 13). The theoretical acetone content of a hemi-solvate of Compound 1 is 8.3 wt %, matching the TGA weight loss observed. These observations suggested that Form B is an acetone hemi-solvate of Compound 1. Form transfer experiment showed that heating Form B above the desolvation temperature resulted in Form A. Slurry of Form B in water also resulted in Form A.

A list of X-Ray Diffraction Peaks for Form B is provided below in Table 9.

TABLE 9

X-Ray Diffraction Peaks for Form B

| Two-theta angle (°) | d Space (Å) | Relative Intensity (%) |
|---|---|---|
| 9.80 | 9.0251 | 100.0 |
| 10.30 | 8.5867 | 16.4 |
| 12.23 | 7.2379 | 5.6 |
| 14.62 | 6.0604 | 10.9 |

TABLE 9-continued

X-Ray Diffraction Peaks for Form B

| Two-theta angle (°) | d Space (Å) | Relative Intensity (%) |
|---|---|---|
| 16.70 | 5.3091 | 2.0 |
| 17.29 | 5.1285 | 96.6 |
| 18.23 | 4.8654 | 25.4 |
| 18.59 | 4.7722 | 5.3 |
| 19.61 | 4.5268 | 0.6 |
| 20.19 | 4.3976 | 2.9 |
| 20.66 | 4.2992 | 11.4 |
| 20.94 | 4.2425 | 2.2 |
| 21.74 | 4.0873 | 96.5 |
| 23.03 | 3.8620 | 1.4 |
| 23.84 | 3.7327 | 1.5 |
| 24.32 | 3.6599 | 2.0 |
| 24.58 | 3.6223 | 6.0 |
| 25.88 | 3.4425 | 7.1 |
| 26.27 | 3.3924 | 6.9 |
| 26.86 | 3.3192 | 8.3 |
| 27.52 | 3.2411 | 2.4 |
| 28.35 | 3.1478 | 4.1 |
| 28.62 | 3.1190 | 1.2 |
| 29.63 | 3.0155 | 5.6 |
| 30.55 | 2.9265 | 9.9 |
| 30.87 | 2.8965 | 2.2 |
| 31.44 | 2.8459 | 1.7 |
| 32.12 | 2.7871 | 0.6 |
| 33.71 | 2.6592 | 1.2 |
| 33.95 | 2.6407 | 0.8 |
| 34.96 | 2.5667 | 1.5 |
| 35.94 | 2.4987 | 2.1 |
| 36.14 | 2.4855 | 1.3 |
| 36.56 | 2.4579 | 1.8 |
| 37.22 | 2.4156 | 0.6 |
| 38.76 | 2.3230 | 1.4 |

FIG. 13 provides a $^1$H NMR (DMSO-$d_6$) of Form B with δ 0.94 (d, J=6.4 Hz, 3H), 0.96-1.04 (m, 1H), 1.04-1.28 (m, 3H), 1.36 (s, 9H), 1.60-1.74 (m, 1H), 1.83-1.98 (m, 1H), 2.09 (s, 3H, acetone), 2.10-2.19 (m, 1H), 2.89-3.04 (m, 1H), 3.76-3.99 (m, 1H), 4.57 (d, J=5.5 Hz, 1H), 6.64 (br. s., 1H), 6.94 (br. s., 1H), 7.51 (br. s., 1H), 8.34 (s, 1H), 8.93 (br. s., 1H).

Form C

Form C was obtained from recrystallization or slurry experiments of Form A in EtOH/water, EtOH, ACN or IPA. Form C had a crystalline XRPD pattern as shown in FIG. 14. TGA and DSC thermograms of Form C obtained from EtOH/water are shown in FIG. 15 and FIG. 16, respectively. The TGA weight loss of 7.3 wt % corresponded to small broad DSC peak around 143° C. and can be attributed to loss of solvent in Form C. The major DSC peak with onset temperature of 224° C. corresponded to the melt/decomposition of Form A. The $^1$H-NMR spectrum was obtained for the Form C sample and showed approximately 0.5 molar equivalents of EtOH (see FIG. 17). The theoretical EtOH content of a hemi-solvate of Compound 1 is 6.7 wt %, matching the TGA weight loss observed. These observations suggested that Form C is an ethanol hemi-solvate of Compound 1. Form transfer experiment showed that heating Form C above the desolvation temperature resulted in Form A. Slurry of Form C in water also resulted in Form A.

A list of X-Ray Diffraction Peaks for Form C is provided below in Table 10.

TABLE 10

X-Ray Diffraction Peaks for Form C

| Two-theta angle (°) | d Space (Å) | Relative Intensity (%) |
|---|---|---|
| 9.83 | 8.9960 | 77.7 |
| 10.21 | 8.6630 | 23.0 |
| 12.16 | 7.2807 | 13.3 |
| 14.66 | 6.0419 | 9.6 |
| 15.52 | 5.7080 | 0.8 |
| 16.50 | 5.3712 | 1.4 |
| 17.26 | 5.1376 | 62.2 |
| 17.61 | 5.0354 | 19.6 |
| 17.91 | 4.9534 | 8.9 |
| 18.18 | 4.8799 | 18.5 |
| 18.65 | 4.7591 | 12.5 |
| 19.67 | 4.5133 | 1.4 |
| 19.99 | 4.4414 | 2.9 |
| 20.46 | 4.3399 | 14.2 |
| 21.86 | 4.0664 | 100.0 |
| 23.32 | 3.8151 | 2.9 |
| 23.78 | 3.7416 | 3.9 |
| 24.44 | 3.6421 | 8.4 |
| 25.65 | 3.4730 | 9.8 |
| 25.81 | 3.4520 | 5.8 |
| 26.28 | 3.3914 | 8.4 |
| 26.72 | 3.3360 | 7.9 |
| 27.46 | 3.2481 | 2.6 |
| 28.04 | 3.1820 | 1.5 |
| 28.30 | 3.1536 | 2.6 |
| 28.60 | 3.1210 | 8.3 |
| 29.56 | 3.0216 | 5.5 |
| 30.47 | 2.9342 | 3.7 |
| 30.70 | 2.9127 | 6.8 |
| 31.29 | 2.8586 | 2.3 |
| 31.77 | 2.8170 | 0.8 |
| 32.16 | 2.7830 | 0.5 |
| 32.94 | 2.7194 | 0.4 |
| 33.55 | 2.6708 | 0.9 |
| 34.00 | 2.6367 | 1.1 |
| 34.85 | 2.5744 | 0.6 |
| 35.14 | 2.5541 | 0.5 |
| 35.57 | 2.5238 | 1.9 |
| 35.90 | 2.5013 | 1.9 |
| 36.62 | 2.4542 | 2.2 |
| 37.76 | 2.3828 | 0.7 |
| 38.93 | 2.3136 | 1.1 |

FIG. 17 provides a $^1$H NMR (DMSO-$d_6$) of Form C with δ 0.94 (d, J=6.4 Hz, 3H), 1.00-1.27 (m, 5.6H) {include 1.02 (t, J=7.0 Hz, 1.6H, ethanol)}, 1.36 (s, 9H), 1.67 (dd, J=3.3, 13.1 Hz, 1H), 1.81-2.00 (m, 1H), 2.10-2.24 (m, 1H), 2.87-3.05 (m, 1H), 3.32 (s, 4H), 3.44 (qd, J=5.1, 7.0 Hz, 1H, ethanol), 3.74-3.99 (m, 1H), 4.35 (t, J=5.1 Hz, 1H), 4.57 (d, J=5.7 Hz, 1H), 6.45-6.77 (m, 1H), 6.92 (br. s., 1H), 7.51 (br. s., 1H), 8.34 (s, 1H), 8.92 (br. s., 1H).

Form D

Form D was obtained from recrystallization or slurry experiments of Form A in MeOH. Form D had a crystalline XRPD pattern as shown in FIG. 18. TGA and DSC thermograms of Form D are shown in FIG. 19 and FIG. 20, respectively. The TGA weight loss of approximately 4 wt % corresponded to small DSC peak around 170° C. and can be attributed to loss of solvent in Form D. The major DSC peak with onset temperature of 223° C. corresponded to the melt/decomposition of Form A. The $^1$H-NMR spectrum was obtained for the Form D sample and showed approximately 0.5 molar equivalents of MeOH (see FIG. 21). The theoretical MeOH content of a hemi-solvate of Compound 1 is 4.7 wt %, similar to the TGA weight loss observed. These observations suggested that Form D is most likely a methanol hemi-solvate of Compound 1. Form transfer experiment showed that heating Form D above the desolvation temperature resulted in Form A. Slurry of Form D in water also resulted in Form A.

A list of X-Ray Diffraction Peaks for Form D is provided below in Table 11.

TABLE 11

X-Ray Diffraction Peaks for Form D

| Two-theta angle (°) | d Space (Å) | Relative Intensity (%) |
|---|---|---|
| 10.37 | 8.5278 | 100.0 |
| 12.85 | 6.8897 | 6.7 |
| 13.41 | 6.6046 | 42.7 |
| 15.68 | 5.6527 | 6.5 |
| 16.25 | 5.4562 | 3.4 |
| 17.02 | 5.2108 | 9.8 |
| 17.54 | 5.0569 | 22.7 |
| 17.73 | 5.0013 | 38.0 |
| 18.34 | 4.8371 | 3.9 |
| 19.52 | 4.5474 | 65.5 |
| 19.93 | 4.4550 | 3.1 |
| 20.78 | 4.2750 | 9.7 |
| 21.09 | 4.2119 | 2.6 |
| 21.54 | 4.1252 | 14.1 |
| 22.47 | 3.9564 | 42.4 |
| 23.11 | 3.8492 | 12.0 |
| 23.55 | 3.7780 | 2.7 |
| 23.92 | 3.7207 | 37.4 |
| 24.51 | 3.6324 | 4.7 |
| 24.99 | 3.5627 | 1.3 |
| 25.81 | 3.4516 | 2.6 |
| 26.47 | 3.3669 | 4.0 |
| 26.88 | 3.3167 | 1.4 |
| 27.33 | 3.2634 | 8.3 |
| 27.83 | 3.2056 | 5.5 |
| 28.19 | 3.1659 | 1.3 |
| 28.64 | 3.1168 | 6.2 |
| 30.08 | 2.9709 | 0.7 |
| 30.82 | 2.9013 | 1.7 |
| 31.20 | 2.8667 | 3.2 |
| 31.60 | 2.8315 | 0.8 |
| 32.02 | 2.7952 | 2.2 |
| 32.50 | 2.7551 | 4.7 |
| 33.58 | 2.6692 | 1.6 |
| 34.25 | 2.6183 | 1.6 |
| 35.39 | 2.5363 | 0.6 |
| 35.87 | 2.5034 | 2.8 |
| 36.55 | 2.4588 | 1.5 |
| 36.81 | 2.4415 | 2.7 |
| 37.06 | 2.4261 | 2.1 |
| 37.77 | 2.3820 | 2.8 |
| 38.60 | 2.3323 | 1.8 |

FIG. 21 provides a $^1$H NMR (DMSO-$d_6$) of Form D with δ 0.94 (d, J=6.4 Hz, 3H), 0.96-1.04 (m, 1H), 1.05-1.28 (m, 3H), 1.36 (s, 9H), 1.67 (dd, J=3.1, 13.1 Hz, 1H), 1.84-1.97 (m, 1H), 2.08-2.20 (m, 1H), 2.86-3.04 (m, 1H), 3.17 (d, J=5.3 Hz, 1.6H, methanol), 3.76-3.99 (m, 1H), 4.09 (q, J=5.3 Hz, 1H), 4.57 (d, J=5.5 Hz, 1H), 6.65 (br. s., 1H), 6.95 (br. s., 1H), 7.47 (br. s., 1H), 8.34 (s, 1H), 8.93 (br. s., 1H).

Form E

Form E was obtained from recrystallization or slurry experiments of Form A in n-BuOH. Form E had a crystalline XRPD pattern as shown in FIG. 22. TGA and DSC thermograms of Form E are shown in FIG. 23 and FIG. 24, respectively. The TGA weight loss of 10.3 wt % corresponded to small broad DSC peak around 124° C. and can be attributed to loss of solvent in Form E. The major DSC peak with onset temperature of 224° C. corresponded to the melt/decomposition of Form A. The $^1$H-NMR spectrum was obtained for the Form E sample and showed approximately 0.5 molar equivalents of n-BuOH (see FIG. 25). The theoretical n-BuOH content of a hemi-solvate of Compound 1 is 10.3 wt %, matching the TGA weight loss observed. These observations suggested that Form E is an n-BuOH hemi-solvate of Compound 1. Form transfer experiment showed that heating Form E above the desolvation temperature resulted in Form A. Slurry of Form E in water also resulted in Form A.

A list of X-Ray Diffraction Peaks for Form E is provided below in Table 12.

TABLE 12

X-Ray Diffraction Peaks for Form E

| Two-theta angle (°) | d Space (Å) | Relative Intensity (%) |
|---|---|---|
| 8.70 | 10.1625 | 3.1 |
| 9.92 | 8.9143 | 66.8 |
| 10.36 | 8.5380 | 19.6 |
| 11.97 | 7.3945 | 10.4 |
| 14.50 | 6.1092 | 11.3 |
| 15.51 | 5.7126 | 0.9 |
| 16.39 | 5.4097 | 6.2 |
| 17.29 | 5.1283 | 55.7 |
| 18.37 | 4.8287 | 40.5 |
| 19.55 | 4.5419 | 3.0 |
| 20.10 | 4.4180 | 15.6 |
| 21.81 | 4.0760 | 100.0 |
| 23.21 | 3.8330 | 3.2 |
| 23.45 | 3.7936 | 4.6 |
| 24.17 | 3.6830 | 9.0 |
| 24.61 | 3.6175 | 1.1 |
| 25.44 | 3.5013 | 6.4 |
| 25.83 | 3.4496 | 6.6 |
| 26.23 | 3.3982 | 6.1 |
| 26.45 | 3.3701 | 9.5 |
| 26.61 | 3.3495 | 5.8 |
| 27.64 | 3.2274 | 2.4 |
| 28.48 | 3.1337 | 8.4 |
| 29.19 | 3.0593 | 2.9 |
| 29.97 | 2.9820 | 5.4 |
| 30.39 | 2.9413 | 1.3 |
| 30.81 | 2.9025 | 5.0 |
| 31.36 | 2.8530 | 2.6 |
| 31.66 | 2.8265 | 1.1 |
| 32.62 | 2.7454 | 0.6 |
| 33.67 | 2.6621 | 2.1 |
| 34.75 | 2.5819 | 1.2 |
| 35.24 | 2.5467 | 1.9 |
| 35.96 | 2.4975 | 1.7 |
| 36.48 | 2.4630 | 3.4 |
| 37.20 | 2.4169 | 0.5 |
| 37.62 | 2.3911 | 0.3 |
| 38.93 | 2.3136 | 0.6 |
| 39.20 | 2.2983 | 0.6 |

FIG. 25 provides a $^1$H NMR (DMSO-$d_6$) of Form E with δ 0.85 (t, J=7.2 Hz, 1.5H, n-butanol), 0.94 (d, J=6.4 Hz, 3H), 0.96-1.04 (m, 1H), 1.04-1.25 (m, 3H), 1.25-1.46 (m, 11H) {{include 1.36 (s, 9H), 1.3-1.46 (m, 2H, n-butanol)}, 1.67 (dd, J=3.2, 13.0 Hz, 1H), 1.81-2.00 (m, 1H), 2.10-2.24 (m, 1H), 2.86-3.05 (m, 1H), 3.35-3.44 (m, 1H, n-butanol), 3.75-3.99 (m, 1H), 4.31 (t, J=5.2 Hz, 0.5H), 4.57 (d, J=5.7 Hz, 1H), 6.65 (br. s., 1H), 6.97 (br. s., 1H), 7.53 (br. s., 1H), 8.34 (s, 1H), 8.93 (br. s., 1H).

Form F

Form F was obtained from recrystallization or slurry experiments of Form A in toluene. Form F had a crystalline XRPD pattern as shown in FIG. 26. The diffuse character of the diffraction pattern suggested low crystalline of the sample. TGA and DSC thermograms of Form F are shown in FIG. 27 and FIG. 28, respectively. The TGA weight loss of 6.9 wt % corresponded to small broad DSC peak around 113° C.

and can be attributed to loss of solvent in Form F. The major DSC peak with onset temperature of 223° C. corresponded to the melt/decomposition of Form A. The $^1$H-NMR spectrum obtained for the Form F sample showed approximately 0.3 molar equivalents of toluene (see FIG. 29), matching the TGA weight loss observed. These observations suggested that Form F is a 0.3 molar toluene solvate of Compound 1. Form transfer experiment showed that heating Form F above the desolvation temperature resulted in Form A. Slurry of Form F in water also resulted in Form A.

A list of X-Ray Diffraction Peaks for Form F is provided below in Table 13.

TABLE 13

X-Ray Diffraction Peaks for Form F

| Two-theta angle (°) | d Space (Å) | Relative Intensity (%) |
| --- | --- | --- |
| 8.07 | 10.9511 | 52.7 |
| 9.21 | 9.5984 | 41.8 |
| 10.58 | 8.3604 | 19.2 |
| 10.88 | 8.1318 | 17.4 |
| 12.06 | 7.3409 | 48.5 |
| 14.56 | 6.0822 | 22.0 |
| 14.87 | 5.9564 | 22.1 |
| 16.28 | 5.4434 | 21.3 |
| 17.45 | 5.0817 | 58.1 |
| 17.79 | 4.9851 | 48.4 |
| 18.53 | 4.7887 | 98.0 |
| 19.65 | 4.5174 | 35.7 |
| 20.05 | 4.4277 | 17.4 |
| 20.85 | 4.2615 | 100.0 |
| 21.10 | 4.2108 | 83.7 |
| 23.72 | 3.7519 | 4.5 |
| 24.41 | 3.6467 | 19.0 |
| 25.11 | 3.5470 | 15.8 |
| 25.98 | 3.4300 | 16.6 |
| 26.61 | 3.3499 | 5.2 |
| 27.94 | 3.1938 | 9.7 |
| 29.25 | 3.0532 | 4.4 |
| 30.40 | 2.9405 | 6.1 |
| 32.00 | 2.7967 | 1.7 |
| 34.06 | 2.6325 | 2.8 |
| 35.72 | 2.5139 | 3.6 |
| 36.58 | 2.4567 | 3.1 |
| 37.59 | 2.3928 | 3.2 |

FIG. 29 provides a $^1$H NMR (DMSO-d$_6$) of Form F with δ 0.94 (d, J=6.4 Hz, 3H), 0.96-1.04 (m, 1H), 1.04-1.29 (m, 3H), 1.35 (s, 9H), 1.67 (dd, J=3.3, 13.1 Hz, 1H), 1.90 (d, J=9.3 Hz, 1H), 2.06-2.23 (m, 1H), 2.30 (s, 0.9H, toluene), 2.89-3.04 (m, 1H), 3.71-4.00 (m, 1H), 4.57 (d, J=5.7 Hz, 1H), 6.64 (br. s., 1H), 6.94 (br. s., 1H), 7.08-7.30 (m, 1.4H, toluene), 7.50 (br. s., 1H), 8.34 (s, 1H), 8.93 (br. s., 1H).

Form G

Form G was obtained from recrystallization or slurry experiments of Form A in EtOAc. Form G had a crystalline XRPD pattern as shown in FIG. 30. TGA and DSC thermograms of Form G are shown in FIG. 31 and FIG. 32, respectively. The TGA weight loss of 11.9 wt % corresponded to small broad DSC peak around 116° C. and can be attributed to loss of solvent in Form G. The major DSC peak with onset temperature of 223° C. corresponded to the melt/decomposition of Form A. The $^1$H-NMR spectrum obtained for the Form G sample showed approximately 0.5 molar equivalents of EtOAc (see FIG. 33). The theoretical EtOAc content of a hemi-solvate of Compound 1 is 12.1 wt %, matching the TGA weight loss observed. These observations suggested that Form G is an EtOAc hemi-solvate of Compound 1. Form transfer experiment showed that heating Form G above the desolvation temperature resulted in Form A. Slurry of Form G in water also resulted in Form A.

A list of X-Ray Diffraction Peaks for Form G is provided below in Table 14.

TABLE 14

X-Ray Diffraction Peaks for Form G

| Two-theta angle (°) | d Space (Å) | Relative Intensity (%) |
| --- | --- | --- |
| 8.63 | 10.2508 | 0.7 |
| 9.51 | 9.3026 | 100.0 |
| 10.34 | 8.5585 | 15.1 |
| 12.14 | 7.2888 | 0.5 |
| 14.43 | 6.1377 | 2.3 |
| 16.44 | 5.3907 | 1.3 |
| 16.94 | 5.2347 | 10.9 |
| 17.33 | 5.1185 | 5.0 |
| 17.90 | 4.9555 | 17.9 |
| 18.58 | 4.7768 | 4.2 |
| 19.10 | 4.6467 | 0.9 |
| 20.09 | 4.4211 | 0.4 |
| 20.41 | 4.3507 | 2.1 |
| 20.80 | 4.2704 | 0.4 |
| 21.28 | 4.1747 | 34.8 |
| 22.66 | 3.9240 | 0.4 |
| 23.62 | 3.7671 | 0.3 |
| 24.33 | 3.6584 | 2.8 |
| 25.55 | 3.4842 | 1.6 |
| 25.65 | 3.4726 | 1.9 |
| 26.42 | 3.3739 | 1.1 |
| 26.89 | 3.3128 | 0.3 |
| 27.00 | 3.3030 | 0.4 |
| 27.78 | 3.2114 | 0.9 |
| 28.83 | 3.0969 | 9.1 |
| 29.86 | 2.9925 | 1.5 |
| 31.22 | 2.8651 | 6.8 |
| 31.77 | 2.8164 | 0.1 |
| 32.67 | 2.7410 | 0.2 |
| 33.90 | 2.6443 | 0.7 |
| 34.28 | 2.6156 | 0.2 |
| 35.04 | 2.5606 | 0.5 |
| 35.44 | 2.5326 | 0.2 |
| 36.24 | 2.4789 | 0.5 |
| 36.57 | 2.4574 | 0.5 |
| 37.59 | 2.3926 | 0.4 |
| 38.00 | 2.3681 | 0.3 |
| 38.76 | 2.3231 | 0.4 |

FIG. 33 provides a $^1$H NMR (DMSO-d$_6$) of Form G with δ 0.94 (d, J=6.4 Hz, 3H), 0.96-1.04 (m, 1H), 1.04-1.29 (m, 5H) {include 1.17 (t, J=9.0 Hz, EtOAc)}, 1.29-1.46 (m, 9H), 1.60-1.76 (m, 1H), 1.86-1.96 (m, 1H), 1.99 (s, 1.4H, EtOAc), 2.04-2.16 (m, 1H), 2.88-3.06 (m, 1H), 3.75-3.97 (m, 1H), 4.03 (q, J=7.1 Hz, 1H, EtOAc), 4.57 (d, J=5.7 Hz, 1H), 6.65 (br. s., 1H), 6.94 (br. s., 1H), 7.52 (br. s., 1H), 8.34 (s, 1H), 8.93 (br. s., 1H).

Form H

Form H was obtained from recrystallization or slurry of Form A in DMSO. Form H had a crystalline XRPD pattern as shown in FIG. 34. TGA and DSC thermograms of Form H are shown in FIG. 35 and FIG. 36, respectively. The TGA thermogram showed a step weight loss of 11.2 wt % corresponded to small broad DSC peak around 160° C. and can be attributed to loss of solvent in Form H. The major DSC peak with onset temperature of 222° C. corresponded to the melt/decomposition of Form A. The theoretical DMSO content of a hemi-solvate of Compound 1 is 10.8 wt %, matching the TGA weight loss observed. These observations suggested that Form H is a DMSO hemi-solvate of Compound 1. Form transfer experiment showed that heating Form H above the desolvation temperature resulted in Form A. Slurry of Form H in water also resulted in Form A.

A list of X-Ray Diffraction Peaks for Form H is provided below in Table 15.

TABLE 15

X-Ray Diffraction Peaks for Form H

| Two-theta angle (°) | d Space (Å) | Relative Intensity (%) |
|---|---|---|
| 8.69 | 10.1702 | 5.5 |
| 9.74 | 9.0820 | 55.8 |
| 10.23 | 8.6432 | 16.7 |
| 12.17 | 7.2715 | 2.4 |
| 14.64 | 6.0510 | 15.1 |
| 15.38 | 5.7625 | 0.7 |
| 16.33 | 5.4296 | 3.7 |
| 17.22 | 5.1496 | 52.2 |
| 18.04 | 4.9185 | 22.8 |
| 18.55 | 4.7842 | 12.7 |
| 20.10 | 4.4170 | 3.0 |
| 20.62 | 4.3067 | 5.6 |
| 21.76 | 4.0836 | 100.0 |
| 23.10 | 3.8498 | 3.2 |
| 24.18 | 3.6807 | 8.3 |
| 25.65 | 3.4732 | 5.5 |
| 26.18 | 3.4044 | 3.9 |
| 26.78 | 3.3286 | 3.5 |
| 27.27 | 3.2703 | 1.1 |
| 27.83 | 3.2057 | 0.6 |
| 28.43 | 3.1396 | 7.2 |
| 29.50 | 3.0279 | 6.6 |
| 30.00 | 2.9782 | 0.6 |
| 30.54 | 2.9272 | 6.6 |
| 31.03 | 2.8821 | 2.5 |
| 32.07 | 2.7910 | 0.5 |
| 32.65 | 2.7425 | 0.4 |
| 33.41 | 2.6817 | 1.0 |
| 33.74 | 2.6569 | 1.4 |
| 34.86 | 2.5738 | 1.0 |
| 35.25 | 2.5460 | 2.0 |
| 35.77 | 2.5106 | 1.6 |
| 36.22 | 2.4803 | 2.0 |
| 36.62 | 2.4537 | 2.3 |
| 37.08 | 2.4243 | 0.7 |
| 37.59 | 2.3929 | 0.8 |
| 38.78 | 2.3220 | 2.3 |

A $^1$H NMR (MeOD) of Form H provides δ as 1.03 (d, J=6.2 Hz, 3H), 1.05-1.19 (m, 1H), 1.19-1.38 (m, 3H), 1.45 (s, 9H), 1.78 (dq, J=3.3, 13.2 Hz, 1H), 1.90-2.16 (m, 1H), 2.16-2.40 (m, 1H), 2.65 (s, 3H, DMSO), 2.95-3.24 (m, 1H), 3.85-4.21 (m, 1H), 8.25 (s, 1H).

Form I

Form I was obtained from recrystallization of Form A in sulfolane and water (1:1). Form I had a crystalline XRPD pattern as shown in FIG. 38. DSC thermograms of Form I are shown in FIG. 39. A DSC peak around 118° C. can be attributed to loss of solvent in Form I. The major DSC peak with maximum temperature of 213° C. corresponded to the melt/decomposition of Form A. $^1$H-NMR spectrum of Form I shows approximately 0.75 molar equivalents of sulfolane (see FIG. 40). These observations suggested that Form H is a 0.75 molar sulfolane solvate of Compound 1.

A list of X-Ray Diffraction Peaks for Form I is provided below in Table 16.

TABLE 16

X-Ray Diffraction Peaks for Form I

| Two-theta angle (°) | d Space (Å) | Relative Intensity (%) |
|---|---|---|
| 7.94 | 11.1290 | 72.2 |
| 10.50 | 8.4267 | 21.5 |
| 10.80 | 8.1909 | 16.7 |
| 11.86 | 7.4599 | 25.3 |
| 13.54 | 6.5394 | 11.7 |
| 13.92 | 6.3612 | 3.2 |
| 14.79 | 5.9901 | 2.1 |
| 16.00 | 5.5389 | 76.2 |
| 17.26 | 5.1378 | 45.0 |
| 18.27 | 4.8557 | 100.0 |
| 18.82 | 4.7163 | 4.9 |
| 19.48 | 4.5569 | 4.3 |
| 19.78 | 4.4881 | 9.1 |
| 20.65 | 4.3022 | 62.9 |
| 21.31 | 4.1699 | 4.4 |
| 21.78 | 4.0812 | 1.2 |
| 22.83 | 3.8959 | 5.0 |
| 23.53 | 3.7808 | 3.3 |
| 24.12 | 3.6899 | 29.4 |
| 24.75 | 3.5973 | 7.6 |
| 25.66 | 3.4715 | 4.7 |
| 26.29 | 3.3903 | 6.0 |
| 27.71 | 3.2189 | 17.4 |
| 28.18 | 3.1666 | 0.9 |
| 28.73 | 3.1072 | 0.7 |
| 29.17 | 3.0616 | 1.2 |
| 30.01 | 2.9778 | 1.5 |
| 30.52 | 2.9288 | 1.0 |
| 31.18 | 2.8687 | 0.7 |
| 31.60 | 2.8311 | 0.4 |
| 31.85 | 2.8099 | 2.1 |
| 32.36 | 2.7664 | 6.5 |
| 32.93 | 2.7203 | 0.7 |
| 33.59 | 2.6678 | 2.7 |
| 34.20 | 2.6219 | 0.9 |
| 34.76 | 2.5812 | 0.4 |
| 35.42 | 2.5341 | 0.6 |
| 36.56 | 2.4577 | 0.5 |
| 37.67 | 2.3880 | 1.1 |

Figure 40:
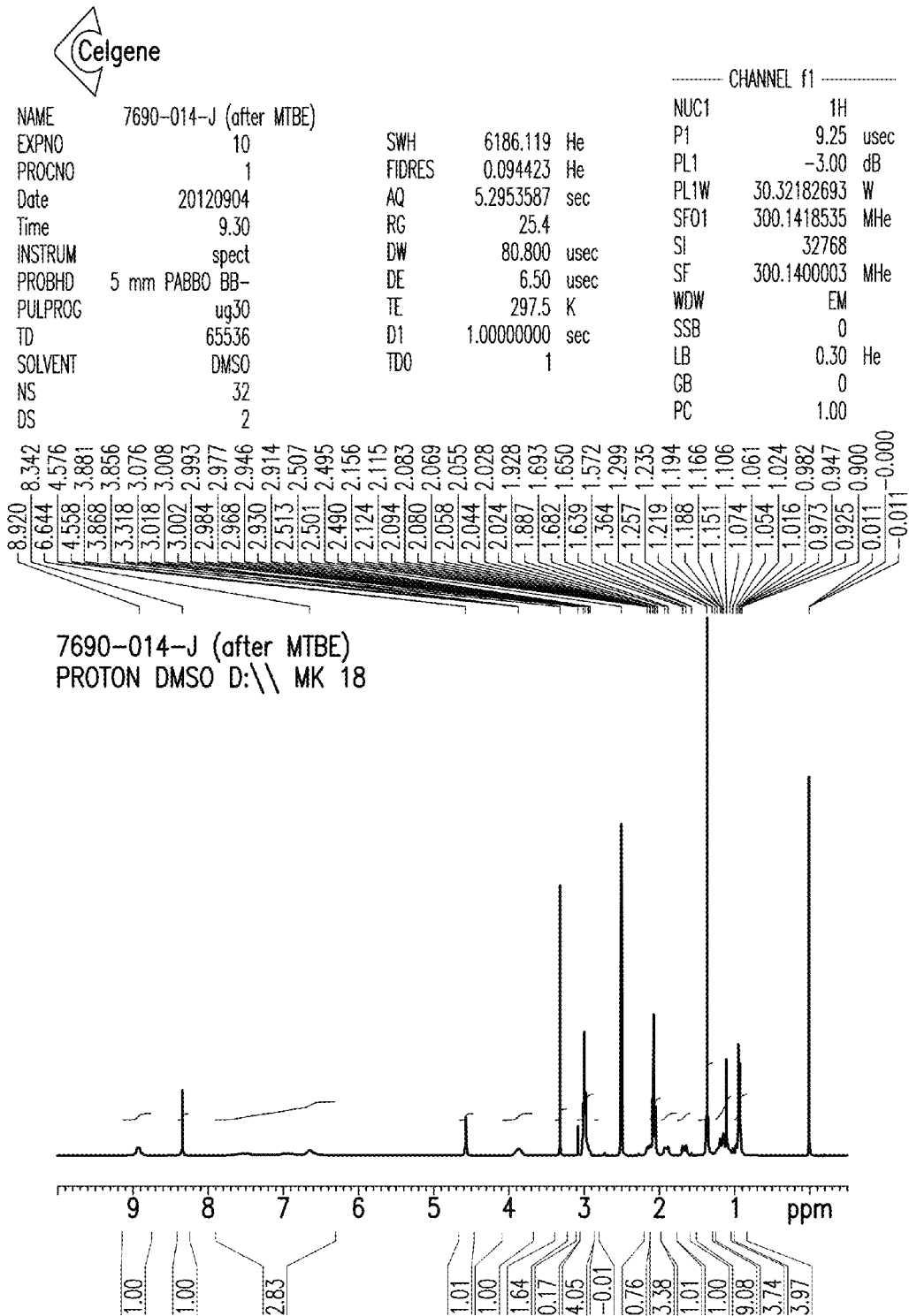
FIG. 40 depicts a $^1$H NMR spectrum of Form I.

FIG. 40 provides a $^1$H NMR (DMSO-$d_6$) of Form I with δ 0.94 (d, J=6.2 Hz, 3H), 0.96-1.04 (m, 1H), 1.11 (s, 3H), 1.36 (s, 9H), 1.59-1.74 (m, 1H), 1.83-1.98 (m, 1H), 2.00-2.20 (m, 4H), 2.80-3.18 (m, 4H), 3.74-4.02 (m, 1H), 4.57 (d, J=5.5 Hz, 1H), 6.64 (br. s., 1H), 7.02 (br. s., 1H), 7.60 (br. s., 1H), 8.34 (s, 1H), 8.82-9.06 (m, 1H).

Amorphous Solid

An amorphous solid of Compound 1 was obtained from heat treatment of Form A. The heat treatment process comprises: (1) equilibrating the temperature of Form A at 25° C.; (2) heating to 235° C. at the speed of 10° C. per minute; (3) holding isothermally for 2 minutes; (4) cooling down to −10° C. at the speed of 30° C. per minute; (5) modulating 0.64° C. every 40 seconds; (6) holding isothermally for 5 minutes; (7) heating to 213° C. at the speed of 3° C. per minute; and (8) collecting the resulted solid.

The amorphous solid had an XRPD spectrum as shown in FIG. 41. DSC thermogram of the amorphous solid sample are shown in FIG. 42. The amorphous solid has a glass transition temperature of approximately 106.6° C.

Figure 43:
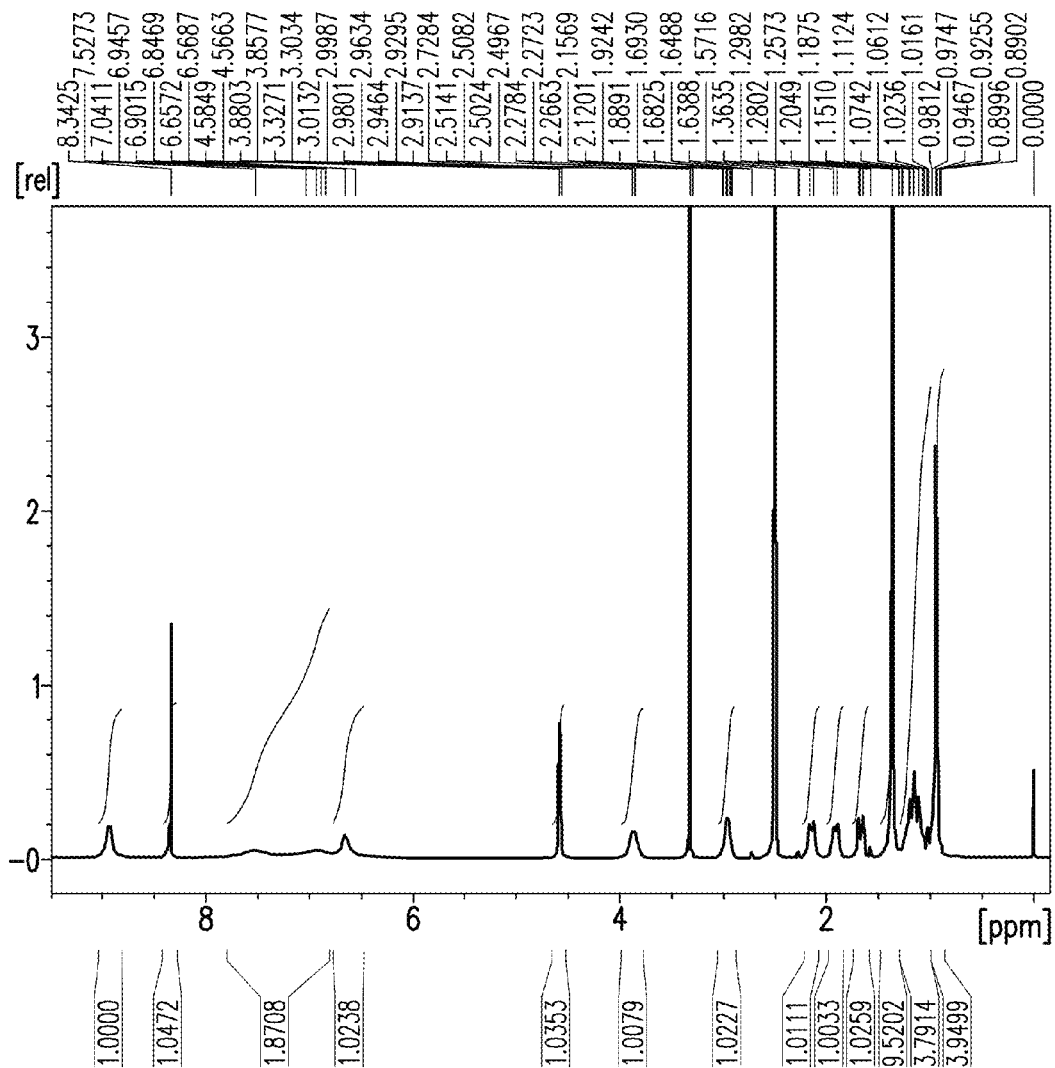
FIG. 43 depicts a $^1$H NMR spectrum of the amorphous solid.
Figure 44:
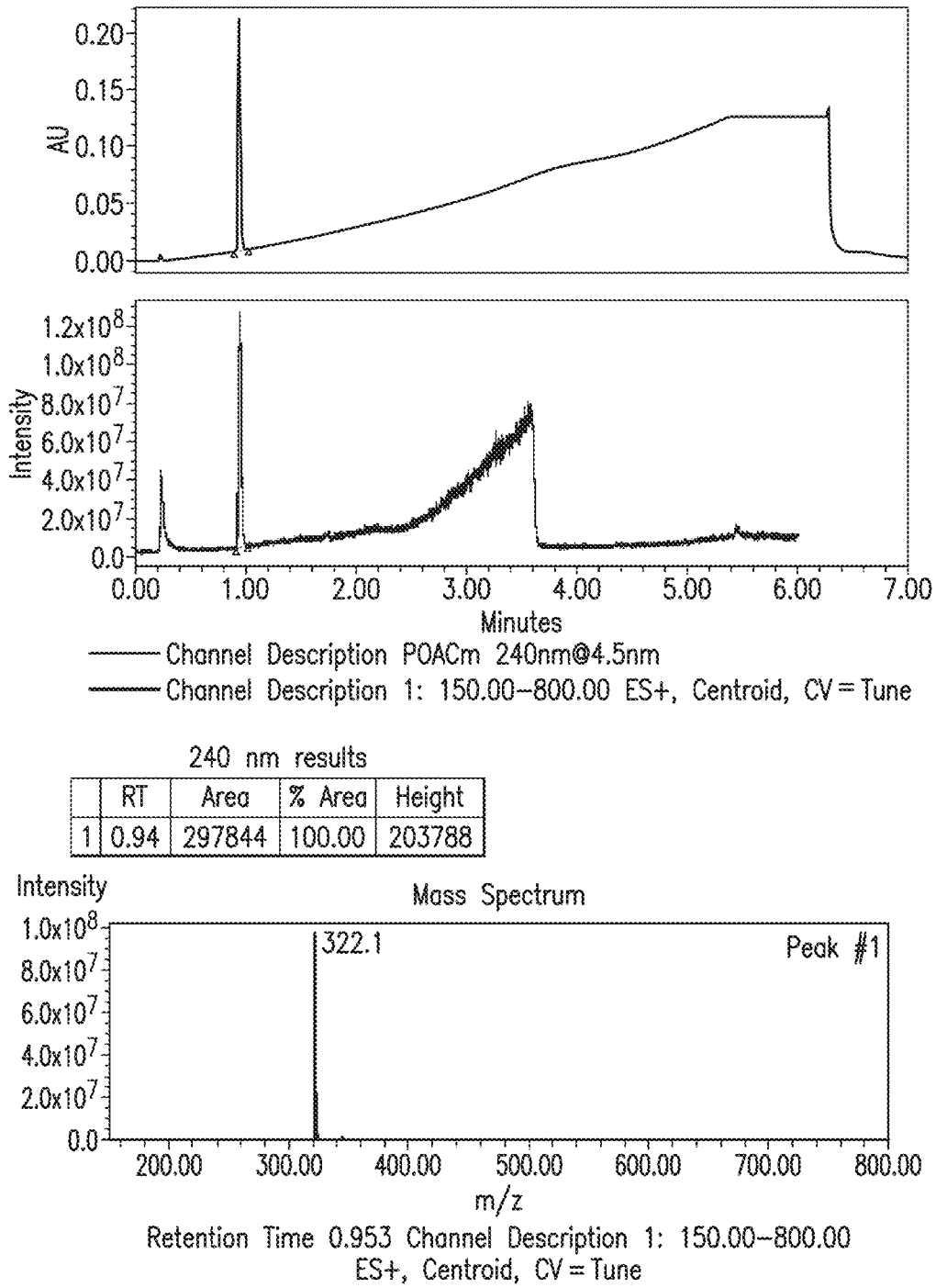
FIG. 44 depicts a Liquid Chromatography with Mass Spectroscopy of the amorphous solid.

FIG. 43 and FIG. 44 provide $^1$H-NMR spectrum and LCMS of the amorphous solid.

Biological Examples

Biochemical Assays

A. Time Resolved Fluorescence Assays
JNK1 Assay.

A 384-well time resolved fluorescence assay can be used to monitor JNK1 activity. The JNK1 assay can be run in the following assay buffer: 50 mM HEPES, 10 mM $MgCl_2$, 1 mM EGTA, 2 mM DTT, and 0.01% Tween 20. To initiate the reaction 100 nM of ULight™-labeled 4EBP1 peptide (Perkin-Elmer) and 5 µM of ATP can be mixed with 500 pM of JNK1 (Carna Biosciences), for a total assay volume of 20 µL in each well. The assay can be incubated at room temperature for 1 h and terminated using a mixture of 30 mM EDTA and 4 nM Eu-anti-4EBP1, by adding 20 µL of stop solution to each well. Plates can be read on a Perkin-Elmer Envision Reader.

JNK2 Assay.

A 384-well time resolved fluorescence assay can be used to monitor JNK2 activity. The JNK2 assay can be run in the following assay buffer: 50 mM HEPES, 10 mM $MgCl_2$, 1 mM EGTA, 2 mM DTT, and 0.01% Tween 20. To initiate the reaction 100 nM of ULight™-labeled 4EBP1 peptide (Perkin-Elmer) and 5 µM of ATP can be mixed with 500 pM of JNK2 (Carna Biosciences), for a total assay volume of 20 µL in each well. The assay can be incubated at room temperature for 1 h and terminated using a mixture of 30 mM EDTA and 4 nM Eu-anti-4EBP1, by adding 20 µL of stop solution to each well. Plates can be read on a Perkin-Elmer Envision Reader.

B. Z'-LYTE® Cascade Assays
JNK1 Assay.

The JNK1 Z'-LYTE® Cascade kinase assay can be run in the following buffer: 50 mM HEPES at pH 7.5, 0.01% BRIJ-35, 10 mM $MgCl_2$, 1 mM EGTA, and 1 mM DTT. A 10 µL kinase reaction mixture can be prepared containing 1.81-7.25 ng JNK1, 25 ng inactive MAPKAPK2, 100 µM ATP, and 2 µM Ser/Thr 04 peptide. The assay can be incubated at room temperature for 1 h. Next, 5 µL of a 1:512 dilution of Development Reagent A (Invitrogen, PV3295) can be added to the reaction mixture and incubated at room temperature for an additional h. The data can then be read on a fluorescence plate reader and analyzed.

JNK2 Assay.

The JNK2 Z'-LYTE® Cascade kinase assay can be run in the following buffer: 50 mM HEPES pH 7.5, 0.01% BRIJ-35, 10 mM $MgCl_2$, 1 mM EGTA, 2 mM DTT. A 10 µL kinase reaction mixture can be prepared containing 0.38-1.5 ng JNK2, 100 ng inactive MAPKAPK2, 100 µM ATP, and 2 µM Ser/Thr 04 peptide. The assay can be incubated at room temperature for 1 h. Next, 5 µL of a 1:512 dilution of Development Reagent A (Invitrogen, PV3295) can be added to the reaction mixture and incubated at room temperature for an additional h. The data can then be read on a fluorescence plate reader and analyzed.

C. Radioactive Assays
JNK1 Assay.

The radioactive JNK kinase assay can be carried out in a 96-well plate format at a final volume of 100 µL. The final assay concentration can be 6.6 µM ATP (3-fold ATP Km), 2.64 to 5 µg/mL JNK1, and 100 µg/mL cJUN. JNK1 can be diluted in the following dilution buffer (20 mM HEPES pH 7.6, 0.1 mM EDTA, 2.5 mM $MgCl_2$, 0.004%(w/v) Triton X100, 2 µg/ml Leupeptin, 20 mM B-glycerol phosphate, 0.1 mM $Na_3VO_4$ dithiothreitol) and then pre-mixed with cJun diluted in the substrate solution buffer (20 mM HEPES pH 7.6, 50 mM NaCl, 0.1 mM EDTA, 2.5 mM $MgCl_2$, 0.05%(w/v) Triton X100). The JNK1/cJun mix (85 µl) can be added to the inhibitor (5 µl) diluted in 100% DMSO to give a final DMSO assay concentration of 5%(v/v). The enzyme, substrate and inhibitor mixture can be allowed to equilibrate at room temperature for 15 minutes. The reaction can be started by the addition of 10 µL of 10×ATP in kinase buffer (130 mM $MgCl_2$, 6 mM dithiothreitol, 150 mM para-nitrophenyl phosphate, 100 µCi/ml γ-[$^{33}$P]-ATP). Reactions can be allowed to proceed for 60 minutes before precipitation of protein via trichloroacetic acid (7.2% TCA final). After a 30 minute incubation with TCA, reaction products can be collected onto glass microfilter 96-well plates (Millipore MAHF CIH60) using a Packard Filtermate. The precipitate can be washed with Phosphate Buffered Saline and the amount of phosphate incorporated into cJun can be quantified by scintillation counting using a Packard Topcount-NXT. All assays can be conducted under conditions where phosphate incorporation can be linear with respect to time and enzyme concentration. The $IC_{50}$ values can be calculated as the concentration of the inhibitor at which the c-Jun phosphorylation can be reduced to 50% of the control value.

JNK2 Assay.

The assay can be carried out in a 96-well plate format at a final volume of 100 µL. The final assay concentrations can be 6.6 µM ATP (3-fold ATP Km), 0.2 to 0.53 µg/mL JNK2, and 100 µg/mL cJUN. JNK2 can be diluted in the following dilution buffer (20 mM HEPES pH 7.6, 0.1 mM EDTA, 2.5 mM $MgCl_2$, 0.004%(w/v) Triton X100, 2 µg/ml Leupeptin, 20 mM B-glycerol phosphate, 0.1 mM $Na_3VO_4$ dithiothreitol) and then pre-mixed with cJun diluted in the substrate solution buffer (20 mM HEPES pH 7.6, 50 mM NaCl, 0.1 mM EDTA, 2.5 mM $MgCl_2$, 0.05% (w/v) Triton X100). The JNK2/cJun mix (85 µl) can be added to the inhibitor (5 µl) diluted in 100% DMSO to give a final DMSO assay concentration of 5%(v/v). The enzyme, substrate and inhibitor mixture can be allowed to equilibrate at room temperature for 15 minutes. The reaction can be started by the addition of 10 µL of 10×ATP in kinase buffer (130 mM $MgCl_2$, 6 mM dithiothreitol, 150 mM para-nitrophenyl phosphate, 100 µCi/ml γ-[$^{33}$P]-ATP). Reactions can be allowed to proceed for 60 minutes before precipitation of protein via trichloroacetic acid (7.2% TCA final). After a 30 minute incubation with TCA, reaction products are collected onto glass microfilter 96-well plates (Millipore MAHF CIH60) using a Packard Filtermate. The precipitate can be washed with Phosphate Buffered Saline and the amount of phosphate incorporated into cJun can be quantified by scintillation counting using a Packard Topcount-NXT. All assays can be conducted under conditions where phosphate incorporation can be linear with respect to time and enzyme concentration. The $IC_{50}$ values can be calculated as the concentration of the inhibitor at which the c-Jun phosphorylation can be reduced to 50% of the control value.

Cell Assays

RAW264.7 Phospho-cJun Whole Cell Assay.

RAW264.7 cells can be purchased from the American Tissue Culture Collection and maintained in growth media consisting of 90% high glucose Dulbecco's Modified Eagle Medium (Invitrogen), 10% fetal bovine serum (Hyclone), and 2 mM L-glutamine (Invitrogen). All cells can be cultured at 37° C. in 95% air and 5% $CO_2$. Cells can be plated at a density of $1.0 \times 10^5$ cells per well in a 96-well plate in 120 µL of growth media. Diaminopyrimidine Compound stock (30 mM) can be diluted serially in DMSO, further diluted in growth media, and can be added to each well as a 10× concentrated solution in a volume of 15 µL, mixed, and allowed to incubate with cells. The compound vehicle (DMSO) can be maintained at a final concentration of 0.2% in all wells. After 30 minutes, the cells can be activated with lipopolysaccharide (ALEXIS Biochemicals) at a final concentration of 25 ng/mL. Lipopolysaccharide can be added as a 10× concentrated solution in growth media and added in a volume of 15 µL per well. Cell plates can be cultured for 1 h, after which the cell media can be removed. The level of c-Jun protein which can be phosphorylated at serine 63 can be measured according to the manufacturer's instructions for the Whole Cell Lysate Kit-Phospho-c-Jun (Ser 63) Assay (Meso Scale Discovery) with the exception that the concentration of NaCl in the lysis buffer can be increased to a final concentration of 350 mM. The $IC_{50}$ values can be calculated as the concentration of Diaminopyrimidine Compound at which the level of phosphorylated c-Jun protein can be reduced to 50% of the signal window. Certain compounds of Table 1, 2 and 3 have an $IC_{50}$ value ranging from 0.01-30 µM in this assay.

Jurkat T-Cell IL-2 Production Assay.

Jurkat T cells (clone E6-1) can be purchased from the American Tissue Culture Collection and maintained in growth media consisting of RPMI 1640 medium containing 2 mM L-glutamine (Mediatech), with 10% fetal bovine serum (Hyclone) and penicillin/streptomycin. All cells can be cultured at 37° C. in 95% air and 5% $CO_2$. Cells can be plated at a density of $1 \times 10^5$ cells per well in 120 µL of media in a 96-well plate. Diaminopyrimidine Compound stock (20 mM) can be diluted in growth media and added to each well as a 10× concentrated solution in a volume of 15 µL, mixed, and allowed to pre-incubate with cells for 30 min. The compound vehicle (dimethylsulfoxide) can be maintained at a final concentration of 0.2% in all samples. After 30 min the cells can be activated with PMA (phorbol myristate acetate; final concentration 50 ng/mL) and PHA (phytohemagglutinin; final concentration 1 µg/mL). PMA and PHA can be added as a 10× concentrated solution made up in growth media and added in a volume of 15 µL per well. Cell plates can be cultured for 6 h. Cells can be pelleted by centrifugation and the media removed and stored at −20° C. Media aliquots can be analyzed according the manufacturers instructions for the Human IL-2 Tissue Culture Kit (Meso Scale Discovery). The $IC_{50}$ values can be calculated as the concentration of the Diaminopyrimidine Compound at which the IL-2 production can be reduced to 50% of the signal window. Certain compounds from Table 1, 2 and 3 have an $IC_{50}$ value ranging from 0.01-10 µM in this assay.

Clinical Protocol

A Phase 1, Randomized, Two-Part Study to Evaluate the Safety, Tolerability, and Pharmacokinetics of Single and Multiple Ascending Doses of Compound 1 in Healthy Subjects.

The primary objective is to evaluate the safety and tolerability of single and multiple oral doses of Compound 1 in health subjects.

The secondary objectives are to assess the pharmacokinetics (PK) of Compound 1 following single and multiple oral doses.

Study Design.

This is a two-part study to be conducted at up to two study centers.

Part 1 is a randomized, double-blind, placebo-controlled study to evaluate the safety, tolerability, and PK of Compound 1 following a single oral dose in healthy subjects. Investigators and study participants will be blinded to treatment throughout the study, while the Sponsor will remain unblinded. The chosen study design is an escalating dose in sequential groups.

In Part 1, approximately 56 subjects will be randomized and enrolled into seven planned cohorts. Each cohort will consist of eight subjects; six subjects will receive Compound 1 and two subjects will receive placebo.

During the course of Part 1, each subject will participate in a screening phase, a baseline phase, a treatment phase, and a follow-up visit. Subjects will be screened for eligibility. Subjects who have met all inclusion criteria and none of the exclusion criteria at screening will return to the clinical site on Day−1 for baseline assessments, and will be domiciled at the clinical site from Day−1 to Day 4. Subjects will receive a single oral dose of investigational product (IP; either Compound 1 or placebo) on Day 1, under fasted conditions, according to the randomization schedule. Blood and urine samples will be collected at pre-specified times for PK and/or clinical laboratory assessments and/or exploratory analyses. Safety will be monitored throughout the study. Subjects will be discharged from the clinical site on Day 4 following completion of the required study procedures and will return to the clinical site for a follow-up visit on Day 7 (±1-day window). In the event that a subject discontinues from the study, an early termination (ET) visit will be performed.

After each cohort, safety data will be reviewed and PK data will be reviewed as needed. The parameters to be reviewed prior to each dose escalation along with specific dose escalation.

Part 2 is a randomized, double-blind, placebo-controlled study to evaluate the safety, tolerability, and PK of Compound 1 following multiple oral doses (up to 14 days of dosing) in healthy subjects. Investigators and study participants will be blinded to treatment throughout the study, while the Sponsor will remain unblinded. The chosen study design is an escalating dose in sequential groups.

Part 2 will not begin until total daily doses up to and including 240 mg have been evaluated in Part 1. Only doses that are safe and well tolerated in Part 1 will be administered in Part 2.

In Part 2, approximately 48 subjects will be randomized and enrolled into six planned cohorts. Each cohort will consist of eight subjects; six subjects will receive Compound 1 and two subjects will receive placebo.

During the course of Part 2, each subject will participate in a screening phase, a baseline phase, a treatment phase, and a follow-up visit. Subjects will be screened for eligibility. Subjects who have met all inclusion criteria and none of the exclusion criteria at screening will return to the clinical site on Day 1 for baseline assessments, and will be domiciled at the clinical site from Day 1 to Day 17. The first dose of IP (either Compound 1 or placebo) will be administered on Day 1, under fasted conditions, according to the randomization schedule. The same total daily dose will be administered under fasted conditions on Days 2 to 14. Blood samples will be collected at pre-specified times for PK, clinical laboratory assessments, and/or exploratory biomarkers. Urine samples will be collected at pre-specified times for clinical laboratory assessments. Safety will be monitored throughout the study. Subjects will be discharged from the clinical site on Day 17 following completion of the required study procedures and will return to the clinical site for a follow-up visit on Day 21 (±1-day window). In the event that a subject discontinues from the study, an ET visit will be performed.

After each cohort, safety data will be reviewed and PK data will be reviewed as needed. The parameters will be reviewed prior to each dose escalation along with specific dose escalation.

Study Population:

Approximately 104 healthy adult subjects (males or females of non-childbearing potential) from any race between 18 and 50 years of age, inclusive, will be enrolled into the study, with approximately 56 subjects participating in Part 1 and approximately 48 subjects participating in Part 2.

Length of Study:

The estimated duration of the study, inclusive of Parts 1 and 2, from first-subject-first-visit to last-subject-last-visit, is approximately 8 months.

The estimated duration of the clinical phase of Part 1, from first-subject-first-visit to last-subject-last-visit, is approximately 4 months. The estimated duration of each subject's participation in Part 1, from screening through follow-up, is approximately 4 weeks.

Part 2 will not begin until total daily doses up to and including 240 mg have been evaluated in Part 1. Only doses that are safe and well tolerated in Part 1 will be administered in Part 2. The estimated duration of the clinical phase of Part 2, from first-subject-first-visit to last-subject-last-visit, is approximately 6 months. The estimated duration of each subject's participation in Part 2, from screening through follow-up, is approximately 6 weeks.

The End of Trial is defined as either the date of the last visit of the last subject to complete the study, or the date of receipt of the last data point from the last subject that is required for primary, secondary and/or exploratory analysis, as pre-specified in the protocol and/or the Statistical Analysis Plan, whichever is the later date.

Study Treatments.

Part 1:

Approximately 56 subjects will be randomized and enrolled into seven planned cohorts, with eight subjects per cohort. In each cohort, six subjects will receive Compound 1 and two subjects will receive placebo.

Doses in Part 1 will be administered as active pharmaceutical ingredient (API) in capsules (or matching placebo) once daily (QD).

The following Compound 1 dose levels in Table 17 are planned for Part 1.

TABLE 17

Compound 1 Dose Levels in Part 1

| Cohort | Compound 1 Dose Level (Total Daily Dose) |
|---|---|
| 1A | 10 mg |
| 1B | 30 mg |
| 1C | 60 mg |
| 1D | 120 mg |
| 1E | 240 mg |
| 1F | 480 mg |
| 1G | 720 mg |

If gastrointestinal (GI)-related events such as intolerable nausea or vomiting occur, total daily doses may be lowered or may be administered BID or three times daily (TID).

Investigational product will be administered at only one dose level at a time, and administration at the next dose level will not begin until the safety and tolerability of the preceding dose level have been evaluated and deemed acceptable by the Investigator and Sponsor's Medical Monitor.

Part 2:

Part 2 will not begin until total daily doses up to and including 240 mg have been evaluated in Part 1. Only doses that are safe and well tolerated in Part 1 will be administered in Part 2.

Approximately 48 subjects will be randomized and enrolled into six planned cohorts, with eight subjects per cohort. In each cohort, six subjects will receive Compound 1 and two subjects will receive placebo.

The planned dosing regimen in Part 2 is Compound 1 in capsules (or matching placebo) QD for 14 days. The following Compound 1 dose levels in Table 18 are proposed for Part 2.

TABLE 18

Compound 1 Dose Levels in Part 2

| Cohort | Compound 1 Dose Level (Total Daily Dose) | Duration |
|---|---|---|
| 2A | 10 mg | Daily × 14 days |
| 2B | 30 mg | Daily × 14 days |
| 2C | 60 mg | Daily × 14 days |
| 2D | 120 mg | Daily × 14 days |
| 2E | 240 mg | Daily × 14 days |
| 2F | 480 mg | Daily × 14 days |

Proposed dose levels in Part 2 may be modified and/or eliminated based on data obtained from Part 1. Should a change to the proposed dose escalation step(s) be required, the maximum dose escalation step in Part 2 will be ≤3-fold the previous dose level. In addition, the maximum dose administered in Part 2 will not exceed the maximum tolerated dose (MTD) in Part 1 and will not exceed 480 mg daily for 14 days.

If GI-related events such as intolerable nausea or vomiting occur, total daily doses may be lowered or may be administered BID or TID.

Investigational product will be administered at only one dose level at a time, and administration at the next dose level will not begin until the safety and tolerability of the preceding dose level have been evaluated and deemed acceptable by the Investigator and Sponsor's Medical Monitor. In addition, if a certain dose level is not tolerated in Part 1 then that dose level or any higher dose level will not be administered in Part 2 except for the instance of a GI intolerability (e.g., nausea, vomiting) that is mitigated via an alternative dose regimen (i.e., BID or TID).

Overview of Safety Assessments.

Safety will be monitored throughout the study. Safety evaluations will include AE reporting, PEs, vital signs, 12-lead ECGs, clinical laboratory safety tests (including liver function tests [LFTs], total cholesterol, triglycerides, high-density lipoprotein [HDL], and low-density lipoprotein [LDL] in addition to standard clinical chemistry, hematology, and urinalysis tests), review of concomitant medications/procedures, FOB tests and stool monitoring, and pregnancy tests for female subjects. All AEs will be monitored and recorded throughout the study from the time the informed consent form (ICF) is signed until study completion, and when made known to the Investigator within 28 days after the last dose of IP (and those SAEs made known to the Investigator at any time thereafter that are suspected of being related to IP). All concomitant medications and procedures will be reviewed and recorded from the time the subject signs the ICF until study completion. A follow-up visit will be scheduled for all subjects. If a subject is discontinued from the study for any reason, an ET visit will be performed.

Overview of Pharmacokinetic Assessments.

In both parts of the study, blood samples will be collected at pre-specified times to determine levels of Compound 1 in plasma. For Cohorts 1C to 1G of Part 1 (planned dose levels of 60 mg to 720 mg), urine samples will be collected at pre-specified times for exploratory metabolite analyses. Prominent metabolites in plasma and urine will be identified and Compound 1 in urine may be quantified as part of the exploratory analyses.

The following PK parameters will be estimated for Compound 1, as appropriate: maximum observed plasma concentration ($C_{max}$); time to Cmax ($T_{max}$); area under the plasma concentration-time curve from time zero extrapolated to infinity ($AUC_\infty$); area under the plasma concentration-time curve from time zero to the last quantifiable concentration ($AUC_t$); area under the plasma concentration-time curve from time zero to tau ($\tau$), where $\tau$ is the dosing interval ($AUC_\tau$); terminal-phase elimination half-life ($t_{1/2,z}$); apparent total plasma clearance when dosed orally (CL/F); apparent total volume of distribution when dosed orally, based on the terminal phase ($V_z/F$); ratio of accumulation (RA) based on Day 1 and Day 14 $AUC_\tau$.

Compound 1 concentrations in urine samples collected in Part 1 may be further quantified using a validated method if exploratory analyses indicate that Compound 1 is abundant in urine. The following PK parameters related to urine analyses may then be determined, as appropriate: cumulative amount of drug excreted unchanged in urine during the collection period from predose (0-hour) to the end of collection (Ae); cumulative percentage of the administered dose excreted unchanged in urine during the collection period from predose (0-hour) to the end of collection (fe); renal clearance ($CL_r$).

A number of references have been cited, the disclosures of which are incorporated herein by reference in their entirety.

What is claimed is:

1. Crystal Form A of Compound 1, or a tautomer thereof:

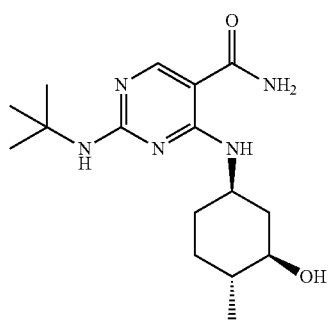

which has an X-ray powder diffraction pattern comprising peaks at approximately 10.55, 13.61 and 19.84° 2θ.

2. Crystal Form B of Compound 1, or a tautomer thereof:

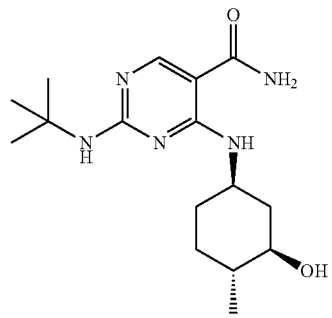

which has an X-ray powder diffraction pattern comprising peaks at approximately 9.80, 17.29 and 21.74° 2θ.

3. Crystal Form C of Compound 1, or a tautomer thereof:

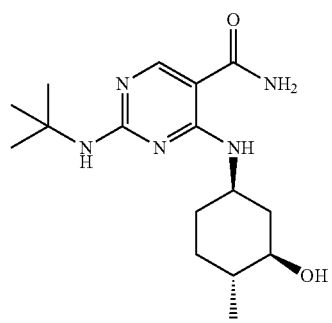

which has an X-ray powder diffraction pattern comprising peaks at approximately 9.83, 17.26 and 21.86° 2θ.

4. Crystal Form D of Compound 1, or a tautomer thereof:

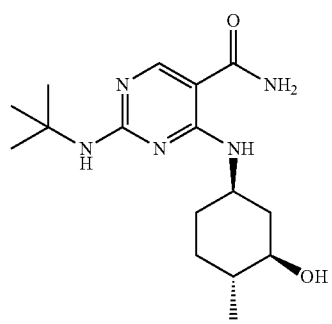

which has an X-ray powder diffraction pattern comprising peaks at approximately 10.37, 13.41 and 19.52° 2θ.

5. Crystal Form E of Compound 1, or a tautomer thereof:

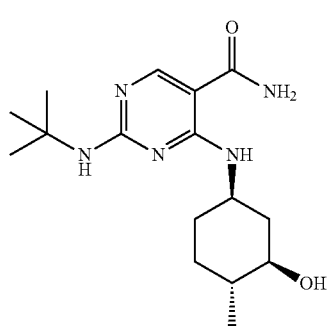

which has an X-ray powder diffraction pattern comprising peaks at approximately 9.92, 17.29 and 21.81° 2θ.

6. Crystal Form F of Compound 1, or a tautomer thereof:

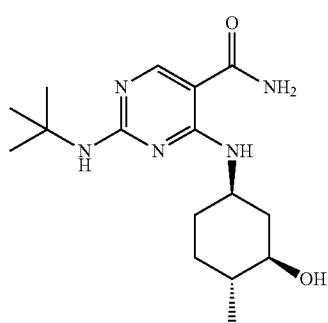

which has an X-ray powder diffraction pattern comprising peaks at approximately 18.53, 20.85 and 21.10° 2θ.

7. Crystal Form G of Compound 1, or a tautomer thereof:

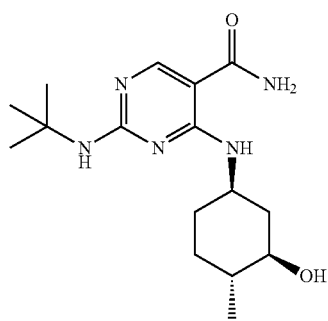

which has an X-ray powder diffraction pattern comprising peaks at approximately 9.51, 17.90 and 21.28° 2θ.

8. Crystal Form H of Compound 1, or a tautomer thereof:

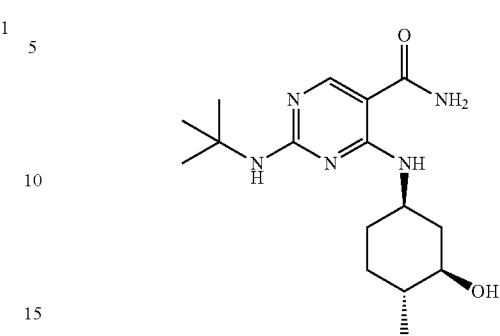

which has an X-ray powder diffraction pattern comprising peaks at approximately 9.74, 17.22 and 21.76° 2θ.

9. Crystal Form I of Compound 1, or a tautomer thereof:

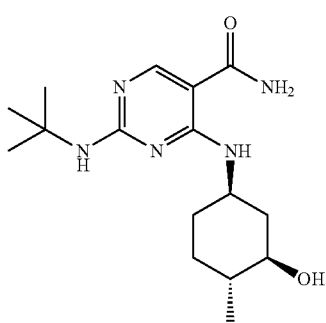

which has an X-ray powder diffraction pattern comprising peaks at approximately 7.94, 16.00 and 18.27° 2θ.

10. A method of inhibiting a JNK1 or JNK2 kinase in a cell expressing said JNK1 or JNK2 kinase, comprising contacting said cell with an effective amount of a crystal form of claim 1.

11. A method for treating interstitial pulmonary fibrosis, systemic sclerosis, scleroderma, chronic allograft nephropathy, antibody mediated rejection, or lupus, comprising administering an effective amount of a crystal form of claim 1 to a subject in need thereof.

12. A method for treating liver fibrotic disorders, diabetes, or metabolic syndrome leading to liver fibrotic disorders comprising administering an effective amount of a crystal form of claim 1 to a subject in need thereof.

13. A method of inhibiting a JNK1 or JNK2 kinase in a cell expressing said JNK1 or JNK2 kinase, comprising contacting said cell with an effective amount of a crystal form of claim 2.

14. A method for treating interstitial pulmonary fibrosis, systemic sclerosis, scleroderma, chronic allograft nephropathy, antibody mediated rejection, or lupus, comprising administering an effective amount of a crystal form of claim 2 to a subject in need thereof.

15. A method for treating liver fibrotic disorders, diabetes, or metabolic syndrome leading to liver fibrotic disorders comprising administering an effective amount of a crystal form of claim 2 to a subject in need thereof.

16. A method of inhibiting a JNK1 or JNK2 kinase in a cell expressing said JNK1 or JNK2 kinase, comprising contacting said cell with an effective amount of a crystal form of claim 3.

17. A method for treating interstitial pulmonary fibrosis, systemic sclerosis, scleroderma, chronic allograft nephropathy, antibody mediated rejection, or lupus, comprising administering an effective amount of a crystal form of claim 3 to a subject in need thereof.

18. A method for treating liver fibrotic disorders, diabetes, or metabolic syndrome leading to liver fibrotic disorders comprising administering an effective amount of a crystal form of claim 3 to a subject in need thereof.

19. A method of inhibiting a JNK1 or JNK2 kinase in a cell expressing said JNK1 or JNK2 kinase, comprising contacting said cell with an effective amount of a crystal form of claim 4.

20. A method for treating interstitial pulmonary fibrosis, systemic sclerosis, scleroderma, chronic allograft nephropathy, antibody mediated rejection, or lupus, comprising administering an effective amount of a crystal form of claim 4 to a subject in need thereof.

21. A method for treating liver fibrotic disorders, diabetes, or metabolic syndrome leading to liver fibrotic disorders comprising administering an effective amount of a crystal form of claim 4 to a subject in need thereof.

22. A method of inhibiting a JNK1 or JNK2 kinase in a cell expressing said JNK1 or JNK2 kinase, comprising contacting said cell with an effective amount of a crystal form of claim 5.

23. A method for treating interstitial pulmonary fibrosis, systemic sclerosis, scleroderma, chronic allograft nephropathy, antibody mediated rejection, or lupus, comprising administering an effective amount of a crystal form of claim 5 to a subject in need thereof.

24. A method for treating liver fibrotic disorders, diabetes, or metabolic syndrome leading to liver fibrotic disorders comprising administering an effective amount of a crystal form of claim 5 to a subject in need thereof.

25. A method of inhibiting a JNK1 or JNK2 kinase in a cell expressing said JNK1 or JNK2 kinase, comprising contacting said cell with an effective amount of a crystal form of claim 6.

26. A method for treating interstitial pulmonary fibrosis, systemic sclerosis, scleroderma, chronic allograft nephropathy, antibody mediated rejection, or lupus, comprising administering an effective amount of a crystal form of claim 6 to a subject in need thereof.

27. A method for treating liver fibrotic disorders, diabetes, or metabolic syndrome leading to liver fibrotic disorders comprising administering an effective amount of a crystal form of claim 6 to a subject in need thereof.

28. A method of inhibiting a JNK1 or JNK2 kinase in a cell expressing said JNK1 or JNK2 kinase, comprising contacting said cell with an effective amount of a crystal form of claim 7.

29. A method for treating interstitial pulmonary fibrosis, systemic sclerosis, scleroderma, chronic allograft nephropathy, antibody mediated rejection, or lupus, comprising administering an effective amount of a crystal form of claim 7 to a subject in need thereof.

30. A method for treating liver fibrotic disorders, diabetes, or metabolic syndrome leading to liver fibrotic disorders comprising administering an effective amount of a crystal form of claim 7 to a subject in need thereof.

31. A method of inhibiting a JNK1 or JNK2 kinase in a cell expressing said JNK1 or JNK2 kinase, comprising contacting said cell with an effective amount of a crystal form of claim 8.

32. A method for treating interstitial pulmonary fibrosis, systemic sclerosis, scleroderma, chronic allograft nephropathy, antibody mediated rejection, or lupus, comprising administering an effective amount of a crystal form of claim 8 to a subject in need thereof.

33. A method for treating liver fibrotic disorders, diabetes, or metabolic syndrome leading to liver fibrotic disorders comprising administering an effective amount of a crystal form of claim 8 to a subject in need thereof.

34. A method of inhibiting a JNK1 or JNK2 kinase in a cell expressing said JNK1 or JNK2 kinase, comprising contacting said cell with an effective amount of a crystal form of claim 9.

35. A method for treating interstitial pulmonary fibrosis, systemic sclerosis, scleroderma, chronic allograft nephropathy, antibody mediated rejection, or lupus, comprising administering an effective amount of a crystal form of claim 9 to a subject in need thereof.

36. A method for treating liver fibrotic disorders, diabetes, or metabolic syndrome leading to liver fibrotic disorders comprising administering an effective amount of a crystal form of claim 9 to a subject in need thereof.

* * * * *